(12) United States Patent
Engel et al.

(10) Patent No.: US 6,207,618 B1
(45) Date of Patent: Mar. 27, 2001

(54) HETEROCYCLIC SUBSTITUTED 4-BENZOYL-PYRAZOLE AS HERBICIDES

(75) Inventors: Stefan Engel, Wörrstadt; Joachim Rheinheimer, Ludwigshafen; Ernst Baumann, Dudenhofen; Wolfgang von Deyn, Neustadt; Regina Luise Hill, Speyer; Guido Mayer; Ulf Misslitz, both of Neustadt; Oliver Wagner, Ludwigshafen; Matthias Witschel, Ludwigshafen; Martina Otten, Ludwigshafen; Helmut Walter, Obrigheim; Karl-Otto Westphalen, Speyer, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/485,194

(22) PCT Filed: Jul. 23, 1998

(86) PCT No.: PCT/EP98/04635

§ 371 Date: Feb. 7, 2000

§ 102(e) Date: Feb. 7, 2000

(87) PCT Pub. No.: WO99/10328

PCT Pub. Date: Mar. 4, 1999

(30) Foreign Application Priority Data

Aug. 7, 1997 (DE) ............................ 197 34 148

(51) Int. Cl.[7] ........................ A01N 43/56; C07D 403/12
(52) U.S. Cl. ................ 504/282; 548/365.1; 548/364.1; 548/365.7; 546/276.1; 504/130; 504/139; 504/244; 504/282
(58) Field of Search .................... 504/280, 282, 504/116, 130, 139, 244; 548/365.1, 364.1, 365.7; 546/276.1

(56) References Cited

FOREIGN PATENT DOCUMENTS

| 282 944 | 9/1988 | (EP) . |
| 96/26206 | 8/1996 | (WO) . |
| 97/03045 | 1/1997 | (WO) . |
| 97/41105 | 11/1997 | (WO) . |

*Primary Examiner*—C. S. Aulakh
(74) *Attorney, Agent, or Firm*—Keil & Weinkauf

(57) ABSTRACT

Substituted 4-benzoylpyrazole of the formula I

I where:
Q is a pyrazole of the formula II

II $X^1$ is a straight-chain or branched $C_1$–$C_6$-alkylene, a $C_2$–$C_6$-alkenylene or a $C_2$–$C_6$-alkynylene chain which is interrupted by a hetero atom selected from the group consisting of:
  oxygen and sulfur, Het is a three- to six-membered partially or fully saturated heterocyclic group or a three- to six-membered heteroaromatic group having up to three hetero atoms selected from the following three groups:
  nitrogen,
  oxygen in combination with at least one nitrogen or
  sulfur in combination with at least one nitrogen;
and agriculturally useful salts thereof, processes and intermediates for preparing compounds of the formula I, compositions comprising them and the use of the compounds of the formula I and of compositions comprising them for controlling harmful plants are described.

10 Claims, No Drawings

HETEROCYCLIC SUBSTITUTED 4-BENZOYL-PYRAZOLE AS HERBICIDES

This application is a 371 of PCT/EP98/04635 Jul. 23, 1998 now WO 99/10328 Mar. 4, 1999.

The present invention relates to substituted 4-benzoylpyrazoles of the formula I

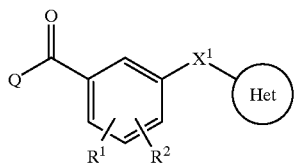

where:
$R^1$ and $R^2$ are each hydrogen, mercapto, nitro, halogen, cyano, thiocyanato, $C_1$–$C_6$-alkyl, $C_1$–$C_6$-haloalkyl, $C_1$–$C_6$-alkoxy-$C_1$–$C_6$-alkyl, $C_2$–$C_6$-alkenyl, $C_2$–$C_6$-alkynyl, —$OR^3$, —$OCOR^3$, —$OSO_2R^3$, —$S(O)_nR^3$, —$SO_2OR^3$, —$SO_2N(R^3)_2$, —$NR^3SO_2R^3$ or —$NR^3COR^3$;

$R^3$ is hydrogen, $C_1$–$C_6$-alkyl, $C_1$–$C_6$-haloalkyl, $C_2$–$C_6$-alkenyl, $C_2$–$C_6$-alkynyl, phenyl or phenyl-$C_1$–$C_6$-alkyl; where the abovementioned alkyl radicals may be partially or fully halogenated and/or may carry one to three of the following groups:

hydroxyl, mercapto, amino, cyano, $R^3$, —$OR^3$, —$SR^3$, —$N(R^3)_2$, =$NOR^3$, —$OCOR^3$, —$SCOR^3$, —$NR^3COR^3$, —$CO_2R^3$, —$COSR^3$, —$CON(R^3)_2$, $C_1$–$C_4$-alkyliminooxy, $C_1$–$C_4$-alkoxyamino, $C_1$–$C_4$-alkylcarbonyl, $C_1$–$C_4$-alkoxy-$C_2$–$C_6$-alkoxycarbonyl, $C_1$–$C_4$-alkylsulfonyl, heterocyclyl, heterocyclyloxy, phenyl, benzyl, hetaryl, phenoxy, benzyloxy and hetaryloxy, where the eight last-mentioned radicals may in turn be substituted;

n is 0, 1 or 2;
Q is a pyrazole of the formula II

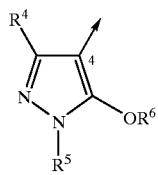

which is attached in position 4 and where
$R^4$ is hydrogen, $C_1$–$C_6$-alkyl or $C_1$–$C_6$-haloalkyl;
$R^5$ is $C_1$–$C_6$-alkyl, $C_1$–$C_6$-haloalkyl, phenyl or phenyl which may be partially or fully halogenated and/or may carry one to three of the following radicals:
nitro, cyano, $C_1$–$C_4$-alkyl, $C_1$–$C_4$-haloalkyl, $C_1$–$C_4$-alkoxy, $C_1$–$C_4$-haloalkoxy;
$R^6$ is hydrogen, $C_1$–$C_6$-alkyl, $C_1$–$C_6$-haloalkyl, $C_1$–$C_6$-alkylcarbonyl, $C_1$–$C_6$-haloalkylcarbonyl, $C_1$–$C_6$-alkoxycarbonyl, $C_1$–$C_6$-alkylsulfonyl, $C_1$–$C_6$-haloalkylsulfonyl, phenylcarbonyl, phenylcarbonylmethyl, phenoxycarbonyl or phenylsulfonyl,
where the four last-mentioned substituents are unsubstituted, or the phenyl ring in question may be partially or fully halogenated and/or may carry one to three of the following radicals:
nitro, cyano, $C_1$–$C_4$-alkyl, $C_1$–$C_4$-haloalkyl, $C_1$–$C_4$-alkoxy, $C_1$–$C_4$-haloalkoxy;

$X^1$ is a straight-chain or branched $C_1$–$C_6$-alkylene, a $C_2$–$C_6$-alkenylene or a $C_2$–$C_6$-alkynylene chain which is interrupted by a hetero atom selected from the group consisting of:
oxygen and sulfur,
where the abovementioned alkylene, alkenylene or alkynylene radicals may be partially halogenated and/or may carry one to three of the following groups:
—$OR^7$, —$OCOR^7$, —$OCONHR^7$ or —$OSO_2R^7$;

$R^7$ is hydrogen, $C_1$–$C_6$-alkyl, $C_2$–$C_6$-alkenyl, $C_2$–$C_6$-alkynyl, phenyl, phenyl-$C_1$–$C_6$-alkyl, where the abovementioned alkyl, alkenyl or alkynyl radicals may be partially or fully halogenated and/or may be substituted by one or more of the following radicals:
hydroxyl, mercapto, amino, cyano, nitro, formyl, $C_1$–$C_4$-alkylamino, $C_1$–$C_4$-dialkylamino, $C_1$–$C_4$-alkoxycarbonyl, $C_1$–$C_4$-alkylcarbonyl, $C_1$–$C_4$-alkylcarbonyloxy, $C_1$–$C_4$-alkyl, $C_1$–$C_4$-haloalkyl, $C_1$–$C_4$-alkylthio, $C_1$–$C_4$-haloalkylthio, $C_1$–$C_4$-alkoxy, $C_1$–$C_4$-haloalkoxy;

Het is a three- to six-membered partially or fully saturated heterocyclic group or a three- to six-membered heteroaromatic group having up to three hetero atoms selected from the following three groups:
nitrogen,
oxygen in combination with at least one nitrogen or sulfur in combination with at least one nitrogen,
where the abovementioned heterocyclic or heteroaromatic group may be partially or fully halogenated and/or may be substituted by $R^8$;

$R^8$ is hydrogen, hydroxyl, mercapto, amino, cyano, nitro, formyl, $C_1$–$C_4$-alkylamino, $C_1$–$C_4$-dialkylamino, $C_1$–$C_4$-alkoxycarbonyl, $C_1$–$C_4$-alkylcarbonyl, $C_1$–$C_4$-alkylcarbonyloxy, $C_1$–$C_4$-alkyl, $C_1$–$C_4$-haloalkyl, $C_1$–$C_4$-alkylthio, $C_1$–$C_4$-haloalkylthio, $C_1$–$C_4$-alkoxy, $C_1$–$C_4$-haloalkoxy, where the alkyl radicals may in each case be substituted by in each case one or more of the following radicals:
cyano, formyl, $C_1$–$C_4$-alkylamino, $C_1$–$C_4$-dialkylamino, $C_1$–$C_4$-alkoxycarbonyl, $C_1$–$C_4$-alkylcarbonyl, $C_1$–$C_4$-alkylcarbonyloxy, $C_1$–$C_4$-alkyl, $C_1$–$C_4$-haloalkyl, $C_1$–$C_4$-alkylthio, $C_1$–$C_4$-haloalkylthio, $C_1$–$C_4$-alkoxy, $C_1$–$C_4$-haloalkoxy;
and agriculturally useful salts thereof.

In addition, the invention relates to processes and intermediates for preparing compounds of the formula I, to compositions comprising them, and to the use of the compounds of the formula I and of compositions comprising them for controlling harmful plants.

4-Benzoylpyrazoles are disclosed in the literature, for example in EP-A 282 944.

However, the herbicidal properties of the prior art compounds and their crop plant safety are not entirely satisfactory.

It is an object of the present invention to provide novel, in particular herbicidally active, compounds having improved properties.

We have found this object is achieved by the 4-benzoylpyrazoles of the formula I according to the invention and their herbicidal activity.

Furthermore, we have found herbicidal compositions which comprise the compounds I and have very good herbicidal activity. Moreover, we have found processes for preparing these compositions and methods for controlling undesirable vegetation using the compounds I.

The present invention also provides stereoisomers of the compounds of the formula I. Pure stereoisomers and also mixtures thereof are included.

Depending on the substitution pattern, the compounds of the formula I may contain one or more chiral centers and, if this is the case, are present as enantiomers or mixtures of diastereomers. The invention provides the pure enantiomers or diastereomers and also mixtures thereof.

The compounds of the formula I may also be present in the form of their agriculturally useful salts, the kind of salt generally not being important. The salts of those cations or the acid addition salts of those acids whose cations or anions, respectively, do not adversely affect the herbicidal activity of the compounds I are generally suitable.

Suitable cations are in particular ions of the alkali metals, preferably lithium, sodium and potassium, of the alkaline earth metals, preferably calcium and magnesium, and of the transition metals, preferably manganese, copper, zinc and iron, and ammonium, where, if desired, one to four hydrogen atoms may be replaced by $C_1$–$C_4$-alkyl or hydroxyl-$C_1$–$C_4$-alkyl and/or one phenyl or benzyl, preferably diisopropylammonium, tetramethylammonium, tetrabutylammonium, trimethylbenzylammonium, furthermore phosphonium ions, sulfonium ions, preferably tri($C_1$–$C_4$-alkyl)sulfonium and sulfoxonium ions, preferably tri($C_1$–$C_4$-alkyl)sulfoxonium.

Anions of useable acid addition salts are primarily chloride, bromide, fluoride, hydrogen sulfate, sulfate, dihydrogen phosphate, hydrogen phosphate, nitrate, hydrogen carbonate, carbonate, hexafluorosilicate, hexafluorophosphate, benzoate and the anions of $C_1$–$C_4$-alkanoic acids, preferably formate, acetate, propionate and butyrate.

Process A:

Reactions of pyrazoles of the formula II (where $R^6$=H) with an activated carboxylic acid IIIa or a carboxylic acid IIIb, which is preferably activated in situ, to give the acylation product V, and subsequent rearrangements to the compounds of the formula Ia according to the invention.

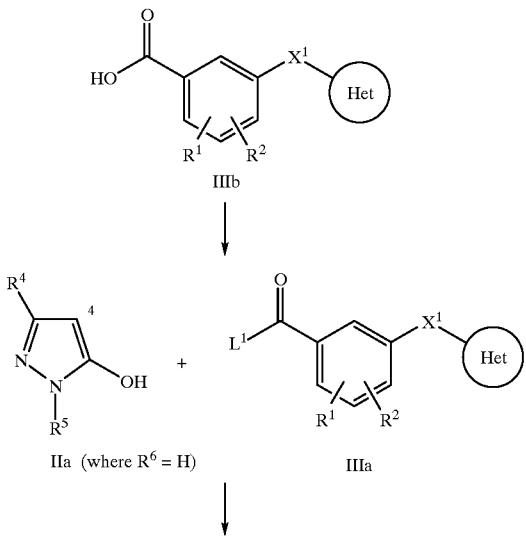

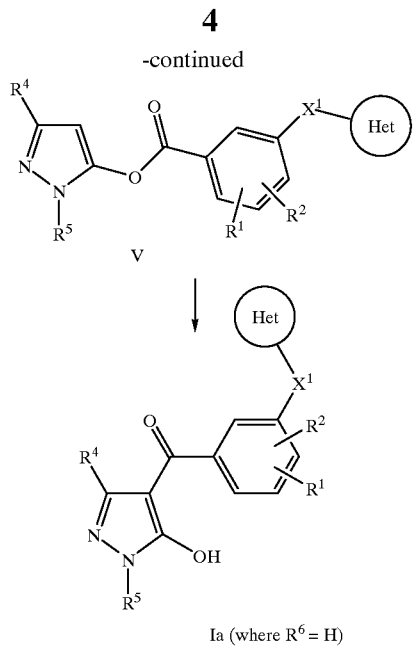

Ia (where $R^6$ = H)

$L^1$ is a nucleophilically replaceable leaving group such as halogen, for example bromine or chlorine, hetaryl, for example imidazolyl or pyridyl, or carboxylate, for example acetate, trifluoroacetate, etc.

The activated carboxylic acid can be employed directly, as in the case of the acyl halides, or be generated in situ, for example by using dicyclohexylcarbodiimide, triphenylphosphine/azodicarboxylic esters, 2-pyridine disulfite/triphenylphosphine, carbonyldiimidazole, etc.

It may be advantageous to carry out the acylation reaction in the presence of a base. The starting materials and the auxiliary base are advantageously employed in equimolar amounts. A slight excess of auxiliary base, for example 1.2 to 1.5 molar equivalents, based on II, may be advantageous under certain circumstances.

Suitable auxiliary bases are tertiary alkylamines, pyridine or alkali metal carbonates. Examples of solvents which can be used are chlorinated hydrocarbons, such as methylene chloride, 1,2-dichloroethane, aromatic hydrocarbons, such as toluene, xylene, chlorobenzene, ethers, such as diethyl ether, methyl tert-butyl ether, tetrahydrofuran, dioxane, polar aprotic solvents, such as acetonitrile, dimethylformamide, dimethyl sulfoxide, or esters such as ethyl acetate or mixtures of these.

If acyl halides are employed as activated carboxylic acid component, it may be advantageous to cool the reaction mixture to 0–10° C. when adding this reaction partner. The mixture is subsequently stirred at 20–100° C., preferably at 25–50° C., until the reaction is complete. Work-up is carried out in the customary manner, for example by pouring the reaction mixture into water and extracting the product of value. Solvents which are particularly suitable for this purpose are methylene chloride, diethyl ether and ethyl acetate. After the organic phase has been dried and the solvent has been removed, the crude enol ester of the formula V is purified, preferably by chromatography. Alternatively, it is possible to employ the crude enol ester of the formula V without further purification for the rearrangement reaction.

The rearrangement of the enol esters of the formula V to the compounds of the formula I is advantageously carried out at from 20 to 40° C. in a solvent and in the presence of a base and, if appropriate, in the presence of a cyano compound.

Examples of solvents which can be used are acetonitrile, methylene chloride, 1,2-dichloroethane, dioxane, ethyl acetate, toluene or mixtures of these. Preferred solvents are acetonitrile and dioxane.

Suitable bases are tertiary amines such as triethylamine, pyridine or alkali metal carbonates, such as sodium carbonate, potassium carbonate, which are preferably employed in equimolar amounts or up to a four-fold excess, based on the ester. Preference is given to using triethylamine or alkali metal carbonates.

Suitable cyano compounds are inorganic cyanides such as sodium cyanide, potassium cyanide and organic cyano compounds such as acetone cyanohydrin, trimethylsilyl cyanide. They are employed in an amount of 1 to 50 mol percent, based on the ester. Preference is given to using acetone cyanohydrin or trimethylsilyl cyanide, for example, in an amount of 5 to 15, preferably 10, mol percent, based on the ester.

Particular preference is given to employing alkali metal carbonates, such as potassium carbonate, in acetonitrile or dioxane.

Work-up can be carried out in a manner known per se. For example, the reaction mixture is acidified with dilute mineral acid, such as 5% strength hydrochloric acid or sulfuric acid, and extracted with an organic solvent, for example methylene chloride, ethyl acetate. The organic phase can be extracted with 5–10% strength alkali metal carbonate solution, for example sodium carbonate or potassium carbonate solution. The aqueous phase is acidified, and the precipitate which forms is filtered off with suction and/or extracted with methylene chloride or ethyl acetate, dried and concentrated.

(Examples of the synthesis of esters from hydroxypyrazoles and the rearrangement of the esters are mentioned for example in EP-A 282 944 or U.S. Pat No. 4, 643, 757).

The pyrazoles of the formula II (where $R^6$=H) used as starting materials are known or can be prepared by methods known per se (for example EP-A 240 001, J. Prakt. Chem. 315 (1973), 383).

Process B:

Reactions of 4-benzoylpyrazoles of the formula Ia with a compound of the formula IV (where $R^6 \neq H$):

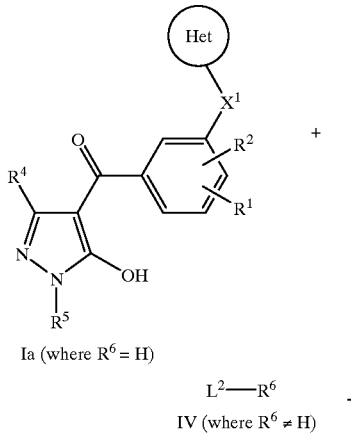

Ia (where $R^6$ = H)

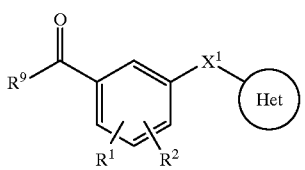

IV (where $R^6 \neq H$)

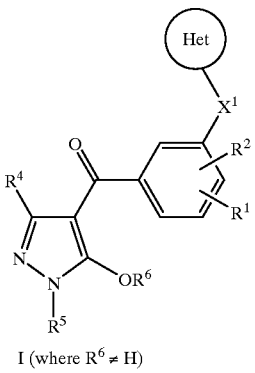

I (where $R^6 \neq H$)

$L^2$ is a nucleophilically replaceable leaving group such as halogen, for example bromine or chlorine, hetaryl, for example imidazolyl or pyridyl, carboxylate, for example acetate or trifluoroacetate, sulfonate, for example mesylate, triflate, etc.

The compounds of the formula IV can be employed directly, for example in the case of the alkyl halides, acyl halides, sulfonyl halides, carboxylic anhydrides and sulfonic anhydrides, or prepared in situ, for example activated carboxylic acids (by means of carboxylic acid and dicyclohexylcarbodiimide, carbonyldiimidazole, etc.).

In general, the starting materials are employed in an equimolar ratio. However, it may also be advantageous to employ an excess of one or the other component.

Where appropriate, it may be advantageous to carry out the reaction in the presence of a base. The starting materials and the auxiliary base are advantageously employed in equimolar amounts. Under certain circumstances, it may be advantageous to employ an excess of the auxiliary base, for example 1.5 to 3 molar equivalents, based on Ia.

Suitable auxiliary bases are tertiary alkylamines such as triethylamine, pyridine, alkali metal carbonates, for example sodium carbonate, potassium carbonate, and alkali metal hydrides, for example sodium hydride. Preference is given to using triethylamine, pyridine and potassium carbonate.

Examples of suitable solvents are chlorinated hydrocarbons such as methylene chloride, 1,2-dichloroethane, aromatic hydrocarbons, for example toluene, xylene, chlorobenzene, ethers, such as diethyl ether, methyl tert-butyl ether, tetrahydrofuran, dioxane, polar aprotic solvents, such as acetonitrile, dimethylformamide, dimethyl sulfoxide or esters, such as ethyl acetate, or mixtures of these.

The reaction temperature is generally in the range of from 0° C. to the boiling point of the reaction mixture.

Work-up can be carried out in a manner known per se.

The benzoic acids of the formula III are novel,

III where:

$R^1$ and $R^2$ are each hydrogen, mercapto, nitro, halogen, cyano, thiocyanato, $C_1$–$C_6$-alkyl, $C_1$–$C_6$-haloalkyl, $C_1$–$C_6$-alkoxy-$C_1$–$C_6$-alkyl, $C_2$–$C_6$-alkenyl, $C_2$–$C_6$-alkynyl, —$OR^3$, —$OCOR^3$, —$OSO_2R^3$, —$S(O)_nR^3$, —SO$_2$OR$^3$, —SO$_2$N(R$^3$)$_2$, —NR$^3$SO$_2$R$^3$ or —NR$^3$COR$^3$;

n is 0, 1 or 2;

R$^3$ is hydrogen, C$_1$–C$_6$-alkyl, C$_1$–C$_6$-haloalkyl, C$_2$–C$_6$-alkenyl, C$_2$–C$_6$-alkynyl, phenyl or phenyl-C$_1$–C$_6$-alkyl; where the abovementioned alkyl radicals may be partially or fully halogenated and/or may carry one to three of the following groups:

hydroxyl, mercapto, amino, cyano, R$^3$, —OR$^3$, —SR$^3$, —N(R$^3$)$_2$, =NOR$^3$, —OCOR$^3$, —SCOR$^3$, —NR$^3$COR$^3$, —CO$_2$R$^3$, —COSR$^3$, —CON(R$^3$)$_2$, C$_1$–C$_4$-alkyliminooxy, C$_1$–C$_4$-alkoxyamino, C$_1$–C$_4$-alkylcarbonyl, C$_1$–C$_4$-alkoxy-C$_2$–C$_6$-alkoxycarbonyl, C$_1$–C$_4$-alkylsulfonyl, heterocyclyl, heterocyclyloxy, phenyl, benzyl, hetaryl, phenoxy, benzyloxy and hetaryloxy, where the eight last-mentioned radicals may in turn be substituted;

X$^1$ is a straight-chain or branched C$_1$–C$_6$-alkylene, a C$_2$–C$_6$-alkenylene or a C$_2$–C$_6$-alkynylene chain which is interrupted by a hetero atom selected from the group consisting of:

oxygen and sulfur, where the abovementioned alkylene, alkenylene or alkynylene radicals may be partially halogenated and/or may carry one to three of the following groups:

—OR$^7$, —OCOR$^7$, —OCONHR$^7$ or —OSO$_2$R$^7$;

R$^7$ is hydrogen, C$_1$–C$_6$-alkyl, C$_2$–C$_6$-alkenyl, C$_2$–C$_6$-alkynyl, phenyl, phenyl-C$_1$–C$_6$-alkyl, where the abovementioned alkyl, alkenyl or alkynyl radicals may be partially or fully halogenated and/or may be substituted by one or more of the following radicals:

hydroxyl, mercapto, amino, cyano, nitro, formyl, C$_1$–C$_4$-alkylamino, C$_1$–C$_4$-dialkylamino, C$_1$–C$_4$-alkoxycarbonyl, C$_1$–C$_4$-alkylcarbonyl, C$_1$–C$_4$-alkylcarbonyloxy, C$_1$–C$_4$-alkyl, C$_1$–C$_4$-haloalkyl, C$_1$–C$_4$-alkylthio, C$_1$–C$_4$-haloalkylthio, C$_1$–C$_4$-alkoxy, C$_1$–C$_4$-haloalkoxy;

Het is a three- to six-membered partially or fully saturated heterocyclic group or a three- to six-membered heteroaromatic group having up to three hetero atoms selected from the following three groups:

nitrogen, oxygen in combination with at least one nitrogen or sulfur in combination with at least one nitrogen, where the abovementioned heterocyclic or heteroaromatic group may be partially or fully halogenated and/or may be substituted by R$^8$;

R$^8$ is hydrogen, hydroxyl, mercapto, amino, cyano, nitro, formyl, C$_1$–C$_4$-alkylamino, C$_1$–C$_4$-dialkylamino, C$_1$–C$_4$-alkoxycarbonyl, C$_1$–C$_4$-alkylcarbonyl, C$_1$–C$_4$-alkylcarbonyloxy, C$_1$–C$_4$-alkyl, C$_1$–C$_4$-haloalkyl, C$_1$–C$_4$-alkylthio, C$_1$–C$_4$-haloalkylthio, C$_1$–C$_4$-alkoxy, C$_1$–C$_4$-haloalkoxy, where the alkyl radicals may in each case be substituted by in each case one or more of the following radicals:

cyano, formyl, C$_1$–C$_4$-alkylamino, C$_1$–C$_4$-dialkylamino, C$_1$–C$_4$-alkoxycarbonyl, C$_1$–C$_4$-alkylcarbonyl, C$_1$–C$_4$-alkylcarbonyloxy, C$_1$–C$_4$-alkyl, C$_1$–C$_4$-haloalkyl, C$_1$–C$_4$-alkylthio, C$_1$–C$_4$-haloalkylthio, C$_1$–C$_4$-alkoxy, C$_1$–C$_4$-haloalkoxy;

R$^9$ is hydroxyl or a hydrolyzable radical.

Examples of hydrolyzable radicals are alkoxy, phenoxy, alkylthio and phenylthio radicals which can be substituted, halides, hetaryl radicals which are bonded via nitrogen, amino and imino radicals which can be substituted, etc.

Preference is given to benzoyl halides IIIa where L$^1$=halogen ($\hat{=}$ III where R$^9$=halogen),

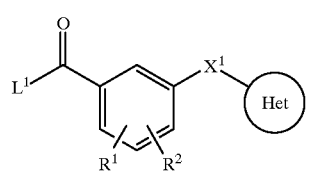

IIIa where the variables R$^1$, R$^2$, X$^1$ and Het are each as defined under formula III and L$^1$ is halogen, in particular chlorine or bromine.

Preference is also given to benzoic acids of the formula IIIb ($\hat{=}$ III where R$^9$=hydroxyl),

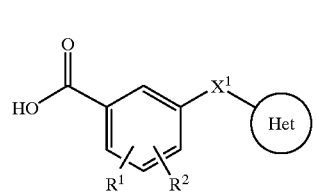

IIIb where the variables R$^1$, R$^2$, X$^1$ and Het are each as defined under formula III.

Preference is also given to benzoic esters of the formula IIIc ($\hat{=}$ III where R$^9$=C$_1$–C$_6$-alkoxy),

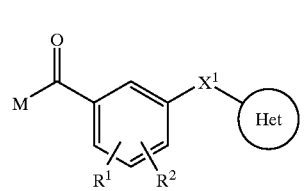

IIIc where the variables R$^1$, R$^2$, X$^1$ and Het are each as defined under formula III and M is C$_1$–C$_6$-alkoxy.

The compounds of the formula IIIa (where L$^1$=halogen) can be synthesized by methods similar to those known from the literature (cf. L. G. Fieser, M. Fieser "Reagents for Organic Synthesis", Vol. I, pp. 767–769 (1967)) by reacting benzoic acids of the formula IIIb with halogenating agents such as thionyl chloride, thionyl bromide, phosgene, diphosgene, triphosgene, oxalyl chloride and oxalyl bromide.

The benzoic acids of the formula IIIb can be obtained, inter alia, by hydrolyzing the benzoic esters of the formula IIIc (where M=C$_1$–C$_6$-alkoxy).

The benzoic esters of the formula IIIc according to the invention can be synthesized by various methods known from the literature (for example a: G. Dittus in Houben-Weyl, Methoden der Organischen Chemie, Volume VI/3, Oxygen Compounds I, 4th Edition, 1965, p. 493 ff., Georg Thieme Verlag; b: T. L. Gilchrist, Heterocyclenchemie, 2nd Edition, Verlag Chemie, 1995), as illustrated in the examples that follow.

Process C:

Substitution of the benzoic esters VIa with suitable nucleophiles VII gives the benzoic esters IIIc according to the invention,

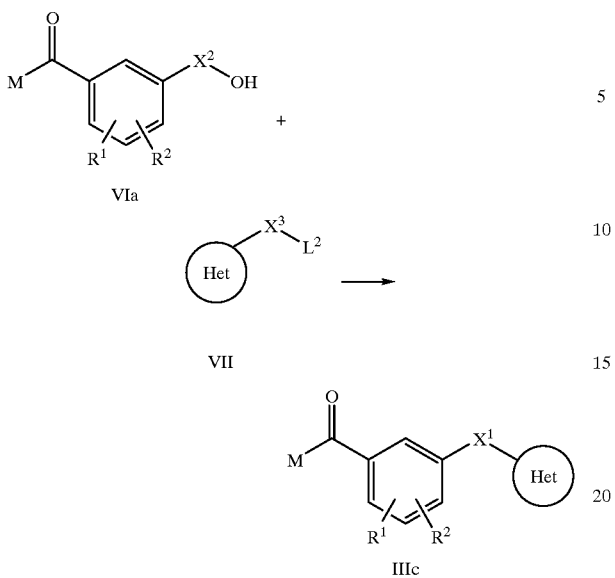

VIa

VII

IIIc where M, $R^1$ and $R^2$ are each as defined above, $L^2$ is a suitable nucleophilically replaceable leaving group such as halogen, for example bromine or chlorine, hetaryl, for example imidazolyl or pyridyl, carboxylate, for example acetate or trifluoroacetate, sulfonate, for example mesylate, triflate, etc.

$X^2$ is a straight-chain or branched alkylene, an alkenylene or an alkynylene chain having at least one and a maximum of five carbon atoms, where the abovementioned alkylene, alkenylene or alkynylene radicals may be partially halogenated and/or may carry one to three of the following groups:
—$OR^7$, —$OCOR^7$, —$OCONHR^7$ or —$OSO_2R^7$ and $X^3$ is a straight-chain or branched alkylene, an alkenylene or an alkynylene chain having a maximum of five carbon atoms, where the abovementioned alkylene, alkenylene or alkynylene radicals may be partially halogenated and/or may carry one to three of the following groups:
—$OR^7$, —$OCOR^7$, —$OCONHR^7$ or —$OSO_2R^7$.

The starting materials are usually employed in equimolar amounts. However, it may be advantageous to employ one or the other component in excess.

If appropriate, it may be advantageous to carry out the reaction in the presence of a base. The starting materials and the auxiliary base are advantageously employed in equimolar amounts. In certain cases, an excess of the auxiliary base, for example 1.5 to 3 molar equivalents, based on VIa, may be advantageous.

Suitable auxiliary bases are tertiary alkylamines such as triethylamine, pyridine, alkali metal carbonates, for example sodium carbonate or potassium carbonate, and alkali metal hydrides, for example sodium hydride. Preference is given to using triethylamine, pyridine and potassium carbonate.

Suitable solvents are, for example, chlorinated hydrocarbons such as methylene chloride or 1,2-dichloroethane, aromatic hydrocarbons, for example toluene, xylene, chlorobenzene, ethers such as diethyl ether, methyl tert-butyl ether, tetrahydrofuran, dioxane, polar aprotic solvents such as acetonitrile, dimethylformamide, dimethyl sulfoxide, or esters such as ethyl acetate, or mixtures of these.

The reaction temperature is generally in the range from 0° C. to the boiling point of the reaction mixture.

Work-up can be carried out in a manner known per se.

Process D:

Substitution of suitably substituted heterocycles VIII with benzoic esters Vb gives the benzoic esters IIIc according to the invention,

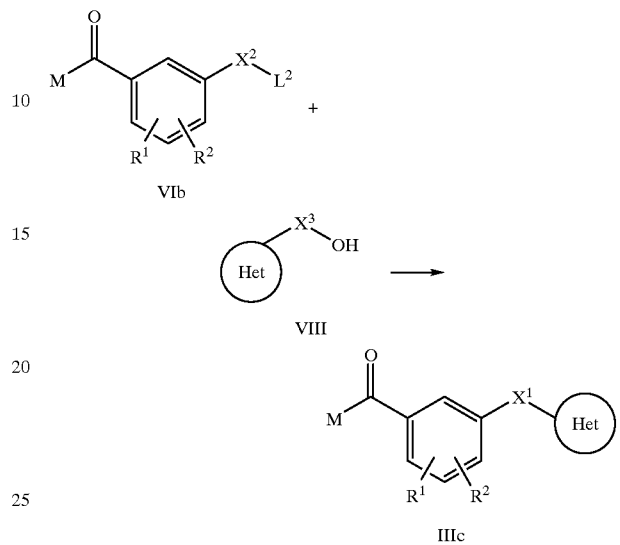

VIb

VIII

IIIc where M, $R^1$ and $R^2$ are each as defined above, $L^2$ is a suitable nucleophilically replaceable leaving group such as halogen, for example bromine or chlorine, hetaryl, for example imidazolyl or pyridyl, carboxylate, for example acetate or trifluoroacetate, sulfonate, for example mesylate, triflate, etc.

$X^2$ is a straight-chain or branched alkylene, an alkenylene or an alkynylene chain having at least one and a maximum of five carbon atoms, where the abovementioned alkylene, alkenylene or alkynylene radicals may be partially halogenated and/or may carry one to three of the following groups:
—$OR^7$, —$OCOR^7$, —$OCONHR^7$ or —$OSO_2R^7$ and $X^3$ is a straight-chain or branched alkylene, an alkenylene or an alkynylene chain having a maximum of five carbon atoms, where the abovementioned alkylene, alkenylene or alkynylene radicals may be partially halogenated and/or may carry one to three of the following groups:
—$OR^7$, —$OCOR^7$, —$OCONHR^7$ or —$OSO_2R^7$.

The starting materials are usually employed in equimolar amounts. However, it may be advantageous to employ one or the other component in excess.

If appropriate, it may be advantageous to carry out the reaction in the presence of a base. The starting materials and the auxiliary base are advantageously employed in equimolar amounts. In certain cases, an excess of the auxiliary base, for example 1.5 to 3 molar equivalents, based on VIII, may be advantageous.

Suitable auxiliary bases are tertiary alkylamines such as triethylamine, pyridine, alkali metal carbonates, for example sodium carbonate or potassium carbonate, and alkali metal hydrides, for example sodium hydride. Preference is given to using triethylamine, pyridine and potassium carbonate.

Suitable solvents are, for example, chlorinated hydrocarbons such as methylene chloride or 1,2-dichloroethane, aromatic hydrocarbons, for example toluene, xylene, chlorobenzene, ethers such as diethyl ether, methyl tert-butyl ether, tetrahydrofuran, dioxane, polar aprotic solvents such as acetonitrile, dimethylformamide, dimethyl sulfoxide, or esters such as ethyl acetate, or mixtures of these.

The reaction temperature is generally in the range from 0° C. to the boiling point of the reaction mixture.

Work-up can be carried out in a manner known per se.

Emphasis is to be given to compounds of the formula I according to the invention where the group $X^1$ is a $C_1$–$C_3$-alkylene, a $C_2$–$C_3$-alkenylene or $C_2$–$C_3$-alkynylene chain which is interrupted by an oxygen atom and Het is a three- to six-membered partially or fully saturated heterocyclic group or a three- to six-membered heteroaromatic group having up to three hetero atoms selected from the following three groups:
nitrogen,
oxygen in combination with at least one nitrogen or sulfur in combination with at least one nitrogen,
where the abovementioned heterocyclic or heteroaromatic group may be partially or fully halogenated and/or may be substituted by $R^8$.

Furthermore, emphasis is to be given to the compounds of the formula I according to the invention where the group Het is a five- or six-membered partially or fully saturated heterocyclic or a five- or six-membered heteroaromatic group having up to three hetero atoms selected from the following three groups:
nitrogen,
oxygen in combination with at least one nitrogen or sulfur in combination with at least one nitrogen;
where the abovementioned heterocyclic or heteroaromatic group may be partially or fully halogenated and/or substituted by RB;

$R^8$ is hydrogen, hydroxyl, mercapto, amino, cyano, nitro, formyl, $C_1$–$C_4$-alkylamino, $C_1$–$C_4$-dialkylamino, $C_1$–$C_4$-alkoxycarbonyl, $C_1$–$C_4$-alkylcarbonyl, $C_1$–$C_4$-alkylcarbonyloxy, $C_1$–$C_4$-alkyl, $C_1$–$C_4$-haloalkyl, $C_1$–$C_4$-alkylthio, $C_1$–$C_4$-haloalkylthio, $C_1$–$C_4$-alkoxy, $C_1$–$C_4$-haloalkoxy, where the alkyl radicals may in each case be substituted by in each case one or more of the following radicals:
cyano, formyl, $C_1$–$C_4$-alkylamino, $C_1$–$C_4$-dialkylamino, $C_1$–$C_4$-alkoxycarbonyl, $C_1$–$C_4$-alkylcarbonyl, $C_1$–$C_4$-alkylcarbonyloxy, $C_1$–$C_4$-alkyl, $C_1$–$C_4$-haloalkyl, $C_1$–$C_4$-alkylthio, $C_1$–$C_4$-haloalkylthio, $C_1$–$C_4$-alkoxy, $C_1$–$C_4$-haloalkoxy.

The organic moieties mentioned for the substituents $R^1$–$R^9$ or as radicals on phenyl, hetaryl and heterocyclyl rings are collective terms for individual enumerations of the individual group members. All hydrocarbon chains, ie. all alkyl, haloalkyl, cycloalkyl, alkoxyalkyl, alkoxy, haloalkoxy, alkyliminooxy, alkoxyamino, alkylsulfonyl, haloalkylsulfonyl, alkylcarbonyl, haloalkylcarbonyl, alkoxycarbonyl, alkoxyalkoxycarbonyl, alkenyl, cycloalkenyl, alkynyl moieties can be straight-chain or branched. Unless otherwise specified, halogenated substituents preferably carry one to five identical or different halogen atoms, the meaning of halogen being in each case fluorine, chlorine, bromine or iodine.

Examples of other meanings are:

$C_1$–$C_4$-alkyl, and the alkyl moieties of $C_1$–$C_4$-alkylcarbonyl: methyl, ethyl, n-propyl, 1-methylethyl, butyl, 1-methylpropyl, 2-methylpropyl and 1,1-dimethylethyl;

$C_1$–$C_6$-alkyl and the alkyl moieties of $C_1$–$C_6$-alkoxy-$C_1$–$C_6$-alkyl and $C_1$–$C_6$-alkylcarbonyl: $C_1$–$C_4$-alkyl as mentioned above, and also pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1-ethyl-1-methylpropyl and 1-ethyl-3-methylpropyl;

$C_1$–$C_4$-haloalkyl: a $C_1$–$C_4$-alkyl radical as mentioned above which is partially or fully substituted by fluorine, chlorine, bromine and/or iodine, eg. chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl and nonafluorobutyl;

$C_1$–$C_6$-haloalkyl and the haloalkyl moieties of $C_1$–$C_6$-haloalkylcarbonyl: $C_1$–$C_4$-haloalkyl as mentioned above, and also 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl and dodecafluorohexyl;

$C_1$–$C_4$-alkoxy and the alkoxy moieties of $C_1$–$C_4$-alkoxyamino, $C_1$–$C_4$-alkoxy-$C_2$–$C_6$-alkoxycarbonyl and $C_1$–$C_4$-alkoxycarbonyl: methoxy, ethoxy, propoxy, 1-methylethoxy, butoxy, 1-methylpropoxy, 2-methylpropoxy and 1,1-dimethylethoxy;

$C_1$–$C_6$-alkoxy and the alkoxy moieties of $C_1$–$C_6$-alkoxy-$C_1$–$C_6$-alkyl, $C_1$–$C_6$-alkoxy-$C_2$–$C_6$-alkyl, $C_1$–$C_4$-alkoxy-$C_2$–$C_6$-alkoxycarbonyl and $C_1$–$C_6$-alkoxycarbonyl: $C_1$–$C_4$-alkoxy as mentioned above, and also pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy;

$C_1$–$C_4$-haloalkoxy: a $C_1$–$C_4$-alkoxy radical as mentioned above which is partially or fully substituted by fluorine, chlorine, bromine and/or iodine, eg. fluoromethoxy, difluoromethoxy, trifluoromethoxy, chlorodifluoromethoxy, bromodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3- dichloropropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy and nonafluorobutoxy;

$C_1$–$C_4$-alkylsulfonyl ($C_1$–$C_4$-alkyl-S(=O)$_2$—): methylsulfonyl, ethylsulfonyl, propylsulfonyl, 1-methylethylsulfonyl, butylsulfonyl, 1-methylpropylsulfonyl, 2-methylpropylsulfonyl and 1,1-dimethylethylsulfonyl;

$C_1$–$C_6$-alkylsulfonyl: $C_1$–$C_4$-alkylsulfonyl as mentioned above, and also pentylsulfonyl, 1-methylbutylsulfonyl, 2-methylbutylsulfonyl, 3-methylbutylsulfonyl, 2,2-dimethylpropylsulfonyl, 1-ethylpropylsulfonyl, 1,1-dimethylpropylsulfonyl, 1,2-dimethylpropylsulfonyl, hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl and 1-ethyl-2-methylpropylsulfonyl;

$C_1$–$C_6$-haloalkylsulfonyl: a $C_1$–$C_6$-alkylsulfonyl radical as mentioned above which is partially or fully substituted by fluorine, chlorine, bromine and/or iodine, ie. fluoromethylsulfonyl, difluoromethylsulfonyl, trifluoromethylsulfonyl, chlorodifluoromethylsulfonyl, bromodifluoromethylsulfonyl, 2-fluoroethylsulfonyl, 2-chloroethylsulfonyl, 2-bromoethylsulfonyl, 2-iodoethylsulfonyl, 2,2-difluoroethylsulfonyl, 2,2,2-trifluoroethylsulfonyl, 2,2,2-trichloroethylsulfonyl, 2-chloro-2-fluoroethylsulfonyl, 2-chloro-2,2-difluoroethylsulfonyl, 2,2-dichloro-2-fluoroethylsulfonyl, pentafluoroethylsulfonyl, 2-fluoropropylsulfonyl, 3-fluoropropylsulfonyl, 2-chloropropylsulfonyl, 3-chloropropylsulfonyl, 2-bromopropylsulfonyl, 3-bromopropylsulfonyl, 2,2-difluoropropylsulfonyl, 2,3-difluoropropylsulfonyl, 2,3-dichloropropylsulfonyl, 3,3,3-trifluoropropylsulfonyl, 3,3,3-trichloropropylsulfonyl, 2,2,3,3,3-pentafluoropropylsulfonyl, heptafluoropropylsulfonyl, 1-(fluoromethyl)-2-fluoroethylsulfonyl, 1-(choromethyl)-2-chloroethylsulfonyl, 1-(bromomethyl)-2-bromoethylsulfonyl, 4-fluorobutylsulfonyl, 4-chlorobutylsulfonyl, 4-bromobutylsulfonyl, nonafluorobutylsulfonyl, 5-fluoropentylsulfonyl, 5-chloropentylsulfonyl, 5-bromopentylsulfonyl, 5-iodopentylsulfonyl, 6-fluorohexylsulfonyl, 6-bromohexylsulfonyl, 6-iodohexylsulfonyl and dodecafluorohexylsulfonyl;

$C_1$–$C_4$-alkyliminooxy: methyliminooxy, ethyliminooxy, 1-propyliminooxy, 2-propyliminooxy, 1-butyliminooxy and 2-butyliminooxy;

$C_3$–$C_6$-alkenyl: prop-1-en-1-yl, prop-2-en-1-yl, 1-methylethenyl, buten-1-yl, buten-2-yl, buten-3-yl, 1-methylprop-1-en-1-yl, 2-methylprop-1-en-1-yl, 1-methylprop-2-en-1-yl, 2-methylprop-2-en-1-yl, penten-1-yl, penten-2-yl, penten-3-yl, penten-4-yl, 1-methylbut-1-en-1-yl, 2-methylbut-1-en-1-yl, 3-methylbut-1-en-1-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-1-en-1-yl, 1,2-dimethylprop-2-en-1-yl, 1-ethylprop-1-en-2-yl, 1-ethylprop-2-en-1-yl, hex-1-en-1-yl, hex-2-en-1-yl, hex-3-en-1-yl, hex-4-en-1-yl, hex-5-en-1-yl, 1-methylpent-1-en-1-yl, 2-methylpent-1-en-1-yl, 3-methylpent-1-en-1-yl, 4-methylpent-1-en-1-yl, 1-methylpent-2-en-1-yl, 2-methylpent-2-en-1-yl, 3-methylpent-2-en-1-yl, 4-methylpent-2-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-1-en-1-yl, 1,2-dimethylbut-2-en-1-yl, 1,2-dimethylbut-3-en-1-yl, 1,3-dimethylbut-1-en-1-yl, 1,3-dimethylbut-2-en-1-yl, 1,3-dimethylbut-3-en-1-yl, 2,2-dimethylbut-3-en-1-yl, 2,3-dimethylbut-1-en-1-yl, 2,3-dimethylbut-2-en-1-yl, 2,3-dimethylbut-3-en-1-yl, 3,3-dimethylbut-1-en-1-yl, 3,3-dimethylbut-2-en-1-yl, 1-ethylbut-1-en-1-yl, 1-ethylbut-2-en-1-yl, 1-ethylbut-3-en-1-yl, 2-ethylbut-1-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl, 1-ethyl-2-methylprop-1-en-1-yl and 1-ethyl-2-methylprop-2-en-1-yl;

$C_2$–$C_6$-alkenyl: $C_3$–$C_6$-alkenyl as mentioned above, and also ethenyl;

$C_3$–$C_6$-alkynyl: prop-1-yn-1-yl, prop-2-yn-1-yl, but-1-yn-1-yl, but-1-yn-3-yl, but-1-yn-4-yl, but-2-yn-1-yl, pent-1-yn-1-yl, pent-1-yn-3-yl, pent-1-yn-4-yl, pent-1-yn-5-yl, pent-2-yn-1-yl, pent-2-yn-4-yl, pent-2-yn-5-yl, 3-methylbut-1-yn-3-yl, 3-methylbut-1-yn-4-yl, hex-1-yn-1-yl, hex-1-yn-3-yl, hex-1-yn-4-yl, hex-1-yn-5-yl, hex-1-yn-6-yl, hex-2-yn-1-yl, hex-2-yn-4-yl, hex-2-yn-5-yl, hex-2-yn-6-yl, hex-3-yn-1-yl, hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl and 4-methylpent-2-yn-5-yl;

$C_2$–$C_6$-alkynyl: $C_3$–$C_6$-alkynyl as mentioned above, and also ethynyl:

$C_3$–$C_6$-cycloalkyl: cyclopropyl, cyclobutyl, cyclopentyl and cyclohexyl;

$C_4$–$C_6$-cycloalkenyl: cyclobuten-1-yl, cyclobuten-3-yl, cyclopenten-1-yl, cyclopenten-3-yl, cyclopenten-4-yl, cyclohexen-1-yl, cyclohexen-3-yl and cyclohexen-4-yl;

heterocyclyl, and also the heterocyclyl radicals in heterocyclyloxy: three- to seven-membered saturated or partially unsaturated mono- or polycyclic heterocycles which contain one to three hetero atoms selected from a group consisting of oxygen, nitrogen and sulfur, such as oxiranyl, 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofuran-2-yl, 2,3- dihydrofuran-3-yl, 2,3-dihydrofuran-4-yl, 2,3-dihydrofuran-5-yl, 2,5-dihydrofuran-2-yl, 2,5-dihydrofuran-3-yl, 2,3-dihydrothien-2-yl, 2,3-dihydrothien-3-yl, 2,3-dihydrothien-4-yl, 2,3-dihydrothien-5-yl, 2,5-dihydrothien-2-yl, 2,5-dihydrothien-3-yl, 2,3-dihydropyrrol-2-yl, 2,3-dihydropyrrol-3-yl, 2,3-dihydropyrrol-4-yl, 2,3-dihydropyrrol-5-yl, 2,5-dihydropyrrol-2-yl, 2,5-dihydropyrrol-3-yl, 2,3-dihydroisoxazol-3-yl, 2,3-dihydroisoxazol-4-yl, 2,3-dihydroisoxazol-5-yl, 4,5-dihydroisoxazol-3-yl, 4,5-dihydroisoxazol-4-yl, 4,5-dihydroisoxazol-5-yl, 2,5-dihydroisoxazol-3-yl, 2,5-dihydroisoxazol-4-yl, 2,5-dihydroisoxazol-5-yl, 2,3-dihydroisothiazol-3-yl, 2,3-dihydroisothiazol-4-yl, 2,3-dihydroisothiazol-5-yl, 4,5-dihydroisothiazol-3-yl, 4,5-dihydroisothiazol-4-yl, 4,5-dihydroisothiazol-5-yl, 2,5-dihydroisothiazol-3-yl, 2,5-dihydroisothiazol-4-yl, 2,5-dihydroisothiazol-5-yl, 2,3-dihydropyrazol-3-yl, 2,3-dihydropyrazol-4-yl, 2,3-dihydropyrazol-5-yl, 4,5-dihydropyrazol-3-yl, 4,5-dihydropyrazol-4-yl, 4,5-dihydropyrazol-5-yl, 2,5-dihydropyrazol-3-yl, 2,5-dihydropyrazol-4-yl, 2,5-dihydropyrazol-5-yl, 2,3-dihydrooxazol-2-yl, 2,3-dihydrooxazol-4-yl, 2,3-dihydrooxazol-5-yl, 4,5-dihydrooxazol-2-yl, 4,5-dihydrooxazol-4-yl, 4,5-dihydrooxazol-5-yl, 2,5-dihydrooxazol-2-yl, 2,5-dihydrooxazol-4-yl, 2,5-dihydrooxazol-5-yl, 2,3-dihydrothiazol-2-yl, 2,3-dihydrothiazol-4-yl, 2,3-dihydrothiazol-5-yl, 4,5-dihydrothiazol-2-yl, 4,5-dihydrothiazol-4-yl, 4,5-dihydrothiazol-5-yl, 2,5-dihydrothiazol-2-yl, 2,5-dihydrothiazol-4-yl, 2,5-dihydrothiazol-5-yl, 2,3-dihydroimidazol-2-yl, 2,3-dihydroimidazol-4-yl, 2,3-dihydroimidazol-5-yl, 4,5-dihydroimidazol-2-yl, 4,5-dihydroimidazol-4-yl, 4,5-dihydroimidazol-5-yl, 2,5-dihydroimidazol-2-yl, 2,5-dihydroimidazol-4-yl, 2,5-dihydroimidazol-5-yl, 2-morpholinyl, 3-morpholinyl, 2-piperidinyl, 3-piperidinyl, 4-piperidinyl, 3-tetrahydropyridazinyl, 4-tetrahydropyridazinyl, 2-tetrahydropyrimidinyl, 4-tetrahydropyrimidinyl, 5-tetrahydropyrimidinyl, 2-tetrahydropyrazinyl, 1,3,5-tetrahydrotriazin-2-yl, 1,2,4-tetrahydrotriazin-3-yl, 1,3-dihydrooxazin-2-yl, 1,3-dithian-2-yl, 2-tetrahydropyranyl, 3-tetrahydropyranyl, 4-tetrahydropyranyl, 2-tetrahydrothiopyranyl, 3-tetrahydrothiopyranyl, 4-tetrahydrothiopyranyl, 1,3-dioxolan-2-yl, 3,4,5,6-tetrahydropyridin-2-yl, 4H-1,3-thiazin-2-yl, 4H-3,1-benzothiazin-2-yl, 1,1-dioxo-2,3,4,5-tetrahydrothien-2-yl, 2H-1,4-benzothiazin-3-yl, 2H-1,4-benzoxazin-3-yl, 1,3-dihydrooxazin-2-yl, hetaryl, and also the hetaryl radicals in hetaryloxy: aromatic mono- or polycyclic radicals which, besides carbon ring members, may additionally contain one to four nitrogen atoms or one to three nitrogen atoms and one oxygen or one sulfur atom or one oxygen or one sulfur atom, eg. 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl, 1,3,4-triazol-2-yl, 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl, 1,2,4,5-tetrazin-3-yl, and also the corresponding benzo-fused derivatives.

All phenyl, hetaryl and heterocyclyl rings are preferably unsubstituted or carry one to three halogen atoms and/or one or two radicals selected from the following group: nitro, cyano, methyl, trifluoromethyl, methoxy, trifluoromethoxy and methoxycarbonyl.

With a view to the use of the compounds of the formula I according to the invention as herbicides, the variables preferably have the following meanings, viz. in each case alone or in combination:

$R^1$ is nitro, halogen, cyano, thiocyanato, $C_1$–$C_6$-alkyl, $C_1$–$C_6$-haloalkyl, $C_1$–$C_6$-alkoxy-$C_1$–$C_6$-alkyl, $C_2$–$C_6$-alkenyl, $C_2$–$C_6$-alkynyl, —$OR^3$ or —$S(O)_nR^3$;
particularly preferably nitro, halogen such as, for example, fluorine, chlorine or bromine, $C_1$–$C_6$-haloalkyl, —$OR^3$ or —$SO_2R^3$;

$R^2$ is hydrogen, nitro, halogen, cyano, thiocyanato, $C_1$–$C_6$-alkyl, $C_1$–$C_6$-haloalkyl, $C_1$–$C_6$-alkoxy-$C_1$–$C_6$-alkyl, $C_2$–$C_6$-alkenyl, $C_2$–$C_6$-alkynyl, —$OR^3$ or —$S(O)_nR^3$;
particularly preferably hydrogen, nitro, halogen such as, for example, fluorine, chlorine or bromine, $C_1$–$C_6$-alkyl, $C_1$–$C_6$-haloalkyl, —$OR^3$ or —$SO_2R^3$;

n is 0, 1 or 2, particularly preferably 0 or 2;

$R^3$ is hydrogen, $C_1$–$C_6$-alkyl, $C_1$–$C_6$-haloalkyl, $C_2$–$C_6$-alkenyl, $C_2$–$C_6$-alkynyl, phenyl or phenyl-$C_1$–$C_6$-alkyl; particularly preferably hydrogen, $C_1$–$C_4$-alkyl, $C_1$–$C_4$-haloalkyl, $C_2$–$C_3$-alkenyl, $C_2$–$C_3$-alkynyl or phenyl; where the abovementioned alkyl radicals may be partially or fully halogenated and/or may carry one to three of the following groups:
hydroxyl, mercapto, amino, cyano, $R^3$, —$OR^3$, —$SR^3$, —$N(R^3)_2$, =$NOR^3$, —$OCOR^3$, —$SCOR^3$, —$NR^3COR^3$, —$CO_2R^3$, —$COSR^3$, —$CON(R^3)_2$, $C_1$–$C_4$-alkyliminooxy, $C_1$–$C_4$-alkoxyamino, $C_1$–$C_4$-alkylcarbonyl, $C_1$–$C_4$-alkoxy-$C_2$–$C_6$-alkoxycarbonyl, $C_1$–$C_4$-alkylsulfonyl, heterocyclyl, heterocyclyloxy, phenyl, benzyl, hetaryl, phenoxy, benzyloxy and hetaryloxy, where the eight last-mentioned radicals may in turn be substituted;

$R^4$ is hydrogen, $C_1$–$C_6$-alkyl or $C_1$–$C_6$-haloalkyl; particularly preferably hydrogen, methyl, ethyl or trifluoromethyl;

$R^5$ is $C_1$–$C_6$-alkyl or $C_1$–$C_6$-haloalkyl; particularly preferably methyl, ethyl, propyl, isopropyl, butyl or isobutyl;

$R^6$ is hydrogen, $C_1$–$C_6$-alkyl, $C_1$–$C_6$-alkylcarbonyl, $C_1$–$C_6$-haloalkylcarbonyl, $C_1$–$C_6$-alkoxycarbonyl, $C_1$–$C_6$-alkylsulfonyl, $C_1$–$C_6$-haloalkylsulfonyl, phenylcarbonylmethyl, or phenylsulfonyl, where the phenyl ring of the two last-mentioned substituents may be partially or fully halogenated and/or may carry one to three of the following radicals: nitro, cyano, $C_1$–$C_4$-alkyl, $C_1$–$C_4$-haloalkyl, $C_1$–$C_4$-alkoxy, $C_1$–$C_4$-haloalkoxy;

$X^1$ is a straight-chain or branched $C_1$–$C_4$-alkylene, a $C_2$–$C_4$-alkenylene or a $C_2$–$C_4$-alkynylene chain, particularly preferably an ethylene, propylene, propenylene or propynylene chain which is interrupted by a hetero atom selected from the group consisting of oxygen and sulfur, preferably oxygen,
where the abovementioned alkylene, alkenylene or alkynylene radicals may be partially halogenated and/or may carry one to three of the following groups:
—$OR^7$, —$OCOR^7$, —$OCONHR^7$ or —$OSO_2R^7$;

$R^7$ is hydrogen, $C_1$–$C_4$-alkyl, $C_2$–$C_4$-alkenyl, $C_2$–$C_4$-alkynyl, phenyl, phenyl-$C_1$–$C_4$-alkyl, where the abovementioned alkyl, alkenyl or alkynyl radicals may be partially or fully halogenated and/or may be substituted by one or more of the following radicals:

hydroxyl, mercapto, amino, cyano, nitro, formyl, $C_1$–$C_4$-alkylamino, $C_1$–$C_4$-dialkylamino, $C_1$–$C_4$-alkoxycarbonyl, $C_1$–$C_4$-alkylcarbonyl, $C_1$–$C_4$-alkylcarbonyloxy, $C_1$–$C_4$-alkyl, $C_1$–$C_4$-haloalkyl, $C_1$–$C_4$-alkylthio, $C_1$–$C_4$-haloalkylthio, $C_1$–$C_4$-alkoxy, $C_1$–$C_4$-haloalkoxy;

Het is a three- to six-membered, preferably a five- or six-membered, partially or fully saturated heterocyclic group or a three- to six-membered, preferably five- or six-membered, heteroaromatic group having up to three hetero atoms, particularly preferably having one or two hetero atoms, selected from the following three groups:
nitrogen,
oxygen in combination with at least one nitrogen or sulfur in combination with at least one nitrogen,
particularly preferably from the following two groups:
nitrogen or
oxygen in combination with at least one nitrogen,
where the abovementioned heterocyclic or heteroaromatic group may be partially or fully halogenated and/or may be substituted by $R^8$;

$R^8$ is hydrogen, hydroxyl, mercapto, amino, cyano, nitro, formyl, $C_1$–$C_4$-alkylamino, $C_1$–$C_4$-dialkylamino, $C_1$–$C_4$-alkoxycarbonyl, $C_1$–$C_4$-alkylcarbonyl, $C_1$–$C_4$-alkylcarbonyloxy, $C_1$–$C_4$-alkyl, $C_1$–$C_4$-haloalkyl, $C_1$–$C_4$-alkylthio, $C_1$–$C_4$-haloalkylthio, $C_1$–$C_4$-alkoxy, $C_1$–$C_4$-haloalkoxy, where the alkyl radicals may in each case be substituted by in each case one or more of the following radicals:
cyano, formyl, $C_1$–$C_4$-alkylamino, $C_1$–$C_4$-dialkylamino, $C_1$–$C_4$-alkoxycarbonyl, $C_1$–$C_4$-alkylcarbonyl, $C_1$–$C_4$-alkylcarbonyloxy, $C_1$–$C_4$-alkyl, $C_1$–$C_4$-haloalkyl, $C_1$–$C_4$-alkylthio, $C_1$–$C_4$-haloalkylthio, $C_1$–$C_4$-alkoxy, $C_1$–$C_4$-haloalkoxy.

Particular preference is given to the compounds of the formula Ia where $R^1$ is bonded in position 2 and $R^2$ is bonded in position 4 of the phenyl ring.

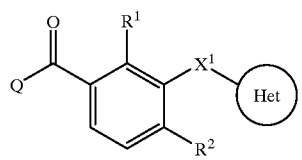

Ia

Most particular preference is given to the compounds of the formula Ia where the substituents $R^1$ and $R^2$ and Q are each as defined above, $X^1$ is a $C_1$–$C_3$-alkylene, a $C_2$–$C_3$-alkenylene or $C_2$–$C_3$-alkynylene chain which is interrupted by an oxygen atom and Het is a three- to six-membered, preferably a five- or six-membered, partially or fully saturated heterocyclic group or a three- to six-membered, preferably five- or six-membered, heteroaromatic group having up to three hetero atoms, particularly preferably having one or two hetero atoms, selected from the following three groups:
nitrogen,
oxygen in combination with at least one nitrogen or sulfur in combination with at least one nitrogen,
particularly preferably from the following two groups:
nitrogen or
oxygen in combination with at least one nitrogen,
where the abovementioned heterocyclic or heteroaromatic group may be partially or fully halogenated and/or may be substituted by $R^8$.

Furthermore, most particular preference is given to the compounds of the formula Ia according to the invention where the substituents $R^1$, $R^2$ and $X^1$ are each as defined above and Het is a five- or six-membered partially or fully saturated heterocyclic group or a five- or six-membered heteroaromatic group having up to three hetero atoms, particularly preferably having one or two hetero atoms, selected from the following three groups:
nitrogen,
oxygen in combination with at least one nitrogen or sulfur in combination with at least one nitrogen,
particularly preferably from the following two groups:
nitrogen or
oxygen in combination with at least one nitrogen,
where the abovementioned heterocyclic or heteroaromatic group may be partially or fully halogenated and/or may be substituted by $R^8$.

Particular preference is given to the compounds Ib of Tables 1 to 144.

TABLE A

| No. | $X^1$ | Het |
|---|---|---|
| 1 | $OCH_2$ | oxiranyl |
| 2 | $OCH_2$ | 3-methyl-2-oxiranyl |
| 3 | $OCH_2$ | 2-oxetanyl |
| 4 | $OCH_2$ | 3-hydroxy-3-methyl-2-oxetanyl |
| 5 | $OCH_2$ | 3-hydroxy-3-ethyl-2-oxetanyl |
| 6 | $OCH_2$ | 3-hydroxy-3-propyl-2-oxetanyl |
| 7 | $OCH_2$ | 3-hydroxy-3-butyl-2-oxetanyl |
| 8 | $OCH_2$ | 3-methoxy-3-methyl-2-oxetanyl |
| 9 | $OCH_2$ | 3-methoxy-3-ethyl-2-oxetanyl |
| 10 | $OCH_2$ | 3-methoxy-3-propyl-2-oxetanyl |
| 11 | $OCH_2$ | 3-methoxy-3-butyl-2-oxetanyl |
| 12 | $OCH_2$ | 3-trimethyl-silyloxy-3-methyl-2-oxetanyl |
| 13 | $OCH_2$ | 3-trimethyl-silyloxy-3-ethyl-2-oxetanyl |
| 14 | $OCH_2$ | 3-trimethyl-silyloxy-3-propyl-2-oxetanyl |
| 15 | $OCH_2$ | 3-trimethyl-silyloxy-3-butyl-2-oxetanyl |
| 16 | $OCH_2$ | 3-oxetanyl |
| 17 | $OCH_2$ | 2-furyl |
| 18 | $OCH_2$ | 4,5-dihydro-2-furyl |
| 19 | $OCH_2$ | 2,3-dihydro-2-furyl |
| 20 | $OCH_2$ | 3-furyl |
| 21 | $OCH_2$ | 4,5-dihydro-3-furyl |
| 22 | $OCH_2$ | 2,3-dihydro-3-furyl |
| 23 | $OCH_2$ | 2-thienyl |
| 24 | $OCH_2$ | 4,5-dihydro-2-thienyl |
| 25 | $OCH_2$ | 2,3-dihydro-2-thienyl |
| 26 | $OCH_2$ | 5-chloro-2-thienyl |
| 27 | $OCH_2$ | 5-methyl-2-thienyl |
| 28 | $OCH_2$ | 3-thienyl |
| 29 | $OCH_2$ | 4,5-dihydro-3-thienyl |
| 30 | $OCH_2$ | 2,3-dihydro-3-thienyl |
| 31 | $OCH_2$ | 2-pyrrolyl |
| 32 | $OCH_2$ | 2,5-dihydro-2-pyrrolyl |
| 33 | $OCH_2$ | 3-pyrrolyl |
| 34 | $OCH_2$ | 2,5-dihydro-3-pyrrolyl |
| 35 | $OCH_2$ | 3-isoxazolyl |
| 36 | $OCH_2$ | 4-methyl-3-isoxazolyl |
| 37 | $OCH_2$ | 5-methyl-3-isoxazolyl |
| 38 | $OCH_2$ | 4,5-dimethyl-3-isoxazolyl |

TABLE A-continued

| No. | X¹ | Het |
|---|---|---|
| 39 | OCH$_2$ | 4,5-dihydro-3-isoxazolyl |
| 40 | OCH$_2$ | 4-methyl-4,5-dihydro-3-isoxazolyl |
| 41 | OCH$_2$ | 5-methyl-4,5-dihydro-3-isoxazolyl |
| 42 | OCH$_2$ | 4,5-dimethyl-4,5-dihydro-3-isoxazolyl |
| 43 | OCH$_2$ | 4-isoxazolyl |
| 44 | OCH$_2$ | 3-methyl-4-isoxazolyl |
| 45 | OCH$_2$ | 5-methyl-4-isoxazolyl |
| 46 | OCH$_2$ | 5-cyclopropyl-4-isoxazolyl |
| 47 | OCH$_2$ | 5-phenyl-4-isoxazolyl |
| 48 | OCH$_2$ | 3,5-dimethyl-4-isoxazolyl |
| 49 | OCH$_2$ | 4,5-dihydro-4-isoxazolyl |
| 50 | OCH$_2$ | 3-methyl-4,5-dihydro-4-isoxazolyl |
| 51 | OCH$_2$ | 5-methyl-4,5-dihydro-4-isoxazolyl |
| 52 | OCH$_2$ | 3,5-dimethyl-4,5-dihydro-4-isoxazolyl |
| 53 | OCH$_2$ | 5-isoxazolyl |
| 54 | OCH$_2$ | 3-methyl-5-isoxazolyl |
| 55 | OCH$_2$ | 4-methyl-5-isoxazolyl |
| 56 | OCH$_2$ | 3,4-dimethyl-5-isoxazolyl |
| 57 | OCH$_2$ | 4,5-dihydro-5-isoxazolyl |
| 58 | OCH$_2$ | 3-methyl-4,5-dihydro-5-isoxazolyl |
| 59 | OCH$_2$ | 4-methyl-4,5-dihydro-5-isoxazolyl |
| 60 | OCH$_2$ | 3,4-dimethyl-4,5-dihydro-5-isoxazolyl |
| 61 | OCH$_2$ | 3-isothiazolyl |
| 62 | OCH$_2$ | 4-methyl-3-isothiazolyl |
| 63 | OCH$_2$ | 5-methyl-3-isothiazolyl |
| 64 | OCH$_2$ | 4-isothiazolyl |
| 65 | OCH$_2$ | 3-methyl-4-isothiazolyl |
| 66 | OCH$_2$ | 5-methyl-4-isothiazolyl |
| 67 | OCH$_2$ | 5-isothiazolyl |
| 68 | OCH$_2$ | 3-methyl-5-isothiazolyl |
| 69 | OCH$_2$ | 4-methyl-5-isothiazolyl |
| 70 | OCH$_2$ | 2-oxazolyl |
| 71 | OCH$_2$ | 4-oxazolyl |
| 72 | OCH$_2$ | 5-oxazolyl |
| 73 | OCH$_2$ | 2-thiazolyl |
| 74 | OCH$_2$ | 4-thiazolyl |
| 75 | OCH$_2$ | 5-thiazolyl |
| 76 | OCH$_2$ | 3-pyrazolyl |
| 77 | OCH$_2$ | 4-pyrazolyl |
| 78 | OCH$_2$ | 1-methyl-3-pyrazolyl |
| 79 | OCH$_2$ | 1-methyl-4-pyrazolyl |
| 80 | OCH$_2$ | 1-methyl-5-pyrazolyl |
| 81 | OCH$_2$ | 2-imidazolyl |
| 82 | OCH$_2$ | 1-methyl-2-imidazolyl |
| 83 | OCH$_2$ | 5-methyl-[1,3,4]-2-oxadiazolyl |
| 84 | OCH$_2$ | 5-methyl-[1,2,4]-3-oxadiazolyl |
| 85 | OCH$_2$ | 5-methyl-[1,3,4]-2-thiadiazolyl |
| 86 | OCH$_2$ | 5-methyl-[1,2,4]-3-thiadiazolyl |
| 87 | OCH$_2$ | [1,2,4]-3-triazolyl |
| 88 | OCH$_2$ | [1,2,3]-4-triazolyl |
| 89 | OCH$_2$ | 2-pyridyl |
| 90 | OCH$_2$ | 6-chloro-2-pyridyl |
| 91 | OCH$_2$ | 6-methoxy-2-pyridyl |
| 92 | OCH$_2$ | 6-trifluoromethyl-2-pyridyl |
| 93 | OCH$_2$ | 3-pyridyl |
| 94 | OCH$_2$ | 2-chloro-3-pyridyl |
| 95 | OCH$_2$ | 2-methoxy-3-pyridyl |
| 96 | OCH$_2$ | 4-pyridyl |
| 97 | OCH$_2$ | 2-chloro-4-pyridyl |
| 98 | OCH$_2$ | 2-methoxy-4-pyridyl |
| 99 | OCH$_2$ | 2-ethoxy-4-pyridyl |
| 100 | OCH$_2$ | 2-methylthio-4-pyridyl |
| 101 | OCH$_2$ | 2-trifluoromethyl-5-pyridyl |
| 102 | OCH$_2$ | 2-pyrimidinyl |
| 103 | OCH$_2$ | 3-pyrimidinyl |
| 104 | OCH$_2$ | 4-pyrimidinyl |
| 105 | OCH$_2$ | 2-pyrazinyl |
| 106 | OCH$_2$ | 3-pyridazinyl |
| 107 | OCH$_2$ | 4-pyridazinyl |
| 108 | OCH$_2$ | 2-(2H-1,3-oxazinyl) |
| 109 | OCH$_2$ | 2-(6H-1,3-oxazinyl) |
| 110 | OCH$_2$ | 4-(6H-1,3-oxazinyl) |
| 111 | OCH$_2$ | 6-(6H-1,3-oxazinyl) |
| 112 | OCH$_2$ | [1,3,5]-2-triazinyl |
| 113 | OCH$_2$ | [1,2,4]-3-triazinyl |
| 114 | OCH$_2$ | [1,2,4]-5-triazinyl |
| 115 | OCH$_2$ | [1,2,4]-6-triazinyl |
| 116 | | oxiranyl |
| 117 | | 3-methyl-2-oxiranyl |
| 118 | | 2-oxetanyl |
| 119 | | 3-hydroxy-3-methyl-2-oxetanyl |
| 120 | | 3-hydroxy-3-ethyl-2-oxetanyl |
| 121 | | 3-hydroxy-3-propyl-2-oxetanyl |
| 122 | | 3-hydroxy-3-butyl-2-oxetanyl |
| 123 | | 3-methoxy-3-methyl-2-oxetanyl |
| 124 | | 3-methoxy-3-ethyl-2-oxetanyl |
| 125 | | 3-methoxy-3-propyl-2-oxetanyl |
| 126 | | 3-methoxy-3-butyl-2-oxetanyl |
| 127 | | 3-trimethylsilyloxy-3-methyl-2-oxetanyl |
| 128 | | 3-trimethylsilyloxy-3-ethyl-2-oxetanyl |
| 129 | | 3-trimethylsilyloxy-3-propyl-2-oxetanyl |
| 130 | | 3-trimethylsilyloxy-3-butyl-2-oxetanyl |
| 131 | | 3-oxetanyl |
| 132 | | 2-furyl |
| 133 | | 4,5-dihydro-2-furyl |
| 134 | | 2,3-dihydro-2-furyl |
| 135 | | 3-furyl |
| 136 | | 4,5-dihydro-3-furyl |
| 137 | | 2,3-dihydro-3-furyl |
| 138 | | 2-thienyl |
| 139 | CH$_2$O | 4,5-dihydro-2-thienyl |
| 140 | CH$_2$O | 2,3-dihydro-2-thienyl |
| 141 | CH$_2$O | 5-chloro-2-thienyl |
| 142 | CH$_2$O | 5-methyl-2-thienyl |
| 143 | CH$_2$O | 3-thienyl |
| 144 | CH$_2$O | 4,5-dihydro-3-thienyl |
| 145 | CH$_2$O | 2,3-dihydro-3-thienyl |
| 146 | CH$_2$O | 2-pyrrolyl |
| 147 | CH$_2$O | 2,5-dihydro-2-pyrrolyl |
| 148 | CH$_2$O | 3-pyrrolyl |
| 149 | CH$_2$O | 2,5-dihydro-3-pyrrolyl |
| 150 | CH$_2$O | 3-isoxazolyl |
| 151 | CH$_2$O | 4-methyl-3-isoxazolyl |
| 152 | CH$_2$O | 5-methyl-3-isoxazolyl |
| 153 | CH$_2$O | 4,5-dimethyl-3-isoxazolyl |
| 154 | CH$_2$O | 4,5-dihydro-3-isoxazolyl |
| 155 | CH$_2$O | 4-methyl-4,5-dihydro-3-isoxazolyl |
| 156 | CH$_2$O | 5-methyl-4,5-dihydro-3-isoxazolyl |
| 157 | CH$_2$O | 4,5-dimethyl-4,5-dihydro-3-isoxazolyl |
| 158 | CH$_2$O | 4-isoxazolyl |
| 159 | CH$_2$O | 3-methyl-4-isoxazolyl |
| 160 | CH$_2$O | 5-methyl-4-isoxazolyl |
| 161 | CH$_2$O | 5-cyclopropyl-4-isoxazolyl |

TABLE A-continued

| No. | X¹ | Het |
|---|---|---|
| 162 | CH₂O | 5-phenyl-4-isoxazolyl |
| 163 | CH₂O | 3,5-dimethyl-4-isoxazolyl |
| 164 | CH₂O | 4,5-dihydro-4-isoxazolyl |
| 165 | CH₂O | 3-methyl-4,5-dihydro-4-isoxazolyl |
| 166 | CH₂O | 5-methyl-4,5-dihydro-4-isoxazolyl |
| 167 | CH₂O | 3,5-dimethyl-4,5-dihydro-4-isoxazolyl |
| 168 | CH₂O | 5-isoxazolyl |
| 169 | CH₂O | 3-methyl-5-isoxazolyl |
| 170 | CH₂O | 4-methyl-5-isoxazolyl |
| 171 | CH₂O | 3,4-dimethyl-5-isoxazolyl |
| 172 | CH₂O | 4,5-dihydro-5-isoxazolyl |
| 173 | CH₂O | 3-methyl-4,5-dihydro-5-isoxazolyl |
| 174 | CH₂O | 4-methyl-4,5-dihydro-5-isoxazolyl |
| 175 | CH₂O | 3,4-dimethyl-4,5-dihydro-5-isoxazolyl |
| 176 | CH₂O | 3-isothiazolyl |
| 177 | CH₂O | 4-methyl-3-isothiazolyl |
| 178 | CH₂O | 5-methyl-3-isothiazolyl |
| 179 | CH₂O | 4-isothiazolyl |
| 180 | CH₂O | 3-methyl-4-isothiazolyl |
| 181 | CH₂O | 5-methyl-4-isothiazolyl |
| 182 | CH₂O | 5-isothiazolyl |
| 183 | CH₂O | 3-methyl-5-isothiazolyl |
| 184 | CH₂O | 4-methyl-5-isothiazolyl |
| 185 | CH₂O | 2-oxazolyl |
| 186 | CH₂O | 4-oxazolyl |
| 187 | CH₂O | 5-oxazolyl |
| 188 | CH₂O | 2-thiazolyl |
| 189 | CH₂O | 4-thiazolyl |
| 190 | CH₂O | 5-thiazolyl |
| 191 | CH₂O | 3-pyrazolyl |
| 192 | CH₂O | 4-pyrazolyl |
| 193 | CH₂O | 1-methyl-3-pyrazolyl |
| 194 | CH₂O | 1-methyl-4-pyrazolyl |
| 195 | CH₂O | 1-methyl-5-pyrazolyl |
| 196 | CH₂O | 2-imidazolyl |
| 197 | CH₂O | 1-methyl-2-imidazolyl |
| 198 | CH₂O | 5-methyl-[1,3,4]-2-oxadiazolyl |
| 199 | CH₂O | 5-methyl-[1,2,4]-3-oxadiazolyl |
| 200 | CH₂O | 5-methyl-[1,3,4]-2-thiadiazolyl |
| 201 | CH₂O | 5-methyl-[1,2,4]-3-thiadiazolyl |
| 202 | CH₂O | [1,2,4]-3-triazolyl |
| 203 | CH₂O | [1,2,3]-4-triazolyl |
| 204 | CH₂O | 2-pyridyl |
| 205 | CH₂O | 6-chloro-2-pyridyl |
| 206 | CH₂O | 6-methoxy-2-pyridyl |
| 207 | CH₂O | 6-trifluoromethyl-2-pyridyl |
| 208 | CH₂O | 3-pyridyl |
| 209 | CH₂O | 2-chloro-3-pyridyl |
| 210 | CH₂O | 2-methoxy-3-pyridyl |
| 211 | CH₂O | 4-pyridyl |
| 212 | CH₂O | 2-chloro-4-pyridyl |
| 213 | CH₂O | 2-methoxy-4-pyridyl |
| 214 | CH₂O | 2-ethoxy-4-pyridyl |
| 215 | CH₂O | 2-methylthio-4-pyridyl |
| 216 | CH₂O | 2-trifluoromethyl-5-pyridyl |
| 217 | CH₂O | 2-pyrimidinyl |
| 218 | CH₂O | 3-pyrimidinyl |
| 219 | CH₂O | 4-pyrimidinyl |
| 220 | CH₂O | 2-pyrazinyl |
| 221 | CH₂O | 3-pyridazinyl |
| 222 | CH₂O | 4-pyridazinyl |
| 223 | CH₂O | 2-(2H-1,3-oxazinyl) |
| 224 | CH₂O | 2-(6H-1,3-oxazinyl) |
| 225 | CH₂O | 4-(6H-1,3-oxazinyl) |
| 226 | CH₂O | 6-(6H-1,3-oxazinyl) |
| 227 | CH₂O | [1,3,5]-2-triazinyl |
| 228 | CH₂O | [1,2,4]-3-triazinyl |
| 229 | CH₂O | [1,2,4]-5-triazinyl |
| 230 | CH₂O | [1,2,4]-6-triazinyl |
| 231 | OCH₂CH₂ | oxiranyl |
| 232 | OCH₂CH₂ | 3-methyl-2-oxiranyl |
| 233 | OCH₂CH₂ | 2-oxetanyl |
| 234 | OCH₂CH₂ | 3-hydroxy-3-methyl-2-oxetanyl |
| 235 | OCH₂CH₂ | 3-hydroxy-3-ethyl-2-oxetanyl |
| 236 | OCH₂CH₂ | 3-hydroxy-3-propyl-2-oxetanyl |
| 237 | OCH₂CH₂ | 3-hydroxy-3-butyl-2-oxetanyl |
| 238 | OCH₂CH₂ | 3-methoxy-3-methyl-2-oxetanyl |
| 239 | OCH₂CH₂ | 3-methoxy-3-ethyl-2-oxetanyl |
| 240 | OCH₂CH₂ | 3-methoxy-3-propyl-2-oxetanyl |
| 241 | OCH₂CH₂ | 3-methoxy-3-butyl-2-oxetanyl |
| 242 | OCH₂CH₂ | 3-trimethylsilyloxy-3-methyl-2-oxetanyl |
| 243 | OCH₂CH₂ | 3-trimethylsilyloxy-3-ethyl-2-oxetanyl |
| 244 | OCH₂CH₂ | 3-trimethylsilyloxy-3-propyl-2-oxetanyl |
| 245 | OCH₂CH₂ | 3-trimethylsilyloxy-3-butyl-2-oxetanyl |
| 246 | OCH₂CH₂ | 3-oxetanyl |
| 247 | OCH₂CH₂ | 2-furyl |
| 248 | OCH₂CH₂ | 4,5-dihydro-2-furyl |
| 249 | OCH₂CH₂ | 2,3-dihydro-2-furyl |
| 250 | OCH₂CH₂ | 3-furyl |
| 251 | OCH₂CH₂ | 4,5-dihydro-3-furyl |
| 252 | OCH₂CH₂ | 2,3-dihydro-3-furyl |
| 253 | OCH₂CH₂ | 2-thienyl |
| 254 | OCH₂CH₂ | 4,5-dihydro-2-thienyl |
| 255 | OCH₂CH₂ | 2,3-dihydro-2-thienyl |
| 256 | OCH₂CH₂ | 5-chloro-2-thienyl |
| 257 | OCH₂CH₂ | 5-methyl-2-thienyl |
| 258 | OCH₂CH₂ | 3-thienyl |
| 259 | OCH₂CH₂ | 4,5-dihydro-3-thienyl |
| 260 | OCH₂CH₂ | 2,3-dihydro-3-thienyl |
| 261 | OCH₂CH₂ | 2-pyrrolyl |
| 262 | OCH₂CH₂ | 2,5-dihydro-2-pyrrolyl |
| 263 | OCH₂CH₂ | 3-pyrrolyl |
| 264 | OCH₂CH₂ | 2,5-dihydro-3-pyrrolyl |
| 265 | OCH₂CH₂ | 3-isoxazolyl |
| 266 | OCH₂CH₂ | 4-methyl-3-isoxazolyl |
| 267 | OCH₂CH₂ | 5-methyl-3-isoxazolyl |
| 268 | OCH₂CH₂ | 4,5-dimethyl-3-isoxazolyl |
| 269 | OCH₂CH₂ | 4,5-dihydro-3-isoxazolyl |
| 270 | OCH₂CH₂ | 4-methyl-4,5-dihydro-3-isoxazolyl |
| 271 | OCH₂CH₂ | 5-methyl-4,5-dihydro-3-isoxazolyl |
| 272 | OCH₂CH₂ | 4,5-dimethyl-4,5-dihydro-3-isoxazolyl |
| 273 | OCH₂CH₂ | 4-isoxazolyl |
| 274 | OCH₂CH₂ | 3-methyl-4-isoxazolyl |
| 275 | OCH₂CH₂ | 5-methyl-4-isoxazolyl |
| 276 | OCH₂CH₂ | 5-cyclopropyl-4-isoxazolyl |
| 277 | OCH₂CH₂ | 5-phenyl-4-isoxazolyl |
| 278 | OCH₂CH₂ | 3,5-dimethyl-4-isoxazolyl |
| 279 | OCH₂CH₂ | 4,5-dihydro-4-isoxazolyl |
| 280 | OCH₂CH₂ | 3-methyl-4,5-dihydro-4-isoxazolyl |
| 281 | OCH₂CH₂ | 5-methyl-4,5-dihydro-4-isoxazolyl |
| 282 | OCH₂CH₂ | 3,5-dimethyl-4,5-dihydro-4-isoxazolyl |
| 283 | OCH₂CH₂ | 5-isoxazolyl |

TABLE A-continued

| No. | X¹ | Het |
|---|---|---|
| 284 | OCH$_2$CH$_2$ | 3-methyl-5-isoxazolyl |
| 285 | OCH$_2$CH$_2$ | 4-methyl-5-isoxazolyl |
| 286 | OCH$_2$CH$_2$ | 3,4-dimethyl-5-isoxazolyl |
| 287 | OCH$_2$CH$_2$ | 4,5-dihydro-5-isoxazolyl |
| 288 | OCH$_2$CH$_2$ | 3-methyl-4,5-dihydro-5-isoxazolyl |
| 289 | OCH$_2$CH$_2$ | 4-methyl-4,5-dihydro-5-isoxazolyl |
| 290 | OCH$_2$CH$_2$ | 3,4-dimethyl-4,5-dihydro-5-isoxazolyl |
| 291 | OCH$_2$CH$_2$ | 3-isothiazolyl |
| 292 | OCH$_2$CH$_2$ | 4-methyl-3-isothiazolyl |
| 293 | OCH$_2$CH$_2$ | 5-methyl-3-isothiazolyl |
| 294 | OCH$_2$CH$_2$ | 4-isothiazolyl |
| 295 | OCH$_2$CH$_2$ | 3-methyl-4-isothiazolyl |
| 296 | OCH$_2$CH$_2$ | 5-methyl-4-isothiazolyl |
| 297 | OCH$_2$CH$_2$ | 5-isothiazolyl |
| 298 | OCH$_2$CH$_2$ | 3-methyl-5-isothiazolyl |
| 299 | OCH$_2$CH$_2$ | 4-methyl-5-isothiazolyl |
| 300 | OCH$_2$CH$_2$ | 2-oxazolyl |
| 301 | OCH$_2$CH$_2$ | 4-oxazolyl |
| 302 | OCH$_2$CH$_2$ | 5-oxazolyl |
| 303 | OCH$_2$CH$_2$ | 2-thiazolyl |
| 304 | OCH$_2$CH$_2$ | 4-thiazolyl |
| 305 | OCH$_2$CH$_2$ | 5-thiazolyl |
| 306 | OCH$_2$CH$_2$ | 3-pyrazolyl |
| 307 | OCH$_2$CH$_2$ | 4-pyrazolyl |
| 308 | OCH$_2$CH$_2$ | 1-methyl-3-pyrazolyl |
| 309 | OCH$_2$CH$_2$ | 1-methyl-4-pyrazolyl |
| 310 | OCH$_2$CH$_2$ | 1-methyl-5-pyrazolyl |
| 311 | OCH$_2$CH$_2$ | 2-imidazolyl |
| 312 | OCH$_2$CH$_2$ | 1-methyl-2-imidazolyl |
| 313 | OCH$_2$CH$_2$ | 5-methyl-[1,3,4]-2-oxadiazolyl |
| 314 | OCH$_2$CH$_2$ | 5-methyl-[1,2,4]-3-oxadiazolyl |
| 315 | OCH$_2$CH$_2$ | 5-methyl-[1,3,4]-2-thiadiazolyl |
| 316 | OCH$_2$CH$_2$ | 5-methyl-[1,2,4]-3-thiadiazolyl |
| 317 | OCH$_2$CH$_2$ | [1,2,4]-3-triazolyl |
| 318 | OCH$_2$CH$_2$ | [1,2,3]-4-triazolyl |
| 319 | OCH$_2$CH$_2$ | 2-pyridyl |
| 320 | OCH$_2$CH$_2$ | 6-chloro-2-pyridyl |
| 321 | OCH$_2$CH$_2$ | 6-methoxy-2-pyridyl |
| 322 | OCH$_2$CH$_2$ | 6-trifluoromethyl-2-pyridyl |
| 323 | OCH$_2$CH$_2$ | 3-pyridyl |
| 324 | OCH$_2$CH$_2$ | 2-chloro-3-pyridyl |
| 325 | OCH$_2$CH$_2$ | 2-methoxy-3-pyridyl |
| 326 | OCH$_2$CH$_2$ | 4-pyridyl |
| 327 | OCH$_2$CH$_2$ | 2-chloro-4-pyridyl |
| 328 | OCH$_2$CH$_2$ | 2-methoxy-4-pyridyl |
| 329 | OCH$_2$CH$_2$ | 2-ethoxy-4-pyridyl |
| 330 | OCH$_2$CH$_2$ | 2-methylthio-4-pyridyl |
| 331 | OCH$_2$CH$_2$ | 2-trifluoromethyl-5-pyridyl |
| 332 | OCH$_2$CH$_2$ | 2-pyrimidinyl |
| 333 | OCH$_2$CH$_2$ | 3-pyrimidinyl |
| 334 | OCH$_2$CH$_2$ | 4-pyrimidinyl |
| 335 | OCH$_2$CH$_2$ | 2-pyrazinyl |
| 336 | OCH$_2$CH$_2$ | 3-pyridazinyl |
| 337 | OCH$_2$CH$_2$ | 4-pyridazinyl |
| 338 | OCH$_2$CH$_2$ | 2-(2H-1,3-oxazinyl) |
| 339 | OCH$_2$CH$_2$ | 2-(6H-1,3-oxazinyl) |
| 340 | OCH$_2$CH$_2$ | 4-(6H-1,3-oxazinyl) |
| 341 | OCH$_2$CH$_2$ | 6-(6H-1,3-oxazinyl) |
| 342 | OCH$_2$CH$_2$ | [1,3,5]-2-triazinyl |
| 343 | OCH$_2$CH$_2$ | [1,2,4]-3-triazinyl |
| 344 | OCH$_2$CH$_2$ | [1,2,4]-5-triazinyl |
| 345 | OCH$_2$CH$_2$ | [1,2,4]-6-triazinyl |
| 346 | CH$_2$CH$_2$O | oxiranyl |
| 347 | CH$_2$CH$_2$O | 3-methyl-2-oxiranyl |
| 348 | CH$_2$CH$_2$O | 2-oxetanyl |
| 349 | CH$_2$CH$_2$O | 3-hydroxy-3-methyl-2-oxetanyl |
| 350 | CH$_2$CH$_2$O | 3-hydroxy-3-ethyl-2-oxetanyl |
| 351 | CH$_2$CH$_2$O | 3-hydroxy-3-propyl-2-oxetanyl |
| 352 | CH$_2$CH$_2$O | 3-hydroxy-3-butyl-2-oxetanyl |
| 353 | CH$_2$CH$_2$O | 3-methoxy-3-methyl-2-oxetanyl |
| 354 | CH$_2$CH$_2$O | 3-methoxy-3-ethyl-2-oxetanyl |
| 355 | CH$_2$CH$_2$O | 3-methoxy-3-propyl-2-oxetanyl |
| 356 | CH$_2$CH$_2$O | 3-methoxy-3-butyl-2-oxetanyl |
| 357 | CH$_2$CH$_2$O | 3-trimethyl-silyloxy-3-methyl-2-oxetanyl |
| 358 | CH$_2$CH$_2$O | 3-trimethyl-silyloxy-3-ethyl-2-oxetanyl |
| 359 | CH$_2$CH$_2$O | 3-trimethyl-silyloxy-3-propyl-2-oxetanyl |
| 360 | CH$_2$CH$_2$O | 3-trimethyl-silyloxy-3-butyl-2-oxetanyl |
| 361 | CH$_2$CH$_2$O | 3-oxetanyl |
| 362 | CH$_2$CH$_2$O | 2-furyl |
| 363 | CH$_2$CH$_2$O | 4,5-dihydro-2-furyl |
| 364 | CH$_2$CH$_2$O | 2,3-dihydro-2-furyl |
| 365 | CH$_2$CH$_2$O | 3-furyl |
| 366 | CH$_2$CH$_2$O | 4,5-dihydro-3-furyl |
| 367 | CH$_2$CH$_2$O | 2,3-dihydro-3-furyl |
| 368 | CH$_2$CH$_2$O | 2-thienyl |
| 369 | CH$_2$CH$_2$O | 4,5-dihydro-2-thienyl |
| 370 | CH$_2$CH$_2$O | 2,3-dihydro-2-thienyl |
| 371 | CH$_2$CH$_2$O | 5-chloro-2-thienyl |
| 372 | CH$_2$CH$_2$O | 5-methyl-2-thienyl |
| 373 | CH$_2$CH$_2$O | 3-thienyl |
| 374 | CH$_2$CH$_2$O | 4,5-dihydro-3-thienyl |
| 375 | CH$_2$CH$_2$O | 2,3-dihydro-3-thienyl |
| 376 | CH$_2$CH$_2$O | 2-pyrrolyl |
| 377 | CH$_2$CH$_2$O | 2,5-dihydro-2-pyrrolyl |
| 378 | CH$_2$CH$_2$O | 3-pyrrolyl |
| 379 | CH$_2$CH$_2$O | 2,5-dihydro-3-pyrrolyl |
| 380 | CH$_2$CH$_2$O | 3-isoxazolyl |
| 381 | CH$_2$CH$_2$O | 4-methyl-3-isoxazolyl |
| 382 | CH$_2$CH$_2$O | 5-methyl-3-isoxazolyl |
| 383 | CH$_2$CH$_2$O | 4,5-dimethyl-3-isoxazolyl |
| 384 | CH$_2$CH$_2$O | 4,5-dihydro-3-isoxazolyl |
| 385 | CH$_2$CH$_2$O | 4-methyl-4,5-dihydro-3-isoxazolyl |
| 386 | CH$_2$CH$_2$O | 5-methyl-4,5-dihydro-3-isoxazolyl |
| 387 | CH$_2$CH$_2$O | 4,5-dimethyl-4,5-dihydro-3-isoxazolyl |
| 388 | CH$_2$CH$_2$O | 4-isoxazolyl |
| 389 | CH$_2$CH$_2$O | 3-methyl-4-isoxazolyl |
| 390 | CH$_2$CH$_2$O | 5-methyl-4-isoxazolyl |
| 391 | CH$_2$CH$_2$O | 5-cyclopropyl-4-isoxazolyl |
| 392 | CH$_2$CH$_2$O | 5-phenyl-4-isoxazolyl |
| 393 | CH$_2$CH$_2$O | 3,5-dimethyl-4-isoxazolyl |
| 394 | CH$_2$CH$_2$O | 4,5-dihydro-4-isoxazolyl |
| 395 | CH$_2$CH$_2$O | 3-methyl-4,5-dihydro-4-isoxazolyl |
| 396 | CH$_2$CH$_2$O | 5-methyl-4,5-dihydro-4-isoxazolyl |
| 397 | CH$_2$CH$_2$O | 3,5-dimethyl-4,5-dihydro-4-isoxazolyl |
| 398 | CH$_2$CH$_2$O | 5-isoxazolyl |
| 399 | CH$_2$CH$_2$O | 3-methyl-5-isoxazolyl |
| 400 | CH$_2$CH$_2$O | 4-methyl-5-isoxazolyl |
| 401 | CH$_2$CH$_2$O | 3,4-dimethyl-5-isoxazolyl |
| 402 | CH$_2$CH$_2$O | 4,5-dihydro-5-isoxazolyl |
| 403 | CH$_2$CH$_2$O | 3-methyl-4,5-dihydro-5-isoxazolyl |
| 404 | CH$_2$CH$_2$O | 4-methyl-4,5-dihydro-5-isoxazolyl |

TABLE A-continued

| No. | X¹ | Het |
|---|---|---|
| 405 | CH₂CH₂O | 3,4-dimethyl-4,5-dihydro-5-isoxazolyl |
| 406 | CH₂CH₂O | 3-isothiazolyl |
| 407 | CH₂CH₂O | 4-methyl-3-isothiazolyl |
| 408 | CH₂CH₂O | 5-methyl-3-isothiazolyl |
| 409 | CH₂CH₂O | 4-isothiazolyl |
| 410 | CH₂CH₂O | 3-methyl-4-isothiazolyl |
| 411 | CH₂CH₂O | 5-methyl-4-isothiazolyl |
| 412 | CH₂CH₂O | 5-isothiazolyl |
| 413 | CH₂CH₂O | 3-methyl-5-isothiazolyl |
| 414 | CH₂CH₂O | 4-methyl-5-isothiazolyl |
| 415 | CH₂CH₂O | 2-oxazolyl |
| 416 | CH₂CH₂O | 4-oxazolyl |
| 417 | CH₂CH₂O | 5-oxazolyl |
| 418 | CH₂CH₂O | 2-thiazolyl |
| 419 | CH₂CH₂O | 4-thiazolyl |
| 420 | CH₂CH₂O | 5-thiazolyl |
| 421 | CH₂CH₂O | 3-pyrazolyl |
| 422 | CH₂CH₂O | 4-pyrazolyl |
| 423 | CH₂CH₂O | 1-methyl-3-pyrazolyl |
| 424 | CH₂CH₂O | 1-methyl-4-pyrazolyl |
| 425 | CH₂CH₂O | 1-methyl-5-pyrazolyl |
| 426 | CH₂CH₂O | 2-imidazolyl |
| 427 | CH₂CH₂O | 1-methyl-2-imidazolyl |
| 428 | CH₂CH₂O | 5-methyl-[1,3,4]-2-oxadiazolyl |
| 429 | CH₂CH₂O | 5-methyl-[1,2,4]-3-oxadiazolyl |
| 430 | CH₂CH₂O | 5-methyl-[1,3,4]-2-thiadiazolyl |
| 431 | CH₂CH₂O | 5-methyl-[1,2,4]-3-thiadiazolyl |
| 432 | CH₂CH₂O | [1,2,4]-3-triazolyl |
| 433 | CH₂CH₂O | [1,2,3]-4-triazolyl |
| 434 | CH₂CH₂O | 2-pyridyl |
| 435 | CH₂CH₂O | 6-chloro-2-pyridyl |
| 436 | CH₂CH₂O | 6-methoxy-2-pyridyl |
| 437 | CH₂CH₂O | 6-trifluoromethyl-2-pyridyl |
| 438 | CH₂CH₂O | 3-pyridyl |
| 439 | CH₂CH₂O | 2-chloro-3-pyridyl |
| 440 | CH₂CH₂O | 2-methoxy-3-pyridyl |
| 441 | CH₂CH₂O | 4-pyridyl |
| 442 | CH₂CH₂O | 2-chloro-4-pyridyl |
| 443 | CH₂CH₂O | 2-methoxy-4-pyridyl |
| 444 | CH₂CH₂O | 2-ethoxy-4-pyridyl |
| 445 | CH₂CH₂O | 2-methylthio-4-pyridyl |
| 446 | CH₂CH₂O | 2-trifluoromethyl-5-pyridyl |
| 447 | CH₂CH₂O | 2-pyrimidinyl |
| 448 | CH₂CH₂O | 3-pyrimidinyl |
| 449 | CH₂CH₂O | 4-pyrimidinyl |
| 450 | CH₂CH₂O | 2-pyrazinyl |
| 451 | CH₂CH₂O | 3-pyridazinyl |
| 452 | CH₂CH₂O | 4-pyridazinyl |
| 453 | CH₂CH₂O | 2-(2H-1,3-oxazinyl) |
| 454 | CH₂CH₂O | 2-(6H-1,3-oxazinyl) |
| 455 | CH₂CH₂O | 4-(6H-1,3-oxazinyl) |
| 456 | CH₂CH₂O | 6-(6H-1,3-oxazinyl) |
| 457 | CH₂CH₂O | [1,3,5]-2-triazinyl |
| 458 | CH₂CH₂O | [1,2,4]-3-triazinyl |
| 459 | CH₂CH₂O | [1,2,4]-5-triazinyl |
| 460 | CH₂CH₂O | [1,2,4]-6-triazinyl |
| 461 | CH₂OCH₂ | oxiranyl |
| 462 | CH₂OCH₂ | 3-methyl-2-oxiranyl |
| 463 | CH₂OCH₂ | 2-oxetanyl |
| 464 | CH₂OCH₂ | 3-hydroxy-3-methyl-2-oxetanyl |
| 465 | CH₂OCH₂ | 3-hydroxy-3-ethyl-2-oxetanyl |
| 466 | CH₂OCH₂ | 3-hydroxy-3-propyl-2-oxetanyl |
| 467 | CH₂OCH₂ | 3-hydroxy-3-butyl-2-oxetanyl |
| 468 | CH₂OCH₂ | 3-methoxy-3-methyl-2-oxetanyl |
| 469 | CH₂OCH₂ | 3-methoxy-3-ethyl-2-oxetanyl |
| 470 | CH₂OCH₂ | 3-methoxy-3-propyl-2-oxetanyl |
| 471 | CH₂OCH₂ | 3-methoxy-3-butyl-2-oxetanyl |
| 472 | CH₂OCH₂ | 3-trimethylsilyloxy-3-methyl-2-oxetanyl |
| 473 | CH₂OCH₂ | 3-trimethylsilyloxy-3-ethyl-2-oxetanyl |
| 474 | CH₂OCH₂ | 3-trimethylsilyloxy-3-propyl-2-oxetanyl |
| 475 | CH₂OCH₂ | 3-trimethylsilyloxy-3-butyl-2-oxetanyl |
| 476 | CH₂OCH₂ | 3-oxetanyl |
| 477 | CH₂OCH₂ | 2-furyl |
| 478 | CH₂OCH₂ | 4,5-dihydro-2-furyl |
| 479 | CH₂OCH₂ | 2,3-dihydro-2-furyl |
| 480 | CH₂OCH₂ | 3-furyl |
| 481 | CH₂OCH₂ | 4,5-dihydro-3-furyl |
| 482 | CH₂OCH₂ | 2,3-dihydro-3-furyl |
| 483 | CH₂OCH₂ | 2-thienyl |
| 484 | CH₂OCH₂ | 4,5-dihydro-2-thienyl |
| 485 | CH₂OCH₂ | 2,3-dihydro-2-thienyl |
| 486 | CH₂OCH₂ | 5-chloro-2-thienyl |
| 487 | CH₂OCH₂ | 5-methyl-2-thienyl |
| 488 | CH₂OCH₂ | 3-thienyl |
| 489 | CH₂OCH₂ | 4,5-dihydro-3-thienyl |
| 490 | CH₂OCH₂ | 2,3-dihydro-3-thienyl |
| 491 | CH₂OCH₂ | 2-pyrrolyl |
| 492 | CH₂OCH₂ | 2,5-dihydro-2-pyrrolyl |
| 493 | CH₂OCH₂ | 3-pyrrolyl |
| 494 | CH₂OCH₂ | 2,5-dihydro-3-pyrrolyl |
| 495 | CH₂OCH₂ | 3-isoxazolyl |
| 496 | CH₂OCH₂ | 4-methyl-3-isoxazolyl |
| 497 | CH₂OCH₂ | 5-methyl-3-isoxazolyl |
| 498 | CH₂OCH₂ | 4,5-dimethyl-3-isoxazolyl |
| 499 | CH₂OCH₂ | 4,5-dihydro-3-isoxazolyl |
| 500 | CH₂OCH₂ | 4-methyl-4,5-dihydro-3-isoxazolyl |
| 501 | CH₂OCH₂ | 5-methyl-4,5-dihydro-3-isoxazolyl |
| 502 | CH₂OCH₂ | 4,5-dimethyl-4,5-dihydro-3-isoxazolyl |
| 503 | CH₂OCH₂ | 4-isoxazolyl |
| 504 | CH₂OCH₂ | 3-methyl-4-isoxazolyl |
| 505 | CH₂OCH₂ | 5-methyl-4-isoxazolyl |
| 506 | CH₂OCH₂ | 5-cyclopropyl-4-isoxazolyl |
| 507 | CH₂OCH₂ | 5-phenyl-4-isoxazolyl |
| 508 | CH₂OCH₂ | 3,5-dimethyl-4-isoxazolyl |
| 509 | CH₂OCH₂ | 4,5-dihydro-4-isoxazolyl |
| 510 | CH₂OCH₂ | 3-methyl-4,5-dihydro-4-isoxazolyl |
| 511 | CH₂OCH₂ | 5-methyl-4,5-dihydro-4-isoxazolyl |
| 512 | CH₂OCH₂ | 3,5-dimethyl-4,5-dihydro-4-isoxazolyl |
| 513 | CH₂OCH₂ | 5-isoxazolyl |
| 514 | CH₂OCH₂ | 3-methyl-5-isoxazolyl |
| 515 | CH₂OCH₂ | 4-methyl-5-isoxazolyl |
| 516 | CH₂OCH₂ | 3,4-dimethyl-5-isoxazolyl |
| 517 | CH₂OCH₂ | 4,5-dihydro-5-isoxazolyl |
| 518 | CH₂OCH₂ | 3-methyl-4,5-dihydro-5-isoxazolyl |
| 519 | CH₂OCH₂ | 4-methyl-4,5-dihydro-5-isoxazolyl |
| 520 | CH₂OCH₂ | 3,4-dimethyl-4,5-dihydro-5-isoxazolyl |
| 521 | CH₂OCH₂ | 3-isothiazolyl |
| 522 | CH₂OCH₂ | 4-methyl-3-isothiazolyl |
| 523 | CH₂OCH₂ | 5-methyl-3-isothiazolyl |
| 524 | CH₂OCH₂ | 4-isothiazolyl |
| 525 | CH₂OCH₂ | 3-methyl-4-isothiazolyl |
| 526 | CH₂OCH₂ | 5-methyl-4-isothiazolyl |
| 527 | CH₂OCH₂ | 5-isothiazolyl |

TABLE A-continued

| No. | X¹ | Het |
|---|---|---|
| 528 | CH$_2$OCH$_2$ | 3-methyl-5-isothiazolyl |
| 529 | CH$_2$OCH$_2$ | 4-methyl-5-isothiazolyl |
| 530 | CH$_2$OCH$_2$ | 2-oxazolyl |
| 531 | CH$_2$OCH$_2$ | 4-oxazolyl |
| 532 | CH$_2$OCH$_2$ | 5-oxazolyl |
| 533 | CH$_2$OCH$_2$ | 2-thiazolyl |
| 534 | CH$_2$OCH$_2$ | 4-thiazolyl |
| 535 | CH$_2$OCH$_2$ | 5-thiazolyl |
| 536 | CH$_2$OCH$_2$ | 3-pyrazolyl |
| 537 | CH$_2$OCH$_2$ | 4-pyrazolyl |
| 538 | CH$_2$OCH$_2$ | 1-methyl-3-pyrazolyl |
| 539 | CH$_2$OCH$_2$ | 1-methyl-4-pyrazolyl |
| 540 | CH$_2$OCH$_2$ | 1-methyl-5-pyrazolyl |
| 541 | CH$_2$OCH$_2$ | 2-imidazolyl |
| 542 | CH$_2$OCH$_2$ | 1-methyl-2-imidazolyl |
| 543 | CH$_2$OCH$_2$ | 5-methyl-[1,3,4]-2-oxadiazolyl |
| 544 | CH$_2$OCH$_2$ | 5-methyl-[1,2,4]-3-oxadiazolyl |
| 545 | CH$_2$OCH$_2$ | 5-methyl-[1,3,4]-2-thiadiazolyl |
| 546 | CH$_2$OCH$_2$ | 5-methyl-[1,2,4]-3-thiadiazolyl |
| 547 | CH$_2$OCH$_2$ | [1,2,4]-3-triazolyl |
| 548 | CH$_2$OCH$_2$ | [1,2,3]-4-triazolyl |
| 549 | CH$_2$OCH$_2$ | 2-pyridyl |
| 550 | CH$_2$OCH$_2$ | 6-chloro-2-pyridyl |
| 551 | CH$_2$OCH$_2$ | 6-methoxy-2-pyridyl |
| 552 | CH$_2$OCH$_2$ | 6-trifluoromethyl-2-pyridyl |
| 553 | CH$_2$OCH$_2$ | 3-pyridyl |
| 554 | CH$_2$OCH$_2$ | 2-chloro-3-pyridyl |
| 555 | CH$_2$OCH$_2$ | 2-methoxy-3-pyridyl |
| 556 | CH$_2$OCH$_2$ | 4-pyridyl |
| 557 | CH$_2$OCH$_2$ | 2-chloro-4-pyridyl |
| 558 | CH$_2$OCH$_2$ | 2-methoxy-4-pyridyl |
| 559 | CH$_2$OCH$_2$ | 2-ethoxy-4-pyridyl |
| 560 | CH$_2$OCH$_2$ | 2-methylthio-4-pyridyl |
| 561 | CH$_2$OCH$_2$ | 2-trifluoromethyl-5-pyridyl |
| 562 | CH$_2$OCH$_2$ | 2-pyrimidinyl |
| 563 | CH$_2$OCH$_2$ | 3-pyrimidinyl |
| 564 | CH$_2$OCH$_2$ | 4-pyrimidinyl |
| 565 | CH$_2$OCH$_2$ | 2-pyrazinyl |
| 566 | CH$_2$OCH$_2$ | 3-pyridazinyl |
| 567 | CH$_2$OCH$_2$ | 4-pyridazinyl |
| 568 | CH$_2$OCH$_2$ | 2-(2H-1,3-oxazinyl) |
| 569 | CH$_2$OCH$_2$ | 2-(6H-1,3-oxazinyl) |
| 570 | CH$_2$OCH$_2$ | 4-(6H-1,3-oxazinyl) |
| 571 | CH$_2$OCH$_2$ | 6-(6H-1,3-oxazinyl) |
| 572 | CH$_2$OCH$_2$ | [1,3,5]-2-triazinyl |
| 573 | CH$_2$OCH$_2$ | [1,2,4]-3-triazinyl |
| 574 | CH$_2$OCH$_2$ | [1,2,4]-5-triazinyl |
| 575 | CH$_2$OCH$_2$ | [1,2,4]-6-triazinyl |
| 576 | CH$_2$OCH$_2$CH=CH | oxiranyl |
| 577 | CH$_2$OCH$_2$CH=CH | 3-methyl-2-oxiranyl |
| 578 | CH$_2$OCH$_2$CH=CH | 2-oxetanyl |
| 579 | CH$_2$OCH$_2$CH=CH | 3-hydroxy-3-methyl-2-oxetanyl |
| 580 | CH$_2$OCH$_2$CH=CH | 3-hydroxy-3-ethyl-2-oxetanyl |
| 581 | CH$_2$OCH$_2$CH=CH | 3-hydroxy-3-propyl-2-oxetanyl |
| 582 | CH$_2$OCH$_2$CH=CH | 3-hydroxy-3-butyl-2-oxetanyl |
| 583 | CH$_2$OCH$_2$CH=CH | 3-methoxy-3-methyl-2-oxetanyl |
| 584 | CH$_2$OCH$_2$CH=CH | 3-methoxy-3-ethyl-2-oxetanyl |
| 585 | CH$_2$OCH$_2$CH=CH | 3-methoxy-3-propyl-2-oxetanyl |
| 586 | CH$_2$OCH$_2$CH=CH | 3-methoxy-3-butyl-2-oxetanyl |
| 587 | CH$_2$OCH$_2$CH=CH | 3-trimethyl-silyloxy-3-methyl-2-oxetanyl |
| 588 | CH$_2$OCH$_2$CH=CH | 3-trimethyl-silyloxy-3-ethyl-2-oxetanyl |
| 589 | CH$_2$OCH$_2$CH=CH | 3-trimethyl-silyloxy-3-propyl-2-oxetanyl |
| 590 | CH$_2$OCH$_2$CH=CH | 3-trimethyl-silyloxy-3-butyl-2-oxetanyl |
| 591 | CH$_2$OCH$_2$CH=CH | 3-oxetanyl |
| 592 | CH$_2$OCH$_2$CH=CH | 2-furyl |
| 593 | CH$_2$OCH$_2$CH=CH | 4,5-dihydro-2-furyl |
| 594 | CH$_2$OCH$_2$CH=CH | 2,3-dihydro-2-furyl |
| 595 | CH$_2$OCH$_2$CH=CH | 3-furyl |
| 596 | CH$_2$OCH$_2$CH=CH | 4,5-dihydro-3-furyl |
| 597 | CH$_2$OCH$_2$CH=CH | 2,3-dihydro-3-furyl |
| 598 | CH$_2$OCH$_2$CH=CH | 2-thienyl |
| 599 | CH$_2$OCH$_2$CH=CH | 4,5-dihydro-2-thienyl |
| 600 | CH$_2$OCH$_2$CH=CH | 2,3-dihydro-2-thienyl |
| 601 | CH$_2$OCH$_2$CH=CH | 5-chloro-2-thienyl |
| 602 | CH$_2$OCH$_2$CH=CH | 5-methyl-2-thienyl |
| 603 | CH$_2$OCH$_2$CH=CH | 3-thienyl |
| 604 | CH$_2$OCH$_2$CH=CH | 4,5-dihydro-3-thienyl |
| 605 | CH$_2$OCH$_2$CH=CH | 2,3-dihydro-3-thienyl |
| 606 | CH$_2$OCH$_2$CH=CH | 2-pyrrolyl |
| 607 | CH$_2$OCH$_2$CH=CH | 2,5-dihydro-2-pyrrolyl |
| 608 | CH$_2$OCH$_2$CH=CH | 3-pyrrolyl |
| 609 | CH$_2$OCH$_2$CH=CH | 2,5-dihydro-3-pyrrolyl |
| 610 | CH$_2$OCH$_2$CH=CH | 3-isoxazolyl |
| 611 | CH$_2$OCH$_2$CH=CH | 4-methyl-3-isoxazolyl |
| 612 | CH$_2$OCH$_2$CH=CH | 5-methyl-3-isoxazolyl |
| 613 | CH$_2$OCH$_2$CH=CH | 4,5-dimethyl-3-isoxazolyl |
| 614 | CH$_2$OCH$_2$CH=CH | 4,5-dihydro-3-isoxazolyl |
| 615 | CH$_2$OCH$_2$CH=CH | 4-methyl-4,5-dihydro-3-isoxazolyl |
| 616 | CH$_2$OCH$_2$CH=CH | 5-methyl-4,5-dihydro-3-isoxazolyl |
| 617 | CH$_2$OCH$_2$CH=CH | 4,5-dimethyl-4,5-dihydro-3-isoxazolyl |
| 618 | CH$_2$OCH$_2$CH=CH | 4-isoxazolyl |
| 619 | CH$_2$OCH$_2$CH=CH | 3-methyl-4-isoxazolyl |
| 620 | CH$_2$OCH$_2$CH=CH | 5-methyl-4-isoxazolyl |
| 621 | CH$_2$OCH$_2$CH=CH | 5-cyclopropyl-4-isoxazolyl |
| 622 | CH$_2$OCH$_2$CH=CH | 5-phenyl-4-isoxazolyl |
| 623 | CH$_2$OCH$_2$CH=CH | 3,5-dimethyl-4-isoxazolyl |
| 624 | CH$_2$OCH$_2$CH=CH | 4,5-dihydro-4-isoxazolyl |
| 625 | CH$_2$OCH$_2$CH=CH | 3-methyl-4,5-dihydro-4-isoxazolyl |
| 626 | CH$_2$OCH$_2$CH=CH | 5-methyl-4,5-dihydro-4-isoxazolyl |
| 627 | CH$_2$OCH$_2$CH=CH | 3,5-dimethyl-4,5-dihydro-4-isoxazolyl |
| 628 | CH$_2$OCH$_2$CH=CH | 5-isoxazolyl |
| 629 | CH$_2$OCH$_2$CH=CH | 3-methyl-5-isoxazolyl |
| 630 | CH$_2$OCH$_2$CH=CH | 4-methyl-5-isoxazolyl |
| 631 | CH$_2$OCH$_2$CH=CH | 3,4-dimethyl-5-isoxazolyl |
| 632 | CH$_2$OCH$_2$CH=CH | 4,5-dihydro-5-isoxazolyl |
| 633 | CH$_2$OCH$_2$CH=CH | 3-methyl-4,5-dihydro-5-isoxazolyl |
| 634 | CH$_2$OCH$_2$CH=CH | 4-methyl-4,5-dihydro-5-isoxazolyl |
| 635 | CH$_2$OCH$_2$CH=CH | 3,4-dimethyl-4,5-dihydro-5-isoxazolyl |
| 636 | CH$_2$OCH$_2$CH=CH | 3-isothiazolyl |
| 637 | CH$_2$OCH$_2$CH=CH | 4-methyl-3-isothiazolyl |
| 638 | CH$_2$OCH$_2$CH=CH | 5-methyl-3-isothiazolyl |
| 639 | CH$_2$OCH$_2$CH=CH | 4-isothiazolyl |
| 640 | CH$_2$OCH$_2$CH=CH | 3-methyl-4-isothiazolyl |
| 641 | CH$_2$OCH$_2$CH=CH | 5-methyl-4-isothiazolyl |
| 642 | CH$_2$OCH$_2$CH=CH | 5-isothiazolyl |
| 643 | CH$_2$OCH$_2$CH=CH | 3-methyl-5-isothiazolyl |
| 644 | CH$_2$OCH$_2$CH=CH | 4-methyl-5-isothiazolyl |
| 645 | CH$_2$OCH$_2$CH=CH | 2-oxazolyl |
| 646 | CH$_2$OCH$_2$CH=CH | 4-oxazolyl |
| 647 | CH$_2$OCH$_2$CH=CH | 5-oxazolyl |
| 648 | CH$_2$OCH$_2$CH=CH | 2-thiazolyl |
| 649 | CH$_2$OCH$_2$CH=CH | 4-thiazolyl |
| 650 | CH$_2$OCH$_2$CH=CH | 5-thiazolyl |
| 651 | CH$_2$OCH$_2$CH=CH | 3-pyrazolyl |
| 652 | CH$_2$OCH$_2$CH=CH | 4-pyrazolyl |
| 653 | CH$_2$OCH$_2$CH=CH | 1-methyl-3-pyrazolyl |

TABLE A-continued

| No. | X¹ | Het |
|---|---|---|
| 654 | CH₂OCH₂CH=CH | 1-methyl-4-pyrazolyl |
| 655 | CH₂OCH₂CH=CH | 1-methyl-5-pyrazolyl |
| 656 | CH₂OCH₂CH=CH | 2-imidazolyl |
| 657 | CH₂OCH₂CH=CH | 1-methyl-2-imidazolyl |
| 658 | CH₂OCH₂CH=CH | 5-methyl-[1,3,4]-2-oxadiazolyl |
| 659 | CH₂OCH₂CH=CH | 5-methyl-[1,2,4]-3-oxadiazolyl |
| 660 | CH₂OCH₂CH=CH | 5-methyl-[1,3,4]-2-thiadiazolyl |
| 661 | CH₂OCH₂CH=CH | 5-methyl-[1,2,4]-3-thiadiazolyl |
| 662 | CH₂OCH₂CH=CH | [1,2,4]-3-triazolyl |
| 663 | CH₂OCH₂CH=CH | [1,2,3]-4-triazolyl |
| 664 | CH₂OCH₂CH=CH | 2-pyridyl |
| 665 | CH₂OCH₂CH=CH | 6-chloro-2-pyridyl |
| 666 | CH₂OCH₂CH=CH | 6-methoxy-2-pyridyl |
| 667 | CH₂OCH₂CH=CH | 6-trifluoromethyl-2-pyridyl |
| 668 | CH₂OCH₂CH=CH | 3-pyridyl |
| 669 | CH₂OCH₂CH=CH | 2-chloro-3-pyridyl |
| 670 | CH₂OCH₂CH=CH | 2-methoxy-3-pyridyl |
| 671 | CH₂OCH₂CH=CH | 4-pyridyl |
| 672 | CH₂OCH₂CH=CH | 2-chloro-4-pyridyl |
| 673 | CH₂OCH₂CH=CH | 2-methoxy-4-pyridyl |
| 674 | CH₂OCH₂CH=CH | 2-ethoxy-4-pyridyl |
| 675 | CH₂OCH₂CH=CH | 2-methylthio-4-pyridyl |
| 676 | CH₂OCH₂CH=CH | 2-trifluoromethyl-5-pyridyl |
| 677 | CH₂OCH₂CH=CH | 2-pyrimidinyl |
| 678 | CH₂OCH₂CH=CH | 3-pyrimidinyl |
| 679 | CH₂OCH₂CH=CH | 4-pyrimidinyl |
| 680 | CH₂OCH₂CH=CH | 2-pyrazinyl |
| 681 | CH₂OCH₂CH=CH | 3-pyridazinyl |
| 682 | CH₂OCH₂CH=CH | 4-pyridazinyl |
| 683 | CH₂OCH₂CH=CH | 2-(2H-1,3-oxazinyl) |
| 684 | CH₂OCH₂CH=CH | 2-(6H-1,3-oxazinyl) |
| 685 | CH₂OCH₂CH=CH | 4-(6H-1,3-oxazinyl) |
| 686 | CH₂OCH₂CH=CH | 6-(6H-1,3-oxazinyl) |
| 687 | CH₂OCH₂CH=CH | [1,3,5]-2-triazinyl |
| 688 | CH₂OCH₂CH=CH | [1,2,4]-3-triazinyl |
| 689 | CH₂OCH₂CH=CH | [1,2,4]-5-triazinyl |
| 690 | CH₂OCH₂CH=CH | [1,2,4]-6-triazinyl |
| 691 | CH=CHCH₂O | oxiranyl |
| 692 | CH=CHCH₂O | 3-methyl-2-oxiranyl |
| 693 | CH=CHCH₂O | 2-oxetanyl |
| 694 | CH=CHCH₂O | 3-hydroxy-3-methyl-2-oxetanyl |
| 695 | CH=CHCH₂O | 3-hydroxy-3-ethyl-2-oxetanyl |
| 696 | CH=CHCH₂O | 3-hydroxy-3-propyl-2-oxetanyl |
| 697 | CH=CHCH₂O | 3-hydroxy-3-butyl-2-oxetanyl |
| 698 | CH=CHCH₂O | 3-methoxy-3-methyl-2-oxetanyl |
| 699 | CH=CHCH₂O | 3-methoxy-3-ethyl-2-oxetanyl |
| 700 | CH=CHCH₂O | 3-methoxy-3-propyl-2-oxetanyl |
| 701 | CH=CHCH₂O | 3-methoxy-3-butyl-2-oxetanyl |
| 702 | CH=CHCH₂O | 3-trimethylsilyloxy-3-methyl-2-oxetanyl |
| 703 | CH=CHCH₂O | 3-trimethylsilyloxy-3-ethyl-2-oxetanyl |
| 704 | CH=CHCH₂O | 3-trimethylsilyloxy-3-propyl-2-oxetanyl |
| 705 | CH=CHCH₂O | 3-trimethylsilyloxy-3-butyl-2-oxetanyl |
| 706 | CH=CHCH₂O | 3-oxetanyl |
| 707 | CH=CHCH₂O | 2-furyl |
| 708 | CH=CHCH₂O | 4,5-dihydro-2-furyl |
| 709 | CH=CHCH₂O | 2,3-dihydro-2-furyl |
| 710 | CH=CHCH₂O | 3-furyl |
| 711 | CH=CHCH₂O | 4,5-dihydro-3-furyl |
| 712 | CH=CHCH₂O | 2,3-dihydro-3-furyl |
| 713 | CH=CHCH₂O | 2-thienyl |
| 714 | CH=CHCH₂O | 4,5-dihydro-2-thienyl |
| 715 | CH=CHCH₂O | 2,3-dihydro-2-thienyl |
| 716 | CH=CHCH₂O | 5-chloro-2-thienyl |
| 717 | CH=CHCH₂O | 5-methyl-2-thienyl |
| 718 | CH=CHCH₂O | 3-thienyl |
| 719 | CH=CHCH₂O | 4,5-dihydro-3-thienyl |
| 720 | CH=CHCH₂O | 2,3-dihydro-3-thienyl |
| 721 | CH=CHCH₂O | 2-pyrrolyl |
| 722 | CH=CHCH₂O | 2,5-dihydro-2-pyrrolyl |
| 723 | CH=CHCH₂O | 3-pyrrolyl |
| 724 | CH=CHCH₂O | 2,5-dihydro-3-pyrrolyl |
| 725 | CH=CHCH₂O | 3-isoxazolyl |
| 726 | CH=CHCH₂O | 4-methyl-3-isoxazolyl |
| 727 | CH=CHCH₂O | 5-methyl-3-isoxazolyl |
| 728 | CH=CHCH₂O | 4,5-dimethyl-3-isoxazolyl |
| 729 | CH=CHCH₂O | 4,5-dihydro-3-isoxazolyl |
| 730 | CH=CHCH₂O | 4-methyl-4,5-dihydro-3-isoxazolyl |
| 731 | CH=CHCH₂O | 5-methyl-4,5-dihydro-3-isoxazolyl |
| 732 | CH=CHCH₂O | 4,5-dimethyl-4,5-dihydro-3-isoxazolyl |
| 733 | CH=CHCH₂O | 4-isoxazolyl |
| 734 | CH=CHCH₂O | 3-methyl-4-isoxazolyl |
| 735 | CH=CHCH₂O | 5-methyl-4-isoxazolyl |
| 736 | CH=CHCH₂O | 5-cyclopropyl-4-isoxazolyl |
| 737 | CH=CHCH₂O | 5-phenyl-4-isoxazolyl |
| 738 | CH=CHCH₂O | 3,5-dimethyl-4-isoxazolyl |
| 739 | CH=CHCH₂O | 4,5-dihydro-4-isoxazolyl |
| 740 | CH=CHCH₂O | 3-methyl-4,5-dihydro-4-isoxazolyl |
| 741 | CH=CHCH₂O | 5-methyl-4,5-dihydro-4-isoxazolyl |
| 742 | CH=CHCH₂O | 3,5-dimethyl-4,5-dihydro-4-isoxazolyl |
| 743 | CH=CHCH₂O | 5-isoxazolyl |
| 744 | CH=CHCH₂O | 3-methyl-5-isoxazolyl |
| 745 | CH=CHCH₂O | 4-methyl-5-isoxazolyl |
| 746 | CH=CHCH₂O | 3,4-dimethyl-5-isoxazolyl |
| 747 | CH=CHCH₂O | 4,5-dihydro-5-isoxazolyl |
| 748 | CH=CHCH₂O | 3-methyl-4,5-dihydro-5-isoxazolyl |
| 749 | CH=CHCH₂O | 4-methyl-4,5-dihydro-5-isoxazolyl |
| 750 | CH=CHCH₂O | 3,4-dimethyl-4,5-dihydro-5-isoxazolyl |
| 751 | CH=CHCH₂O | 3-isothiazolyl |
| 752 | CH=CHCH₂O | 4-methyl-3-isothiazolyl |
| 753 | CH=CHCH₂O | 5-methyl-3-isothiazolyl |
| 754 | CH=CHCH₂O | 4-isothiazolyl |
| 755 | CH=CHCH₂O | 3-methyl-4-isothiazolyl |
| 756 | CH=CHCH₂O | 5-methyl-4-isothiazolyl |
| 757 | CH=CHCH₂O | 5-isothiazolyl |
| 758 | CH=CHCH₂O | 3-methyl-5-isothiazolyl |
| 759 | CH=CHCH₂O | 4-methyl-5-isothiazolyl |
| 760 | CH=CHCH₂O | 2-oxazolyl |
| 761 | CH=CHCH₂O | 4-oxazolyl |
| 762 | CH=CHCH₂O | 5-oxazolyl |
| 763 | CH=CHCH₂O | 2-thiazolyl |
| 764 | CH=CHCH₂O | 4-thiazolyl |
| 765 | CH=CHCH₂O | 5-thiazolyl |
| 766 | CH=CHCH₂O | 3-pyrazolyl |
| 767 | CH=CHCH₂O | 4-pyrazolyl |
| 768 | CH=CHCH₂O | 1-methyl-3-pyrazolyl |
| 769 | CH=CHCH₂O | 1-methyl-4-pyrazolyl |
| 770 | CH=CHCH₂O | 1-methyl-5-pyrazolyl |
| 771 | CH=CHCH₂O | 2-imidazolyl |
| 772 | CH=CHCH₂O | 1-methyl-2-imidazolyl |
| 773 | CH=CHCH₂O | 5-methyl-[1,3,4]-2-oxadiazolyl |
| 774 | CH=CHCH₂O | 5-methyl-[1,2,4]-3-oxadiazolyl |
| 775 | CH=CHCH₂O | 5-methyl-[1,3,4]-2-thiadiazolyl |
| 776 | CH=CHCH₂O | 5-methyl-[1,2,4]-3-thiadiazolyl |

TABLE A-continued

| No. | X¹ | Het |
|---|---|---|
| 777 | CH=CHCH₂O | [1,2,4]-3-triazolyl |
| 778 | CH=CHCH₂O | [1,2,3]-4-triazolyl |
| 779 | CH=CHCH₂O | 2-pyridyl |
| 780 | CH=CHCH₂O | 6-chloro-2-pyridyl |
| 781 | CH=CHCH₂O | 6-methoxy-2-pyridyl |
| 782 | CH=CHCH₂O | 6-trifluoromethyl-2-pyridyl |
| 783 | CH=CHCH₂O | 3-pyridyl |
| 784 | CH=CHCH₂O | 2-chloro-3-pyridyl |
| 785 | CH=CHCH₂O | 2-methoxy-3-pyridyl |
| 786 | CH=CHCH₂O | 4-pyridyl |
| 787 | CH=CHCH₂O | 2-chloro-4-pyridyl |
| 788 | CH=CHCH₂O | 2-methoxy-4-pyridyl |
| 789 | CH=CHCH₂O | 2-ethoxy-4-pyridyl |
| 790 | CH=CHCH₂O | 2-methylthio-4-pyridyl |
| 791 | CH=CHCH₂O | 2-trifluoromethyl-5-pyridyl |
| 792 | CH=CHCH₂O | 2-pyrimidinyl |
| 793 | CH=CHCH₂O | 3-pyrimidinyl |
| 794 | CH=CHCH₂O | 4-pyrimidinyl |
| 795 | CH=CHCH₂O | 2-pyrazinyl |
| 796 | CH=CHCH₂O | 3-pyridazinyl |
| 797 | CH=CHCH₂O | 4-pyridazinyl |
| 798 | CH=CHCH₂O | 2-(2H-1,3-oxazinyl) |
| 799 | CH=CHCH₂O | 2-(6H-1,3-oxazinyl) |
| 800 | CH=CHCH₂O | 4-(6H-1,3-oxazinyl) |
| 801 | CH=CHCH₂O | 6-(6H-1,3-oxazinyl) |
| 802 | CH=CHCH₂O | [1,3,5]-2-triazinyl |
| 803 | CH=CHCH₂O | [1,2,4]-3-triazinyl |
| 804 | CH=CHCH₂O | [1,2,4]-5-triazinyl |
| 805 | CH=CHCH₂O | [1,2,4]-6-triazinyl |
| 806 | —C≡C—CH₂O | oxiranyl |
| 807 | —C≡C—CH₂O | 3-methyl-2-oxiranyl |
| 808 | —C≡C—CH₂O | 2-oxetanyl |
| 809 | —C≡C—CH₂O | 3-hydroxy-3-methyl-2-oxetanyl |
| 810 | —C≡C—CH₂O | 3-hydroxy-3-ethyl-2-oxetanyl |
| 811 | —C≡C—CH₂O | 3-hydroxy-3-propyl-2-oxetanyl |
| 812 | —C≡C—CH₂O | 3-hydroxy-3-butyl-2-oxetanyl |
| 813 | —C≡C—CH₂O | 3-methoxy-3-methyl-2-oxetanyl |
| 814 | —C≡C—CH₂O | 3-methoxy-3-ethyl-2-oxetanyl |
| 815 | —C≡C—CH₂O | 3-methoxy-3-propyl-2-oxetanyl |
| 816 | —C≡C—CH₂O | 3-methoxy-3-butyl-2-oxetanyl |
| 817 | —C≡C—CH₂O | 3-trimethyl-silyloxy-3-methyl-2-oxetanyl |
| 818 | —C≡C—CH₂O | 3-trimethyl-silyloxy-3-ethyl-2-oxetanyl |
| 819 | —C≡C—CH₂O | 3-trimethyl-silyloxy-3-propyl-2-oxetanyl |
| 820 | —C≡C—CH₂O | 3-trimethyl-silyloxy-3-butyl-2-oxetanyl |
| 821 | —C≡C—CH₂O | 3-oxetanyl |
| 822 | —C≡C—CH₂O | 2-furyl |
| 823 | —C≡C—CH₂O | 4,5-dihydro-2-furyl |
| 824 | —C≡C—CH₂O | 2,3-dihydro-2-furyl |
| 825 | —C≡C—CH₂O | 3-furyl |
| 826 | —C≡C—CH₂O | 4,5-dihydro-3-furyl |
| 827 | —C≡C—CH₂O | 2,3-dihydro-3-furyl |
| 828 | —C≡C—CH₂O | 2-thienyl |
| 829 | —C≡C—CH₂O | 4,5-dihydro-2-thienyl |
| 830 | —C≡C—CH₂O | 2,3-dihydro-2-thienyl |
| 831 | —C≡C—CH₂O | 5-chloro-2-thienyl |
| 832 | —C≡C—CH₂O | 5-methyl-2-thienyl |
| 833 | —C≡C—CH₂O | 3-thienyl |
| 834 | —C≡C—CH₂O | 4,5-dihydro-3-thienyl |
| 835 | —C≡C—CH₂O | 2,3-dihydro-3-thienyl |
| 836 | —C≡C—CH₂O | 2-pyrrolyl |
| 837 | —C≡C—CH₂O | 2,5-dihydro-2-pyrrolyl |
| 838 | —C≡C—CH₂O | 3-pyrrolyl |
| 839 | —C≡C—CH₂O | 2,5-dihydro-3-pyrrolyl |
| 840 | —C≡C—CH₂O | 3-isoxazolyl |
| 841 | —C≡C—CH₂O | 4-methyl-3-isoxazolyl |
| 842 | —C≡C—CH₂O | 5-methyl-3-isoxazolyl |
| 843 | —C≡C—CH₂O | 4,5-dimethyl-3-isoxazolyl |
| 844 | —C≡C—CH₂O | 4,5-dihydro-3-isoxazolyl |
| 845 | —C≡C—CH₂O | 4-methyl-4,5-dihydro-3-isoxazolyl |
| 846 | —C≡C—CH₂O | 5-methyl-4,5-dihydro-3-isoxazolyl |
| 847 | —C≡C—CH₂O | 4,5-dimethyl-4,5-dihydro-3-isoxazolyl |
| 848 | —C≡C—CH₂O | 4-isoxazolyl |
| 849 | —C≡C—CH₂O | 3-methyl-4-isoxazolyl |
| 850 | —C≡C—CH₂O | 5-methyl-4-isoxazolyl |
| 851 | —C≡C—CH₂O | 5-cyclopropyl-4-isoxazolyl |
| 852 | —C≡C—CH₂O | 5-phenyl-4-isoxazolyl |
| 853 | —C≡C—CH₂O | 3,5-dimethyl-4-isoxazolyl |
| 854 | —C≡C—CH₂O | 4,5-dihydro-4-isoxazolyl |
| 855 | —C≡C—CH₂O | 3-methyl-4,5-dihydro-4-isoxazolyl |
| 856 | —C≡C—CH₂O | 5-methyl-4,5-dihydro-4-isoxazolyl |
| 857 | —C≡C—CH₂O | 3,5-dimethyl-4,5-dihydro-4-isoxazolyl |
| 858 | —C≡C—CH₂O | 5-isoxazolyl |
| 859 | —C≡C—CH₂O | 3-methyl-5-isoxazolyl |
| 860 | —C≡C—CH₂O | 4-methyl-5-isoxazolyl |
| 861 | —C≡C—CH₂O | 3,4-dimethyl-5-isoxazolyl |
| 862 | —C≡C—CH₂O | 4,5-dihydro-5-isoxazolyl |
| 863 | —C≡C—CH₂O | 3-methyl-4,5-dihydro-5-isoxazolyl |
| 864 | —C≡C—CH₂O | 4-methyl-4,5-dihydro-5-isoxazolyl |
| 865 | —C≡C—CH₂O | 3,4-dimethyl-4,5-dihydro-5-isoxazolyl |
| 866 | —C≡C—CH₂O | 3-isothiazolyl |
| 867 | —C≡C—CH₂O | 4-methyl-3-isothiazolyl |
| 868 | —C≡C—CH₂O | 5-methyl-3-isothiazolyl |
| 869 | —C≡C—CH₂O | 4-isothiazolyl |
| 870 | —C≡C—CH₂O | 3-methyl-4-isothiazolyl |
| 871 | —C≡C—CH₂O | 5-methyl-4-isothiazolyl |
| 872 | —C≡C—CH₂O | 5-isothiazolyl |
| 873 | —C≡C—CH₂O | 3-methyl-5-isothiazolyl |
| 874 | —C≡C—CH₂O | 4-methyl-5-isothiazolyl |
| 875 | —C≡C—CH₂O | 2-oxazolyl |
| 876 | —C≡C—CH₂O | 4-oxazolyl |
| 877 | —C≡C—CH₂O | 5-oxazolyl |
| 878 | —C≡C—CH₂O | 2-thiazolyl |
| 879 | —C≡C—CH₂O | 4-thiazolyl |
| 880 | —C≡C—CH₂O | 5-thiazolyl |
| 881 | —C≡C—CH₂O | 3-pyrazolyl |
| 882 | —C≡C—CH₂O | 4-pyrazolyl |
| 883 | —C≡C—CH₂O | 1-methyl-3-pyrazolyl |
| 884 | —C≡C—CH₂O | 1-methyl-4-pyrazolyl |
| 885 | —C≡C—CH₂O | 1-methyl-5-pyrazolyl |
| 886 | —C≡C—CH₂O | 2-imidazolyl |
| 887 | —C≡C—CH₂O | 1-methyl-2-imidazolyl |
| 888 | —C≡C—CH₂O | 5-methyl-[1,3,4]-2-oxadiazolyl |
| 889 | —C≡C—CH₂O | 5-methyl-[1,2,4]-3-oxadiazolyl |
| 890 | —C≡C—CH₂O | 5-methyl-[1,3,4]-2-thiadiazolyl |
| 891 | —C≡C—CH₂O | 5-methyl-[1,2,4]-3-thiadiazolyl |
| 892 | —C≡C—CH₂O | [1,2,4]-3-triazolyl |
| 893 | —C≡C—CH₂O | [1,2,3]-4-triazolyl |
| 894 | —C≡C—CH₂O | 2-pyridyl |
| 895 | —C≡C—CH₂O | 6-chloro-2-pyridyl |
| 896 | —C≡C—CH₂O | 6-methoxy-2-pyridyl |
| 897 | —C≡C—CH₂O | 6-trifluoromethyl-2-pyridyl |
| 898 | —C≡C—CH₂O | 3-pyridyl |
| 899 | —C≡C—CH₂O | 2-chloro-3-pyridyl |
| 900 | —C≡C—CH₂O | 2-methoxy-3-pyridyl |
| 901 | —C≡C—CH₂O | 4-pyridyl |
| 902 | —C≡C—CH₂O | 2-chloro-4-pyridyl |

TABLE A-continued

| No. | X¹ | Het |
|---|---|---|
| 903 | —C≡C—CH₂O | 2-methoxy-4-pyridyl |
| 904 | —C≡C—CH₂O | 2-ethoxy-4-pyridyl |
| 905 | —C≡C—CH₂O | 2-methylthio-4-pyridyl |
| 906 | —C≡C—CH₂O | 2-trifluoromethyl-5-pyridyl |
| 907 | —C≡C—CH₂O | 2-pyrimidinyl |
| 908 | —C≡C—CH₂O | 3-pyrimidinyl |
| 909 | —C≡C—CH₂O | 4-pyrimidinyl |
| 910 | —C≡C—CH₂O | 2-pyrazinyl |
| 911 | —C≡C—CH₂O | 3-pyridazinyl |
| 912 | —C≡C—CH₂O | 4-pyridazinyl |
| 913 | —C≡C—CH₂O | 2-(2H-1,3-oxazinyl) |
| 914 | —C≡C—CH₂O | 2-(6H-1,3-oxazinyl) |
| 915 | —C≡C—CH₂O | 4-(6H-1,3-oxazinyl) |
| 916 | —C≡C—CH₂O | 6-(6H-1,3-oxazinyl) |
| 917 | —C≡C—CH₂O | [1,3,5]-2-triazinyl |
| 918 | —C≡C—CH₂O | [1,2,4]-3-triazinyl |
| 919 | —C≡C—CH₂O | [1,2,4]-5-triazinyl |
| 920 | —C≡C—CH₂O | [1,2,4]-6-triazinyl |

The Tables 1–144 below are based on the 4-benzoylpyrazoles of the formula Ib.

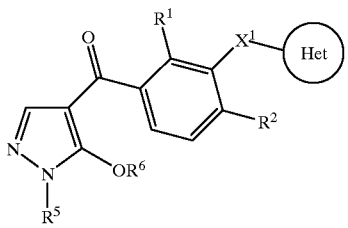

Ib

Table 1: Compounds 1.1–1.920
Compounds of the formula Ib where $R^1$ is chlorine and $R^2$ is chlorine, $R^5$ is methyl and $R^6$ is hydrogen and where for each individual compound the substituents $X^1$ and Het correspond to one line of Table A.

Table 2: Compounds 2.1–2.920
Compounds of the formula Ib where $R^1$ is chlorine and $R^2$ is chlorine, $R^5$ is ethyl and $R^6$ is hydrogen and where for each individual compound the substituents $X^1$ and Het correspond to one line of Table A.

Table 3: Compounds 3.1–3.920
Compounds of the formula Ib where $R^1$ is chlorine and $R^2$ is chlorine, $R^5$ is n-propyl and $R^6$ is hydrogen and where for each individual compound the substituents $X^1$ and Het correspond to one line of Table A.

Table 4: Compounds 4.1–4.920
Compounds of the formula Ib where $R^1$ is chlorine and $R^2$ is chlorine, $R^5$ is methyl and $R^6$ is methyl and where for each individual compound the substituents $X^1$ and Het correspond to one line of Table A.

Table 5: Compounds 5.1–5.920
Compounds of the formula Ib where $R^1$ is chlorine and $R^2$ is chlorine, $R^5$ is ethyl and $R^6$ is methyl and where for each individual compound the substituents $X^1$ and Het correspond to one line of Table A.

Table 6: Compounds 6.1–6.920
Compounds of the formula Ib where $R^1$ is chlorine and $R^2$ is chlorine, $R^5$ is n-propyl and $R^6$ is methyl and where for each individual compound the substituents $X^1$ and Het correspond to one line of Table A.

Table 7: Compounds 7.1–7.920
Compounds of the formula Ib where $R^1$ is chlorine and $R^2$ is chlorine, $R^5$ is methyl and $R^6$ is ethyl and where for each individual compound the substituents $X^1$ and Het correspond to one line of Table A.

Table 8: Compounds 8.1–8.920
Compounds of the formula Ib where $R^1$ is chlorine and $R^2$ is chlorine, $R^5$ is ethyl and $R^6$ is ethyl and where for each individual compound the substituents $X^1$ and Het correspond to one line of Table A.

Table 9: Compounds 9.1–9.920
Compounds of the formula Ib where $R^1$ is chlorine and $R^2$ is chlorine, $R^5$ is n-propyl and $R^6$ is ethyl and where for each individual compound the substituents $X^1$ and Het correspond to one line of Table A.

Table 10: Compounds 10.1–10.920
Compounds of the formula Ib where $R^1$ is chlorine and $R^2$ is chlorine, $R^5$ is methyl and $R^6$ is methylcarbonyl and where for each individual compound the substituents $X^1$ and Het correspond to one line of Table A.

Table 11: Compounds 11.1–11.920
Compounds of the formula Ib where $R^1$ is chlorine and $R^2$ is chlorine, $R^5$ is ethyl and $R^6$ is methylcarbonyl and where for each individual compound the substituents $X^1$ and Het correspond to one line of Table A.

Table 12: Compounds 12.1–12.920
Compounds of the formula Ib where $R^1$ is chlorine and $R^2$ is chlorine, $R^5$ is n-propyl and $R^6$ is methylcarbonyl and where for each individual compound the substituents $X^1$ and Het correspond to one line of Table A.

Table 13: Compounds 13.1–13.920
Compounds of the formula Ib where $R^1$ is chlorine and $R^2$ is chlorine, $R^5$ is methyl and $R^6$ is ethylcarbonyl and where for each individual compound the substituents $X^1$ and Het correspond to one line of Table A.

Table 14: Compounds 14.1–14.920
Compounds of the formula Ib where $R^1$ is chlorine and $R^2$ is chlorine, $R^5$ is ethyl and $R^6$ is ethylcarbonyl and where for each individual compound the substituents $X^1$ and Het correspond to one line of Table A.

Table 15: Compounds 15.1–15.920
Compounds of the formula Ib where $R^1$ is chlorine and $R^2$ is chlorine, $R^5$ is n-propyl and $R^6$ is ethylcarbonyl and where for each individual compound the substituents $X^1$ and Het correspond to one line of Table A.

Table 16: Compounds 16.1–16.920
Compounds of the formula Ib where $R^1$ is chlorine and $R^2$ is chlorine, $R^5$ is methyl and $R^6$ is methylsulfonyl and where for each individual compound the substituents $X^1$ and Het correspond to one line of Table A.

Table 17: Compounds 17.1–17.920
Compounds of the formula Ib where $R^1$ is chlorine and $R^2$ is chlorine, $R^5$ is ethyl and $R^6$ is methylsulfonyl and where for each individual compound the substituents $X^1$ and Het correspond to one line of Table A.

Table 18: Compounds 18.1–18.920
Compounds of the formula Ib where $R^1$ is chlorine and $R^2$ is chlorine, $R^5$ is n-propyl and $R^6$ is methylsulfonyl and where for each individual compound the substituents $X^1$ and Het correspond to one line of Table A.

Table 19: Compounds 19.1–19.920
Compounds of the formula Ib where $R^1$ is chlorine and $R^2$ is chlorine, $R^5$ is methyl and $R^6$ is ethylsulfonyl and where for each individual compound the substituents $X^1$ and Het correspond to one line of Table A.

Table 20: Compounds 20.1–20.920
Compounds of the formula Ib where $R^1$ is chlorine and $R^2$ is chlorine, $R^5$ is ethyl and $R^6$ is ethylsulfonyl and where for each individual compound the substituents $X^1$ and Het correspond to one line of Table A.

Table 21: Compounds 21.1–21.920
Compounds of the formula Ib where $R^1$ is chlorine and $R^2$ is chlorine, $R^5$ is n-propyl and $R^6$ is ethylsulfonyl and where for each individual compound the substituents $X^1$ and Het correspond to one line of Table A.

Table 22: Compounds 22.1–22.920
Compounds of the formula Ib where $R^1$ is chlorine and $R^2$ is chlorine, $R^5$ is methyl and $R^6$ is 4-methylphenylsulfonyl and where for each individual compound the substituents $X^1$ and Het correspond to one line of Table A.

Table 23: Compounds 23.1–23.920
Compounds of the formula Ib where $R^1$ is chlorine and $R^2$ is chlorine, $R^5$ is ethyl and $R^6$ is 4-methylphenylsulfonyl and where for each individual compound the substituents $X^1$ and Het correspond to one line of Table A.

Table 24: Compounds 24.1–24.920
Compounds of the formula Ib where $R^1$ is chlorine and $R^2$ is chlorine, $R^5$ is n-propyl and $R^6$ is 4-methylphenylsulfonyl and where for each individual compound the substituents $X^1$ and Het correspond to one line of Table A.

Table 25: Compounds 25.1–25.920
Compounds of the formula Ib where $R^1$ is chlorine and $R^2$ is methylsulfonyl, $R^5$ is methyl and $R^6$ is hydrogen and where for each individual compound the substituents $X^1$ and Het correspond to one line of Table A.

Table 26: Compounds 26.1–26.920
Compounds of the formula Ib where $R^1$ is chlorine and $R^2$ is methylsulfonyl, $R^5$ is ethyl and $R^6$ is hydrogen and where for each individual compound the substituents $X^1$ and Het correspond to one line of Table A.

Table 27: Compounds 27.1–27.920
Compounds of the formula Ib where $R^1$ is chlorine and $R^2$ is methylsulfonyl, $R^5$ is n-propyl and $R^6$ is hydrogen and where for each individual compound the substituents $X^1$ and Het correspond to one line of Table A.

Table 28: Compounds 28.1–28.920
Compounds of the formula Ib where $R^1$ is chlorine and $R^2$ is methylsulfonyl, $R^5$ is methyl and $R^6$ is methyl and where for each individual compound the substituents $X^1$ and Het correspond to one line of Table A.

Table 29: Compounds 29.1–29.920
Compounds of the formula Ib where $R^1$ is chlorine and $R^2$ is methylsulfonyl, $R^5$ is ethyl and $R^6$ is methyl and where for each individual compound the substituents $X^1$ and Het correspond to one line of Table A.

Table 30: Compounds 30.1–30.920
Compounds of the formula Ib where $R^1$ is chlorine and $R^2$ is methylsulfonyl, $R^5$ is n-propyl and $R^6$ is methyl and where for each individual compound the substituents $X^1$ and Het correspond to one line of Table A.

Table 31: Compounds 31.1–31.920
Compounds of the formula Ib where $R^1$ is chlorine and $R^2$ is methylsulfonyl, $R^5$ is methyl and $R^6$ is ethyl and where for each individual compound the substituents $X^1$ and Het correspond to one line of Table A.

Table 32: Compounds 32.1–32.920
Compounds of the formula Ib where $R^1$ is chlorine and $R^2$ is methylsulfonyl, $R^5$ is ethyl and $R^6$ is ethyl and where for each individual compound the substituents $X^1$ and Het correspond to one line of Table A.

Table 33: Compounds 33.1–33.920
Compounds of the formula Ib where $R^1$ is chlorine and $R^2$ is methylsulfonyl, $R^5$ is n-propyl and $R^6$ is ethyl and where for each individual compound the substituents $X^1$ and Het correspond to one line of Table A.

Table 34: Compounds 34.1–34.920
Compounds of the formula Ib where $R^1$ is chlorine and $R^2$ is methylsulfonyl, $R^5$ is methyl and $R^6$ is methylcarbonyl and where for each individual compound the substituents $X^1$ and Het correspond to one line of Table A.

Table 35: Compounds 35.1–35.920
Compounds of the formula Ib where $R^1$ is chlorine and $R^2$ is methylsulfonyl, $R^5$ is ethyl and $R^6$ is methylcarbonyl and where for each individual compound the substituents $X^1$ and Het correspond to one line of Table A.

Table 36: Compounds 36.1–36.920
Compounds of the formula Ib where $R^1$ is chlorine and $R^2$ is methylsulfonyl, $R^5$ is n-propyl and $R^6$ is methylcarbonyl and where for each individual compound the substituents $X^1$ and Het correspond to one line of Table A.

Table 37: Compounds 37.1–37.920
Compounds of the formula Ib where $R^1$ is chlorine and $R^2$ is methylsulfonyl, $R^5$ is methyl and $R^6$ is ethylcarbonyl and where for each individual compound the substituents $X^1$ and Het correspond to one line of Table A.

Table 38: Compounds 38.1–38.920
Compounds of the formula Ib where $R^1$ is chlorine and $R^2$ is methylsulfonyl, $R^5$ is ethyl and $R^6$ is ethylcarbonyl and where for each individual compound the substituents $X^1$ and Het correspond to one line of Table A.

Table 39: Compounds 39.1–39.920
Compounds of the formula Ib where $R^1$ is chlorine and $R^2$ is methylsulfonyl, $R^5$ is n-propyl and $R^6$ is ethylcarbonyl and where for each individual compound the substituents $X^1$ and Het correspond to one line of Table A.

Table 40: Compounds 40.1–40.920
Compounds of the formula Ib where $R^1$ is chlorine and $R^2$ is methylsulfonyl, $R^5$ is methyl and $R^6$ is methylsulfonyl and where for each individual compound the substituents $X^1$ and Het correspond to one line of Table A.

Table 41: Compounds 41.1–41.920
Compounds of the formula Ib where $R^1$ is chlorine and $R^2$ is methylsulfonyl, $R^5$ is ethyl and $R^6$ is methylsulfonyl and where for each individual compound the substituents $X^1$ and Het correspond to one line of Table A.

Table 42: Compounds 42.1–42.920
Compounds of the formula Ib where $R^1$ is chlorine and $R^2$ is methylsulfonyl, $R^5$ is n-propyl and $R^6$ is methylsulfonyl and where for each individual compound the substituents $X^1$ and Het correspond to one line of Table A.

Table 43: Compounds 43.1–43.920
Compounds of the formula Ib where $R^1$ is chlorine and $R^2$ is methylsulfonyl, $R^5$ is methyl and $R^6$ is ethylsulfonyl and where for each individual compound the substituents $X^1$ and Het correspond to one line of Table A.

Table 44: Compounds 44.1–44.920
Compounds of the formula Ib where $R^1$ is chlorine and $R^2$ is methylsulfonyl, $R^5$ is ethyl and $R^6$ is ethylsulfonyl and where for each individual compound the substituents $X^1$ and Het correspond to one line of Table A.

Table 45: Compounds 45.1–45.920
Compounds of the formula Ib where $R^1$ is chlorine and $R^2$ is methylsulfonyl, $R^5$ is n-propyl and $R^6$ is ethylsulfonyl and where for each individual compound the substituents $X^1$ and Het correspond to one line of Table A.

Table 46: Compounds 46.1–46.920
Compounds of the formula Ib where $R^1$ is chlorine and $R^2$ is methylsulfonyl, $R^5$ is methyl and $R^6$ is 4-methylphenylsulfonyl and where for each individual compound the substituents $X^1$ and Het correspond to one line of Table A.

Table 47: Compounds 47.1–47.920
Compounds of the formula Ib where $R^1$ is chlorine and $R^2$ is methylsulfonyl, $R^5$ is ethyl and $R^6$ is 4-methylphenylsulfonyl and where for each individual compound the substituents $X^1$ and Het correspond to one line of Table A.

Table 48: Compounds 48.1–48.920
Compounds of the formula Ib where $R^1$ is chlorine and $R^2$ is methylsulfonyl, $R^5$ is n-propyl and $R^6$ is 4-methylphenylsulfonyl and where for each individual compound the substituents $X^1$ and Het correspond to one line of Table A.

Table 49: Compounds 49.1–49.920
Compounds of the formula Ib where $R^1$ is chlorine and $R^2$ is trifluoromethyl, $R^5$ is methyl and $R^6$ is hydrogen and where for each individual compound the substituents $X^1$ and Het correspond to one line of Table A.

Table 50: Compounds 50.1–50.920
Compounds of the formula Ib where $R^1$ is chlorine and $R^2$ is trifluoromethyl, $R^5$ is ethyl and $R^6$ is hydrogen and where for each individual compound the substituents $X^1$ and Het correspond to one line of Table A.

Table 51: Compounds 51.1–51.920
Compounds of the formula Ib where $R^1$ is chlorine and $R^2$ is trifluoromethyl, $R^5$ is n-propyl and $R^6$ is hydrogen and where for each individual compound the substituents $X^1$ and Het correspond to one line of Table A.

Table 52: Compounds 52.1–52.920
Compounds of the formula Ib where $R^1$ is chlorine and $R^2$ is trifluoromethyl, $R^5$ is methyl and $R^6$ is methyl and where for each individual compound the substituents $X^1$ and Het correspond to one line of Table A.

Table 53: Compounds 53.1–53.920
Compounds of the formula Ib where $R^1$ is chlorine and $R^2$ is trifluoromethyl, $R^5$ is ethyl and $R^6$ is methyl and where for each individual compound the substituents $X^1$ and Het correspond to one line of Table A.

Table 54: Compounds 54.1–54.920
Compounds of the formula Ib where $R^1$ is chlorine and $R^2$ is trifluoromethyl, $R^5$ is n-propyl and $R^6$ is methyl and where for each individual compound the substituents $X^1$ and Het correspond to one line of Table A.

Table 55: Compounds 55.1–55.920
Compounds of the formula Ib where $R^1$ is chlorine and $R^2$ is trifluoromethyl, $R^5$ is methyl and $R^6$ is ethyl and where for each individual compound the substituents $X^1$ and Het correspond to one line of Table A.

Table 56: Compounds 56.1–56.920
Compounds of the formula Ib where $R^1$ is chlorine and $R^2$ is trifluoromethyl, $R^5$ is ethyl and $R^6$ is ethyl and where for each individual compound the substituents $X^1$ and Het correspond to one line of Table A.

Table 57: Compounds 57.1–57.920
Compounds of the formula Ib where $R^1$ is chlorine and $R^2$ is trifluoromethyl, $R^5$ is n-propyl and $R^6$ is ethyl and where for each individual compound the substituents $X^1$ and Het correspond to one line of Table A.

Table 58: Compounds 58.1–58.920
Compounds of the formula Ib where $R^1$ is chlorine and $R^2$ is trifluoromethyl, $R^5$ is methyl and $R^6$ is methylcarbonyl and where for each individual compound the substituents $X^1$ and Het correspond to one line of Table A.

Table 59: Compounds 59.1–59.920
Compounds of the formula Ib where $R^1$ is chlorine and $R^2$ is trifluoromethyl, $R^5$ is ethyl and $R^6$ is methylcarbonyl and where for each individual compound the substituents $X^1$ and Het correspond to one line of Table A.

Table 60: Compounds 60.1–60.920
Compounds of the formula Ib where $R^1$ is chlorine and $R^2$ is trifluoromethyl, $R^5$ is n-propyl and $R^6$ is methylcarbonyl and where for each individual compound the substituents $X^1$ and Het correspond to one line of Table A.

Table 61: Compounds 61.1–61.920
Compounds of the formula Ib where $R^1$ is chlorine and $R^2$ is trifluoromethyl, $R^5$ is methyl and $R^6$ is ethylcarbonyl and where for each individual compound the substituents $X^1$ and Het correspond to one line of Table A.

Table 62: Compounds 62.1–62.920
Compounds of the formula Ib where $R^1$ is chlorine and $R^2$ is trifluoromethyl, $R^5$ is ethyl and $R^6$ is ethylcarbonyl and where for each individual compound the substituents $X^1$ and Het correspond to one line of Table A.

Table 63: Compounds 63.1–63.920
Compounds of the formula Ib where $R^1$ is chlorine and $R^2$ is trifluoromethyl, $R^5$ is n-propyl and $R^6$ is ethylcarbonyl and where for each individual compound the substituents $X^1$ and Het correspond to one line of Table A.

Table 64: Compounds 64.1–64.920
Compounds of the formula Ib where $R^1$ is chlorine and $R^2$ is trifluoromethyl, $R^5$ is methyl and $R^6$ is methylsulfonyl and where for each individual compound the substituents $X^1$ and Het correspond to one line of Table A.

Table 65: Compounds 65.1–65.920
Compounds of the formula Ib where $R^1$ is chlorine and $R^2$ is trifluoromethyl, $R^5$ is ethyl and $R^6$ is methylsulfonyl and where for each individual compound the substituents $X^1$ and Het correspond to one line of Table A.

Table 66: Compounds 66.1–66.920
Compounds of the formula Ib where $R^1$ is chlorine and $R^2$ is trifluoromethyl, $R^5$ is n-propyl and $R^6$ is methylsulfonyl and where for each individual compound the substituents $X^1$ and Het correspond to one line of Table A.

Table 67: Compounds 67.1–67.920
Compounds of the formula Ib where $R^1$ is chlorine and $R^2$ is trifluoromethyl, $R^5$ is methyl and $R^6$ is ethylsulfonyl and where for each individual compound the substituents $X^1$ and Het correspond to one line of Table A.

Table 68: Compounds 68.1–68.920
Compounds of the formula Ib where $R^1$ is chlorine and $R^2$ is trifluoromethyl, $R^5$ is ethyl and $R^6$ is ethylsulfonyl and where for each individual compound the substituents $X^1$ and Het correspond to one line of Table A.

Table 69: Compounds 69.1–69.920
Compounds of the formula Ib where $R^1$ is chlorine and $R^2$ is trifluoromethyl, $R^5$ is n-propyl and $R^6$ is ethylsulfonyl and where for each individual compound the substituents $X^1$ and Het correspond to one line of Table A.

Table 70: Compounds 70.1–70.920
Compounds of the formula Ib where $R^1$ is chlorine and $R^2$ is trifluoromethyl, $R^5$ is methyl and $R^6$ is 4-methylphenylsulfonyl and where for each individual compound the substituents $X^1$ and Het correspond to one line of Table A.

Table 71: Compounds 71.1–71.920
Compounds of the formula Ib where $R^1$ is chlorine and $R^2$ is trifluoromethyl, $R^5$ is ethyl and $R^6$ is 4-methylphenylsulfonyl and where for each individual compound the substituents $X^1$ and Het correspond to one line of Table A.

Table 72: Compounds 72.1–72.920
Compounds of the formula Ib where $R^1$ is chlorine and $R^2$ is trifluoromethyl, $R^5$ is n-propyl and $R^6$ is 4-methylphenylsulfonyl and where for each individual compound the substituents $X^1$ and Het correspond to one line of Table A.

Table 73: Compounds 73.1–73.920
Compounds of the formula Ib where $R^1$ is methyl and $R^2$ is chlorine, $R^5$ is methyl and $R^6$ is hydrogen and where for each individual compound the substituents $X^1$ and Het correspond to one line of Table A.

Table 74: Compounds 74.1–74.920
Compounds of the formula Ib where $R^1$ is methyl and $R^2$ is chlorine, $R^5$ is ethyl and $R^6$ is hydrogen and where for each individual compound the substituents $X^1$ and Het correspond to one line of Table A.

Table 75: Compounds 75.1–75.920
Compounds of the formula Ib where $R^1$ is methyl and $R^2$ is chlorine, $R^5$ is n-propyl and $R^6$ is hydrogen and where for each individual compound the substituents $X^1$ and Het correspond to one line of Table A.

Table 76: Compounds 76.1–76.920
Compounds of the formula Ib where $R^1$ is methyl and $R^2$ is chlorine, $R^5$ is methyl and $R^6$ is methyl and where for each individual compound the substituents $X^1$ and Het correspond to one line of Table A.

Table 77: Compounds 77.1–77.920
Compounds of the formula Ib where $R^1$ is methyl and $R^2$ is chlorine, $R^5$ is ethyl and $R^6$ is methyl and where for each individual compound the substituents $X^1$ and Het correspond to one line of Table A.

Table 78: Compounds 78.1–78.920
Compounds of the formula Ib where $R^1$ is methyl and $R^2$ is chlorine, $R^5$ is n-propyl and $R^6$ is methyl and where for each individual compound the substituents $X^1$ and Het correspond to one line of Table A.

Table 79: Compounds 79.1–79.920
Compounds of the formula Ib where $R^1$ is methyl and $R^2$ is chlorine, $R^5$ is methyl and $R^6$ is ethyl and where for each individual compound the substituents $X^1$ and Het correspond to one line of Table A.

Table 80: Compounds 80.1–80.920
Compounds of the formula Ib where $R^1$ is methyl and $R^2$ is chlorine, $R^5$ is methyl and $R^6$ is ethyl and where for each individual compound the substituents $X^1$ and Het correspond to one line of Table A.

Table 81: Compounds 81.1–81.920
Compounds of the formula Ib where $R^1$ is methyl and $R^2$ is chlorine, $R^5$ is n-propyl and $R^6$ is ethyl and where for each individual compound the substituents $X^1$ and Het correspond to one line of Table A.

Table 82: Compounds 82.1–82.920
Compounds of the formula Ib where $R^1$ is methyl and $R^2$ is chlorine, $R^5$ is methyl and $R^6$ is methylcarbonyl and where for each individual compound the substituents $X^1$ and Het correspond to one line of Table A.

Table 83: Compounds 83.1–83.920
Compounds of the formula Ib where $R^1$ is methyl and $R^2$ is chlorine, $R^5$ is ethyl and $R^6$ is methylcarbonyl and where for each individual compound the substituents $X^1$ and Het correspond to one line of Table A.

Table 84: Compounds 84.1–84.920
Compounds of the formula Ib where $R^1$ is methyl and $R^2$ is chlorine, $R^5$ is n-propyl and $R^6$ is methylcarbonyl and where for each individual compound the substituents $X^1$ and Het correspond to one line of Table A.

Table 85: Compounds 85.1–85.920
Compounds of the formula Ib where $R^1$ is methyl and $R^2$ is chlorine, $R^5$ is methyl and $R^6$ is ethylcarbonyl and where for each individual compound the substituents $X^1$ and Het correspond to one line of Table A.

Table 86: Compounds 86.1–86.920
Compounds of the formula Ib where $R^1$ is methyl and $R^2$ is chlorine, $R^5$ is ethyl and $R^6$ is ethylcarbonyl and where for each individual compound the substituents $X^1$ and Het correspond to one line of Table A.

Table 87: Compounds 87.1–87.920
Compounds of the formula Ib where $R^1$ is methyl and $R^2$ is chlorine, $R^5$ is n-propyl and $R^6$ is ethylcarbonyl and where for each individual compound the substituents $X^1$ and Het correspond to one line of Table A.

Table 88: Compounds 88.1–88.920
Compounds of the formula Ib where $R^1$ is methyl and $R^2$ is chlorine, $R^5$ is methyl and $R^6$ is methylsulfonyl and where for each individual compound the substituents $X^1$ and Het correspond to one line of Table A.

Table 89: Compounds 89.1–89.920
Compounds of the formula Ib where $R^1$ is methyl and $R^2$ is chlorine, $R^5$ is ethyl and $R^6$ is methylsulfonyl and where for each individual compound the substituents $X^1$ and Het correspond to one line of Table A.

Table 90: Compounds 90.1–90.920
Compounds of the formula Ib where $R^1$ is methyl and $R^2$ is chlorine, $R^5$ is n-propyl and $R^6$ is methylsulfonyl and where for each individual compound the substituents $X^1$ and Het correspond to one line of Table A.

Table 91: Compounds 91.1–91.920
Compounds of the formula Ib where $R^1$ is methyl and $R^2$ is chlorine, $R^5$ is methyl and $R^6$ is ethylsulfonyl and where for each individual compound the substituents $X^1$ and Het correspond to one line of Table A.

Table 92: Compounds 92.1–92.920
Compounds of the formula Ib where $R^1$ is methyl and $R^2$ is chlorine, $R^5$ is ethyl and $R^6$ is ethylsulfonyl and where for each individual compound the substituents $X^1$ and Het correspond to one line of Table A.

Table 93: Compounds 93.1–93.920
Compounds of the formula Ib where $R^1$ is methyl and $R^2$ is chlorine, $R^5$ is n-propyl and $R^6$ is ethylsulfonyl and where for each individual compound the substituents $X^1$ and Het correspond to one line of Table A.

Table 94: Compounds 94.1–94.920
Compounds of the formula Ib where $R^1$ is methyl and $R^2$ is chlorine, $R^5$ is methyl and $R^6$ is 4-methylphenylsulfonyl and where for each individual compound the substituents $X^1$ and Het correspond to one line of Table A.

Table 95: Compounds 95.1–95.920
Compounds of the formula Ib where $R^1$ is methyl and $R^2$ is chlorine, $R^5$ is ethyl and $R^5$ is 4-methylphenylsulfonyl and where for each individual compound the substituents $X^1$ and Het correspond to one line of Table A.

Table 96: Compounds 96.1–96.920
Compounds of the formula Ib where $R^1$ is methyl and $R^2$ is chlorine, $R^5$ is n-propyl and $R^6$ is 4-methylphenylsulfonyl and where for each individual compound the substituents $X^1$ and Het correspond to one line of Table A.

Table 97: Compounds 97.1–97.920
Compounds of the formula Ib where $R^1$ is methyl and $R^2$ is methylsulfonyl, $R^5$ is methyl and $R^6$ is hydrogen and where for each individual compound the substituents $X^1$ and Het correspond to one line of Table A.

Table 98: Compounds 98.1–98.920
Compounds of the formula Ib where $R^1$ is methyl and $R^2$ is methylsulfonyl, $R^5$ is ethyl and $R^6$ is hydrogen and where for each individual compound the substituents $X^1$ and Het correspond to one line of Table A.

Table 99: Compounds 99.1–99.920
Compounds of the formula Ib where $R^1$ is methyl and $R^2$ is methylsulfonyl, $R^5$ is n-propyl and $R^6$ is hydrogen and where for each individual compound the substituents $X^1$ and Het correspond to one line of Table A.

Table 100: Compounds 100.1–100.920
Compounds of the formula Ib where $R^1$ is methyl and $R^2$ is methylsulfonyl, $R^5$ is methyl and $R^6$ is methyl and where for each individual compound the substituents $X^1$ and Het correspond to one line of Table A.

Table 101: Compounds 101.1–101.920
Compounds of the formula Ib where $R^1$ is methyl and $R^2$ is methylsulfonyl, $R^5$ is ethyl and $R^6$ is methyl and where for each individual compound the substituents $X^1$ and Het correspond to one line of Table A.

Table 102: Compounds 102.1–102.920
Compounds of the formula Ib where $R^1$ is methyl and $R^2$ is methylsulfonyl, $R^5$ is n-propyl and $R^6$ is methyl and where for each individual compound the substituents $X^1$ and Het correspond to one line of Table A.

Table 103: Compounds 103.1–103.920
Compounds of the formula Ib where $R^1$ is methyl and $R^2$ is methylsulfonyl, $R^5$ is methyl and $R^6$ is ethyl and where for each individual compound the substituents $X^1$ and Het correspond to one line of Table A.

Table 104: Compounds 104.1–104.920
Compounds of the formula Ib where $R^1$ is methyl and $R^2$ is methylsulfonyl, $R^5$ is ethyl and $R^6$ is ethyl and where for each individual compound the substituents $X^1$ and Het correspond to one line of Table A.

Table 105: Compounds 105.1–105.920
Compounds of the formula Ib where $R^1$ is methyl and $R^2$ is methylsulfonyl, $R^5$ is n-propyl and $R^6$ is ethyl and where for each individual compound the substituents $X^1$ and Het correspond to one line of Table A.

Table 106: Compounds 106.1–106.920
Compounds of the formula Ib where $R^1$ is methyl and $R^2$ is methylsulfonyl, $R^5$ is methyl and $R^6$ is methylcarbonyl and where for each individual compound the substituents $X^1$ and Het correspond to one line of Table A.

Table 107: Compounds 107.1–107.920
Compounds of the formula Ib where $R^1$ is methyl and $R^2$ is methylsulfonyl, $R^5$ is ethyl and $R^6$ is methylcarbonyl and where for each individual compound the substituents $X^1$ and Het correspond to one line of Table A.

Table 108: Compounds 108.1–108.920
Compounds of the formula Ib where $R^1$ is methyl and $R^2$ is methylsulfonyl, $R^5$ is n-propyl and $R^6$ is methylcarbonyl and where for each individual compound the substituents $X^1$ and Het correspond to one line of Table A.

Table 109: Compounds 109.1–109.920
Compounds of the formula Ib where $R^1$ is methyl and $R^2$ is methylsulfonyl, $R^5$ is methyl and $R^6$ is ethylcarbonyl and where for each individual compound the substituents $X^1$ and Het correspond to one line of Table A.

Table 110: Compounds 110.1–110.920
Compounds of the formula Ib where $R^1$ is methyl and $R^2$ is methylsulfonyl, $R^5$ is ethyl and $R^6$ is ethylcarbonyl and where for each individual compound the substituents $X^1$ and Het correspond to one line of Table A.

Table 111: Compounds 111.1–111.920
Compounds of the formula Ib where $R^1$ is methyl and $R^2$ is methylsulfonyl, $R^5$ is n-propyl and $R^6$ is ethylcarbonyl and where for each individual compound the substituents $X^1$ and Het correspond to one line of Table A.

Table 112: Compounds 112.1–112.920
Compounds of the formula Ib where $R^1$ is methyl and $R^2$ is methylsulfonyl, $R^5$ is methyl and $R^6$ is methylsulfonyl and where for each individual compound the substituents $X^1$ and Het correspond to one line of Table A.

Table 113: Compounds 113.1–113.920
Compounds of the formula Ib where $R^1$ is methyl and $R^2$ is methylsulfonyl, $R^5$ is ethyl and $R^6$ is methylsulfonyl and where for each individual compound the substituents $X^1$ and Het correspond to one line of Table A.

Table 114: Compounds 114.1–114.920
Compounds of the formula Ib where $R^1$ is methyl and $R^2$ is methylsulfonyl, $R^5$ is n-propyl and $R^6$ is methylsulfonyl and where for each individual compound the substituents $X^1$ and Het correspond to one line of Table A.

Table 115: Compounds 115.1–115.920
Compounds of the formula Ib where $R^1$ is methyl and $R^2$ is methylsulfonyl, $R^5$ is methyl and $R^6$ is ethylsulfonyl and where for each individual compound the substituents $X^1$ and Het correspond to one line of Table A.

Table 116: Compounds 116.1–116.920
Compounds of the formula Ib where $R^1$ is methyl and $R^2$ is methylsulfonyl, $R^5$ is ethyl and $R^6$ is ethylsulfonyl and where for each individual compound the substituents $X^1$ and Het correspond to one line of Table A.

Table 117: Compounds 117.1–117.920
Compounds of the formula Ib where $R^1$ is methyl and $R^2$ is methylsulfonyl, $R^5$ is n-propyl and $R^6$ is ethylsulfonyl and where for each individual compound the substituents $X^1$ and Het correspond to one line of Table A.

Table 118: Compounds 118.1–118.920
Compounds of the formula Ib where $R^1$ is methyl and $R^2$ is methylsulfonyl, $R^5$ is methyl and $R^6$ is 4-methylphenylsulfonyl and where for each individual compound the substituents $X^1$ and Het correspond to one line of Table A.

Table 119: Compounds 119.1–119.920
Compounds of the formula Ib where $R^1$ is methyl and $R^2$ is methylsulfonyl, $R^5$ is ethyl and $R^6$ is 4-methylphenylsulfonyl and where for each individual compound the substituents $X^1$ and Het correspond to one line of Table A.

Table 120: Compounds 120.1–120.920
Compounds of the formula Ib where $R^1$ is methyl and $R^2$ is methylsulfonyl, $R^5$ is n-propyl and $R^6$ is 4-methylphenylsulfonyl and where for each individual compound the substituents $X^1$ and Het correspond to one line of Table A.

Table 121: Compounds 121.1–121.920
Compounds of the formula Ib where $R^1$ is methyl and $R^2$ is trifluoromethyl, $R^5$ is methyl and $R^5$ is hydrogen and where for each individual compound the substituents $X^1$ and Het correspond to one line of Table A.

Table 122: Compounds 122.1–122.920
Compounds of the formula Ib where $R^1$ is methyl and $R^2$ is trifluoromethyl, $R^5$ is ethyl and $R^6$ is hydrogen and where for each individual compound the substituents $X^1$ and Het correspond to one line of Table A.

Table 123: Compounds 123.1–123.920
Compounds of the formula Ib where $R^1$ is methyl and $R^2$ is trifluoromethyl, $R^5$ is n-propyl and $R^6$ is hydrogen and where for each individual compound the substituents $X^1$ and Het correspond to one line of Table A.

Table 124: Compounds 124.1–124.920
Compounds of the formula Ib where $R^1$ is methyl and $R^2$ is trifluoromethyl, $R^5$ is methyl and $R^6$ is methyl and where for each individual compound the substituents $X^1$ and Het correspond to one line of Table A.

Table 125: Compounds 125.1–125.920
Compounds of the formula Ib where $R^1$ is methyl and $R^2$ is trifluoromethyl, $R^5$ is ethyl and $R^6$ is methyl and where for each individual compound the substituents $X^1$ and Het correspond to one line of Table A.

Table 126: Compounds 126.1–126.920
Compounds of the formula Ib where $R^1$ is methyl and $R^2$ is trifluoromethyl, $R^5$ is n-propyl and $R^6$ is methyl and where for each individual compound the substituents $X^1$ and Het correspond to one line of Table A.

Table 127: Compounds 127.1–127.920
Compounds of the formula Ib where $R^1$ is methyl and $R^2$ is trifluoromethyl, $R^5$ is methyl and $R^6$ is ethyl and where for each individual compound the substituents $X^1$ and Het correspond to one line of Table A.

Table 128: Compounds 128.1–128.920

Compounds of the formula Ib where $R^1$ is methyl and $R^2$ is trifluoromethyl, $R^5$ is ethyl and $R^6$ is ethyl and where for each individual compound the substituents $X^1$ and Het correspond to one line of Table A.

Table 129: Compounds 129.1–129.920

Compounds of the formula Ib where $R^1$ is methyl and $R^2$ is trifluoromethyl, $R^5$ is n-propyl and $R^6$ is ethyl and where for each individual compound the substituents $X^1$ and Het correspond to one line of Table A.

Table 130: Compounds 130.1–130.920

Compounds of the formula Ib where $R^1$ is methyl and $R^2$ is trifluoromethyl, $R^5$ is methyl and $R^6$ is methylcarbonyl and where for each individual compound the substituents $X^1$ and Het correspond to one line of Table A.

Table 131: Compounds 131.1–131.920

Compounds of the formula Ib where $R^1$ is methyl and $R^2$ is trifluoromethyl, $R^5$ is ethyl and $R^6$ is methylcarbonyl and where for each individual compound the substituents $X^1$ and Het correspond to one line of Table A.

Table 132: Compounds 132.1–132.920

Compounds of the formula Ib where $R^1$ is methyl and $R^2$ is trifluoromethyl, $R^5$ is n-propyl and $R^6$ is methylcarbonyl and where for each individual compound the substituents $X^1$ and Het correspond to one line of Table A.

Table 133: Compounds 133.1–133.920

Compounds of the formula Ib where $R^1$ is methyl and $R^2$ is trifluoromethyl, $R^5$ is methyl and $R^6$ is ethylcarbonyl and where for each individual compound the substituents $X^1$ and Het correspond to one line of Table A.

Table 134: Compounds 134.1–134.920

Compounds of the formula Ib where $R^1$ is methyl and $R^2$ is trifluoromethyl, $R^5$ is ethyl and $R^6$ is ethylcarbonyl and where for each individual compound the substituents $X^1$ and Het correspond to one line of Table A.

Table 135: Compounds 135.1–135.920

Compounds of the formula Ib where $R^1$ is methyl and $R^2$ is trifluoromethyl, $R^5$ is n-propyl and $R^6$ is ethylcarbonyl and where for each individual compound the substituents $X^1$ and Het correspond to one line of Table A.

Table 136: Compounds 136.1–136.920

Compounds of the formula Ib where $R^1$ is methyl and $R^2$ is trifluoromethyl, $R^5$ is methyl and $R^6$ is methylsulfonyl and where for each individual compound the substituents $X^1$ and Het correspond to one line of Table A.

Table 137: Compounds 137.1–137.920

Compounds of the formula Ib where $R^1$ is methyl and $R^2$ is trifluoromethyl, $R^5$ is ethyl and $R^6$ is methylsulfonyl and where for each individual compound the substituents $X^1$ and Het correspond to one line of Table A.

Table 138: Compounds 138.1–138.920

Compounds of the formula Ib where $R^1$ is methyl and $R^2$ is trifluoromethyl, $R^5$ is n-propyl and $R^6$ is methylsulfonyl and where for each individual compound the substituents $X^1$ and Het correspond to one line of Table A.

Table 139: Compounds 139.1–139.920

Compounds of the formula Ib where $R^1$ is methyl and $R^2$ is trifluoromethyl, $R^5$ is methyl and $R^6$ is ethylsulfonyl and where for each individual compound the substituents $X^1$ and Het correspond to one line of Table A.

Table 140: Compounds 140.1–140.920

Compounds of the formula Ib where $R^1$ is methyl and $R^2$ is trifluoromethyl, $R^5$ is ethyl and $R^6$ is ethylsulfonyl and where for each individual compound the substituents $X^1$ and Het correspond to one line of Table A.

Table 141: Compounds 141.1–141.920

Compounds of the formula Ib where $R^1$ is methyl and $R^2$ is trifluoromethyl, $R^5$ is n-propyl and $R^6$ is ethylsulfonyl and where for each individual compound the substituents $X^1$ and Het correspond to one line of Table A.

Table 142: Compounds 142.1–142.920

Compounds of the formula Ib where $R^1$ is methyl and $R^2$ is trifluoromethyl, $R^5$ is methyl and $R^6$ is 4-methylphenylsulfonyl and where for each individual compound the substituents $X^1$ and Het correspond to one line of Table A.

Table 143: Compounds 143.1–143.920

Compounds of the formula Ib where $R^1$ is methyl and $R^2$ is trifluoromethyl, $R^5$ is ethyl and $R^6$ is 4-methylphenylsulfonyl and where for each individual compound the substituents $X^1$ and Het correspond to one line of Table A.

Table 144: Compounds 144.1–144.920

Compounds of the formula Ib where $R^1$ is methyl and $R^2$ is trifluoromethyl, $R^5$ is n-propyl and $R^6$ is 4-methylphenylsulfonyl and where for each individual compound the substituents $X^1$ and Het correspond to one line of Table A.

The compounds I and their agriculturally useful salts are suitable, both in the form of isomer mixtures and in the form of the pure isomers, as herbicides. The herbicidal compositions comprising I control vegetation on non-crop areas very efficiently, especially at high rates of application. They act against broad-leaved weeds and harmful grasses in crops such as wheat, rice, maize, soya and cotton without causing any significant damage to the crop plants. This effect is mainly observed at low rates of application.

Depending on the application method used, the compounds I, or the compositions comprising them, can additionally be employed in a further number of crop plants for eliminating undesirable plants. Examples of suitable crops are the following:

*Allium cepa, Ananas comosus, Arachis hypogaea, Asparagus officinalis, Beta vulgaris* spec. *altissima, Beta vulgaris* spec. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum,* Malus spec., *Manihot esculenta, Medicago sativa,* Musa spec., *Nicotiana tabacum*(*N. rustica*), *Olea europaea, Oryza sativa, Phaseolus lunatus, Phaseolus vulgaris, Picea abies,* Pinus spec., *Pisum sativum, Prunus avium, Prunus persica, Pyrus communis, Ribes sylvestre, Ricinus communis, Saccharum officinarum, Secale cereale, Solanum tuberosum, Sorghum bicolor* (*s. vulgare*), *Theobroma cacao, Trifolium pratense, Triticum aestivum, Triticum durum, Vicia faba, Vitis vinifera* and *Zea mays.*

In addition, the compounds I may also be used in crops which tolerate the action of herbicides owing to breeding, including genetic engineering methods.

The herbicidal compositions or the active compounds can be applied pre- or post-emergence. If the active compounds are less well tolerated by certain crop plants, application techniques may be used in which the herbicidal compositions are sprayed, with the aid of the spraying equipment, in such a way that they come into contact as little as possible, if at all, with the leaves of the sensitive crop plants, while the active compounds reach the leaves of undesirable plants growing underneath, or the bare soil surface (post-directed, lay-by).

The compounds I, or the herbicidal compositions comprising them, can be used for example in the form of ready-to-spray aqueous solutions, powders, suspensions, also highly-concentrated aqueous, oily or other suspensions or dispersions, emulsions, oil dispersions, pastes, dusts, materials for broadcasting, or granules, by means of spraying, atomizing, dusting, broadcasting or watering. The use forms depend on the intended aims; in any case, they should guarantee a very fine distribution of the active compounds according to the invention.

Essentially, suitable inert auxiliaries include: mineral oil fractions of medium to high boiling point, such as kerosene and animal origin, aliphatic, cyclic and aromatic hydrocarbons, eg. paraffin, tetrahydronaphthalene, alkylated naphthalenes and their derivatives, alkylated benzenes and their derivatives, alcohols such as methanol, ethanol, propanol, butanol and cyclohexanol, ketones such as cyclohexanone, or strongly polar solvents, eg. amines such as N-methylpyrrolidone, and water.

Aqueous use forms can be prepared from emulsion concentrates, suspensions, pastes, wettable powders or water-dispersible granules by adding water. To prepare emulsions, pastes or oil dispersions, substituted 4-benzoylpyrazoles, either as such or dissolved in an oil or solvent, can be homogenized in water by means of a wetting agent, tackifier, dispersant or emulsifier. Alternatively, it is possible to prepare concentrates comprising active compound, wetting agent, tackifier, dispersant or emulsifier and, if desired, solvent or oil, which are suitable for dilution with water.

Suitable surfactants are the alkali metal salts, alkaline earth metal salts and ammonium salts of aromatic sulfonic acids, eg. ligno-, phenol-, naphthalene- and dibutylnaphthalenesulfonic acid, and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene, or of the naphthalenesulfonic acids with phenol and formaldehyde, polyoxyethylene octylphenol ether, ethoxylated isooctyl-, octyl- or nonylphenol, alkylphenyl or tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methylcellulose.

Powders, materials for broadcasting and dusts can be prepared by mixing or grinding the active compounds together with a solid carrier.

Granules, eg. coated granules, impregnated granules and homogeneous granules, can be prepared by binding the active compounds to solid carriers. Solid carriers are mineral earths, such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate and ammonium nitrate, ureas, and products of vegetable origin, such as cereal meal, tree bark meal, wood meal and nutshell meal, cellulose powders, or other solid carriers.

The concentrations of the active compounds I in the ready-to-use preparations can be varied within wide ranges.

In general, the formulations comprise from 0.001 to 98% by weight, preferably 0.01 to 95% by weight of at least one active compound. The active compounds are employed in a purity of from 90% to 100%, preferably 95% to 100% (according to the NMR spectrum).

The compounds I according to the invention can be formulated for example as follows:

I. 20 parts by weight of the compound I are dissolved in a mixture composed of 80 parts by weight of alkylated benzene, 10 parts by weight of the adduct of 8 to mol of ethylene oxide to 1 mol of oleic acid N-monoethanolamide, 5 parts by weight of calcium dodecylbenzenesulfonate and 5 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

II. 20 parts by weight of the compound I are dissolved in a mixture composed of 40 parts by weight of cyclohexanone, 30 parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

III. 20 parts by weight of the active compound I are dissolved in a mixture composed of 25 parts by weight of cyclohexanone, 65 parts by weight of a mineral oil fraction of boiling point 210 to 280° C. and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

IV. 20 parts by weight of the active compound I are mixed thoroughly with 3 parts by weight of sodium diisobutylnaphthalenesulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active compound.

V. 3 parts by weight of the active compound I are mixed with 97 parts by weight of finely divided kaolin. This gives a dust which comprises 3% by weight of the active compound.

VI. 20 parts by weight of the active compound I are mixed intimately with 2 parts by weight of calcium dodecylbenzenesulfonate, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

VII. 1 part by weight of the compound I is dissolved in a mixture composed of 70 parts by weight of cyclohexanone, 20 parts by weight of ethoxylated isooctylphenol and 10 parts by weight of ethoxylated castor oil. This gives a stable emulsion concentrate.

VIII. 1 part by weight of the compound I is dissolved in a mixture composed of 80 parts by weight of cyclohexanone and 20 parts by weight of Wettol® EM 31 (nonionic emulsifier based on ethoxylated castor oil). This gives a stable emulsion concentrate.

To widen the activity spectrum and to achieve synergistic effects, the substituted 4-benzoylpyrazoles I may be mixed with a large number of representatives of other herbicidal or growth-regulating active compound groups and then applied concomitantly. Suitable components for mixtures are, for example, 1,2,4-thiadiazoles, 1,3,4-thiadiazoles, amides, aminophosphoric acid and its derivatives, aminotriazoles, anilides, (het)aryloxyalkanoic acids and their derivatives, benzoic acid and its derivatives, benzothiadiazinones, 2-aroyl-1,3-cyclohexanediones, hetaryl aryl ketones, benzylisoxazolidinones, meta-$CF_3$-phenyl derivatives, carbamates, quinolinecarboxylic acid and its derivatives, chloroacetanilides, cyclohexane-1,3-dione derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and hetaryloxyphenoxypropionic esters, phenylacetic acid and its derivatives, phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides and uracils.

It may furthermore be advantageous to apply the compounds I, alone or else concomitantly in combination with other herbicides, in the form of a mixture with other crop protection agents, for example together with agents for controlling pests or phytopathogenic fungi or bacteria. Also of interest is the miscibility with mineral salt solutions, which are employed for treating nutritional and trace element deficiencies. Non-phytotoxic oils and oil concentrates may also be added.

The active compound application rates are from 0.001 to 3.0, preferably 0.01 to 1.0 kg/ha of active substance (a.s.), depending on the control target, the season, the target plants and the growth stage.

The syntheses of some starting materials and products are described below.

2-Chloro-3-(N-3,5-dimethylpyrazolyloxymethyl) phenyl)-4-sulfonylmethyl-(N-methyl-2-hydroxypyrazole) methanone.

Step a: Methyl 2-chloro-3-bromomethyl-4-sulfonylmethylbenzoate 80 g (0.3 mol) of methyl 2-chloro-3-methyl-4-sulfonylmethylbenzoate in 1l of carbon tetrachloride are heated at 76° C. together with 54 g (0.31 mol) of N-bromosuccinimide and 1.5 g of azoisobutyronitrile for 6 h. The reaction mixture is filtered and freed from the solvent under reduced pressure. Yield: 104 g; m.p. 83–85° C.

Step b: Methyl 2-chloro-3-(N-3,5-dimethylpyrazolyloxymethyl)-4-sulfonylmethylbenzoate 3.3 g of 3,5-dimethylpyrazole and 4.2 g of potassium carbonate in 30 ml of N,N-dimethylformamide are heated at 70° C. for 1 h, admixed with a solution of 10 g (29.3 mmol) of methyl 2-chloro-3-bromomethyl-4-sulfonylmethylbenzoate in 100 ml of N,N-dimethylformamide, and the mixture is heated at 40° C. for 4 h. The reaction mixture is freed from the solvent under reduced pressure, taken up in ethyl acetate and washed with 5% strength aqueous sodium hydroxide solution. The organic phase is dried with sodium sulfate, filtered and freed from the solvent under reduced pressure. Yield: 10.2 g; m.p. 90–95° C.

Step c: 2-Chloro-3-(N-3,5-dimethylpyrazolyloxymethyl)-4-sulfonylmethylbenzoic acid 9.9 g (26.6 mmol) of methyl 2-chloro-3-(N-3,5-dimethylpyrazolyloxymethyl)-4-sulfonylmethylbenzoate in a mixture of 50 ml of tetrahydrofuran and 50 ml of dist. water are treated at room temperature with 1.3 g of lithium hydroxide for 12 h. The reaction mixture is introduced into 300 ml of dist. water, adjusted to pH 1 using 10% strength aqueous hydrochloric acid and extracted with ethyl acetate. The combined organic phases are dried with sodium sulfate, filtered and freed from the solvent under reduced pressure. Yield: 6.2 g; m.p. 201–207° C.

Step d: 2-Chloro-3-(N-3,5-dimethylpyrazolyloxymethyl) phenyl)-4-sulfonylmethyl-(N-methyl-2-hydroxypyrazole) methanone 2.0 g (5.6 mmol) of 2-chloro-3-(N-3,5-dimethylpyrazolyloxymethyl)-4-sulfonylmethylbenzoic acid, 0.6 g (5.6 mmol) of N-methyl-5-hydroxypyrazole and 1.4 g of N,N-dicyclohexylcarbodiimide in 50 ml of tetrahydrofuran are heated at 40° C. for 6 h. The reaction mixture is filtered and taken up in ethyl acetate. The organic phase is washed with saturated, aqueous sodium bicarbonate solution, dried with sodium sulfate, filtered and freed from the solvent under reduced pressure.

The crude product, together with 1.2 g of potassium carbonate, in 20 ml of 1,4-dioxane, is heated at 100° C. for 6 h. The reaction mixture is introduced into 500 ml of dist. water and extracted with diethyl ether. The organic phase is adjusted to pH 3 using 10% strength aqueous hydrochloric acid and extracted with dichloromethane. The organic phase is washed with dist. water, dried with sodium sulfate, filtered and freed from the solvent under reduced pressure. Yield: 1.5 g, m.p. 74° C.

TABLE 145

| No. | $R^5$ | $R^6$ | $X^1$ | Het | m.p. [° C.] | $^1$H NMR [ppm] |
|---|---|---|---|---|---|---|
| 145.1 | $CH_3$ | H | $CH_2O$ | 1-pyrazolyl | 160 | |
| 145.2 | $CH_3$ | iso-propyl | $CH_2O$ | 1-pyrazolyl | | 1.4 (d, 6 H); 3.4 (s, 3 H); 3.7 (s, 3 H); 5.3 (m, 1 H); 6.1 (s, 2 H); 6.2 (d, 1 H); 7.2 (s, 1 H); 7.3 (s, 1 H); 7.4 (d, 1 H); 7.6 (d, 1 H); 8.2 (d, 1 H) |
| 145.3 | $CH_3$ | H | $CH_2O$ | 3,5-di-methyl-1-pyrazolyl | 74 | |
| 145.4 | $CH_3$ | iso-propyl | $CH_2O$ | 3,5-di-methyl-1-pyrazolyl | 149 | |

TABLE 145-continued

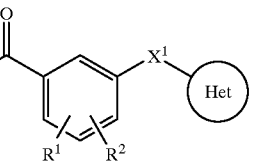

| No. | R⁵ | R⁶ | X¹ | Het | m.p. [° C.] | ¹H NMR [ppm] |
|---|---|---|---|---|---|---|
| 145.5 | CH₃ | SO₂CH₃ | CH₂O | 3,5-di-methyl-1-pyrazolyl | 157 | |
| 145.6 | CH₃ | H | CH₂O | 4-chloro-1-pyrazolyl | 164 | |
| 145.7 | CH₃ | iso-propyl | CH₂O | 4-chloro-1-pyrazolyl | | 1.4 (d, 6 H); 3.4 (s, 3 H); 3.7 (s, 3 H); 5.3 (m, 1 H); 6.1 (s, 2 H); 7.2 (dd, 2 H); 7.5 (s, 1 H); 7.6 (s, 1 H); 8.2 (d, 1 H) |
| 145.8 | CH₃ | SO₂CH₃ | CH₂O | 4-chloro-1-pyrazolyl | | 3.4 (s, 3 H); 3.6 (s, 3 H); 3.9 (s, 3 H); 6.1 (s, 2 H); 7.2 (s, 1 H); 7.4 (s, 1 H); 7.5 (s, 1 H); 7.6 (d, 1 H); 8.2 (d, 1 H) |
| 145.9 | CH₃ | H | CH₂O | 2-pyridyl | 94 | |
| 145.10 | CH₃ | iso-propyl | CH₂O | 2-pyridyl | 66 | |
| 145.11 | C₂H₅ | H | CH₂O | 1-pyrazolyl | 63 | |
| 145.12 | C₂H₅ | H | CH₂O | 2-pyridyl | 90 | |

USE EXAMPLES

The herbicidal activity of the substituted 4-benzoylpyrazoles of the formula I was demonstrated by greenhouse experiments:

The culture containers used were plastic pots containing loamy sand with approximately 3.0% of humus as the substrate. The seeds of the test plants were sown separately for each species.

For the pre-emergence treatment, the active compounds, which had een suspended or emulsified in water, were applied directly after sowing by means of finely distributing nozzles. The containers were irrigated gently to promote germination and growth and subsequently covered with transparent plastic hoods until the plants had rooted. This cover caused uniform germination of the test plants, unless this was adversely affected by the active compounds.

For the post-emergence treatment, the test plants were first grown to a height of 3 to 15 cm, depending on the plant habit, and only then treated with the active compounds which had been suspended or emulsified in water. The test plants were for this purpose either sown directly and grown in the same containers, or they were first grown separately as seedlings and transplanted into the test containers a few days prior to treatment.

Depending on the species, the plants were kept at 10–25° C. or 20–35° C. The test period extended over 2 to 4 weeks. During this time, the plants were tended, and their response to the individual treatments was evaluated.

The evaluation was carried out using a scale from 0 to 100. 100 means no emergence of the plants, or complete destruction of at least the aerial parts and 0 means no damage, or normal course of growth.

We claim:

1. A 4-benzoylpyrazole of the formula I

I $$\underset{R^1 \quad R^2}{\overset{O}{\underset{\|}{Q-C}}-\text{phenyl}-X^1-\text{Het}}$$

where:

R¹ and R² are each hydrogen, mercapto, nitro, halogen, cyano, thiocyanato, $C_1$–$C_6$-alkyl, $C_1$–$C_6$-haloalkyl, $C_1$–$C_6$-alkoxy-$C_1$–$C_6$-alkyl, $C_2$–$C_6$-alkenyl, $C_2$–$C_6$-alkynyl, —OR³, —OCOR³, —OSO₂R³, —S(O)ₙR³, —SO₂OR³, —SO₂N(R³)₂, —NR³SO₂R³ or —NR³COR³;

R³ is hydrogen, $C_1$–$C_6$-alkyl, $C_1$–$C_6$-haloalkyl, $C_2$–$C_6$-alkenyl, $C_2$–$C_6$-alkynyl, phenyl or phenyl-$C_1$–$C_6$-alkyl; where the abovementioned alkyl radicals may be partially or fully halogenated and/or may carry one to three of the following groups:

hydroxyl, mercapto, amino, cyano, R³, —OR³, —SR³, —N(R³)₂, =NOR³, —OCOR³, —SCOR³, —NR³COR³, —CO₂R³, —COSR³, —CON(R³)₂, $C_1$–$C_4$-alkyliminooxy, $C_1$–$C_4$-alkoxyamino, $C_1$–$C_4$-alkylcarbonyl, $C_1$–$C_4$-alkoxy-$C_2$–$C_6$-alkoxycarbonyl, $C_1$–$C_4$-alkylsulfonyl heterocyclyl, heterocyclyloxy, phenyl, benzyl, hetaryl, phenoxy, benzyloxy and hetaryloxy, where the eight last-mentioned radicals may in turn be substituted;

n is 0, 1 or 2;

Q is a pyrazole of the formula II

II

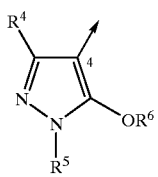

which is attached in position 4 and where

R⁴ is hydrogen, $C_1$–$C_6$-alkyl or $C_1$–$C_6$-haloalkyl;

R⁵ is $C_1$–$C_6$-alkyl, $C_1$–$C_6$-haloalkyl, phenyl or phenyl which may be partially or fully halogenated and/or may carry one to three of the following radicals: nitro, cyano, $C_1$–$C_4$-alkyl, $C_1$–$C_4$-haloalkyl, $C_1$–$C_4$-alkoxy, $C_1$–$C_4$-haloalkoxy;

R⁶ is hydrogen, $C_1$–$C_6$-alkyl, $C_1$–$C_6$-haloalkyl, $C_1$–$C_6$-alkylcarbonyl, $C_1$–$C_6$-haloalkylcarbonyl, $C_1$–$C_6$-alkoxycarbonyl, $C_1$–$C_6$-alkylsulfonyl, $C_1$–$C_6$-haloalkylsulfonyl, phenylcarbonyl, phenylcarbonylmethyl, phenoxycarbonyl or phenylsulfonyl, where the four last-mentioned substituents are unsubstituted, or the phenyl ring in question may be partially or fully halogenated and/or may carry one to three of the following radicals:
nitro, cyano, $C_1$–$C_4$-alkyl, $C_1$–$C_4$-haloalkyl, $C_1$–$C_4$-alkoxy, $C_1$–$C_4$-haloalkoxy;

$X^1$ is a straight-chain or branched $C_1$–$C_6$-alkylene, a $C_2$–$C_6$-alkenylene or a $C_2$–$C_6$-alkynylene chain which is interrupted by a hetero atom selected from the group consisting of:
oxygen and sulfur,
where the abovementioned alkylene, alkenylene or alkynylene radicals may be partially halogenated and/or may carry one to three of the following groups:
—OR$^7$, —OCOR$^7$, —OCONHR$^7$ or —OSO$_2$R$^7$;

$R^7$ is hydrogen, $C_1$–$C_6$-alkyl, $C_2$–$C_6$-alkenyl, $C_2$–$C_6$-alkynyl, phenyl, phenyl-$C_1$–$C_6$-alkyl, where the abovementioned alkyl, alkenyl or alkynyl radicals may be partially or fully halogenated and/or may be substituted by one or more of the following radicals:
hydroxyl, mercapto, amino, cyano, nitro, formyl, $C_1$–$C_4$-alkylamino, $C_1$–$C_4$-dialkylamino, $C_1$–$C_4$-alkoxycarbonyl, $C_1$–$C_4$-alkylcarbonyl, $C_1$–$C_4$-alkylcarbonyloxy, $C_1$–$C_4$-alkyl, $C_1$–$C_4$-haloalkyl, $C_1$–$C_4$-alkylthio, $C_1$–$C_4$-haloalkylthio, $C_1$–$C_4$-alkoxy, $C_1$–$C_4$-haloalkoxy;

Het is a three- to six-membered partially or fully saturated heterocyclic group or a three- to six-membered heteroaromatic group having up to three hetero atoms selected from the following three groups:
nitrogen,
oxygen in combination with at least one nitrogen or
sulfur in combination with at least one nitrogen;
where the abovementioned heterocyclic or heteroaromatic group may be partially or fully halogenated and/or may be substituted by $R^8$;

$R^8$ is hydrogen, hydroxyl, mercapto, amino, cyano, nitro, formyl, $C_1$–$C_4$-alkylamino, $C_1$–$C_4$-dialkylamino, $C_1$–$C_4$-alkoxycarbonyl, $C_1$–$C_4$-alkylcarbonyl, $C_1$–$C_4$-alkylcarbonyloxy, $C_1$–$C_4$-alkyl, $C_1$–$C_4$-haloalkyl, $C_1$–$C_4$-alkylthio, $C_1$–$C_4$-haloalkylthio, $C_1$–$C_4$-alkoxy, $C_1$–$C_4$-haloalkoxy, where the alkyl radicals may in each case be substituted by in each case one or more of the following radicals:
cyano, formyl, $C_1$–$C_4$-alkylamino, $C_1$–$C_4$-dialkylamino, $C_1$–$C_4$-alkoxycarbonyl, $C_1$–$C_4$-alkylcarbonyl, $C_1$–$C_4$-alkylcarbonyloxy, $C_1$–$C_4$-alkyl, $C_1$–$C_4$-haloalkyl, $C_1$–$C_4$-alkylthio, $C_1$–$C_4$-haloalkylthio, $C_1$–$C_4$-alkoxy, $C_1$–$C_4$-haloalkoxy;

and agriculturally useful salts thereof.

2. A 4-benzoylpyrazole of the formula I as claimed in claim 1, where $R^1$ is nitro, halogen, cyano, thiocyanato, $C_1$–$C_6$-alkyl, $C_1$–$C_6$-haloalkyl, $C_1$–$C_6$-alkoxy-$C_1$–$C_6$-alkyl, $C_2$–$C_6$-alkenyl, $C_2$–$C_6$-alkynyl, —OR$^3$ or —S(O)$_n$R$^3$;

$R^2$ is hydrogen or one of the radicals mentioned above under $R^1$.

3. A 4-benzoylpyrazole of the formula Ia as claimed in claim 1 or 2,

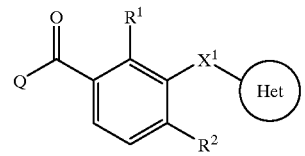

where the substituents $R^1$, $R^2$, Q, $X^1$ and Het are each as defined under claim 1.

4. A 4-benzoylpyrazole of the formula Ia as claimed in claim 3, where $X^1$ is a $C_1$–$C_3$-alkylene, $C_2$–$C_3$-alkenylene or $C_2$–$C_3$-alkynylene chain which is interrupted by an oxygen.

5. A 4-benzoylpyrazole of the formula Ia as claimed in claim 3, where Het is a five- or six-membered partially or fully saturated heterocyclic or a five- or six-membered heteroaromatic group having up to three hetero atoms selected from the following three groups:
nitrogen,
oxygen in combination with at least one nitrogen or
sulfur in combination with at least one nitrogen.

6. A process for preparing 4-benzoylpyrazoles of the formula I as claimed in claim 1, which comprises acylating a pyrazole of the formula IIa, where the substituents $R^4$ and $R^5$ are each as defined under claim 1,

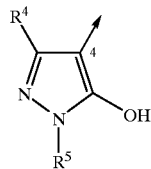

with an activated carboxylic acid IIIa or with a carboxylic acid IIIb,

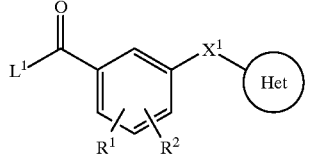

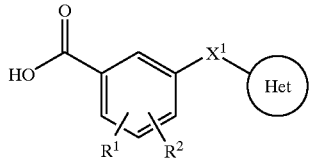

where the substituents $R^1$, $R^2$, $X^1$ and Het are each as defined in claim 1 and $L^1$ is a nucleophilically replaceable leaving group, and rearranging the acylation product, optionally in the presence of a catalyst, to give the compounds I and, when $R^6$ in formula I is not H, reacting these with a compound of the formula IV $$L^2\text{-}R^6 \qquad \text{IV}$$

(where $R^6 \neq H$)

where $R^6$ is as defined under claim 1 except for hydrogen and $L^2$ is a nucleophilically replaceable leaving group, to prepare 4-benzoylpyrazoles of the formula I where $R^6 \neq H$.

7. An activated carboxylic acid of the formula IIIa and a carboxylic acid of the formula IIIb as defined in claim 6.

8. A composition comprising a herbicidally effective amount of at least one 4-benzoylpyrazole of the formula I or an agriculturally useful salt of I as claimed in claim 1 and auxiliaries which are customarily used for formulating crop protection agents.

9. A process for preparing herbicidally active compositions as claimed in claim 8, which comprises mixing a herbicidally effective amount of at least one 4-benzoylpyrazole of the formula I or an agriculturally useful salt of I as claimed in claim 1 and auxiliaries which are customarily used for formulating crop protection agents.

10. A method for controlling undesirable vegetation, which comprises allowing a herbicidally effective amount of at least one 4-benzoylpyrazole of the formula I or an agriculturally useful salt of I as claimed in claim 1 to act on plants, their habitat and/or on seeds.

* * * * *